US009347072B2

(12) United States Patent
Warren et al.

(10) Patent No.: US 9,347,072 B2
(45) Date of Patent: *May 24, 2016

(54) VIP3 TOXINS AND METHODS OF USE

(71) Applicant: Syngenta Participations AG, Basel (CH)

(72) Inventors: Gregory W. Warren, Research Triangle Park, NC (US); Vance Cary Kramer, Research Triangle Park, NC (US); Frank Arthur Shotkoski, Ithaca, NY (US); Zhicheng Shen, Hangzhou (CN)

(73) Assignee: Syngenta Participations Ag, Basel (CH)

( * ) Notice: Subject to any disclaimer, the term of this patent is extended or adjusted under 35 U.S.C. 154(b) by 242 days.

This patent is subject to a terminal disclaimer.

(21) Appl. No.: 14/176,612

(22) Filed: Feb. 10, 2014

(65) Prior Publication Data

US 2014/0212394 A1    Jul. 31, 2014

Related U.S. Application Data

(62) Division of application No. 12/106,847, filed on Apr. 21, 2008, now Pat. No. 8,686,232, which is a division of application No. 10/505,315, filed as application No. PCT/US03/04735 on Feb. 20, 2003, now Pat. No. 7,378,493.

(60) Provisional application No. 60/362,250, filed on Mar. 6, 2002.

(51) Int. Cl.
| | |
|---|---|
| *C12N 15/82* | (2006.01) |
| *C07K 14/325* | (2006.01) |
| *A01N 63/00* | (2006.01) |
| *A01N 63/02* | (2006.01) |
| *C07K 14/32* | (2006.01) |
| *C07H 21/04* | (2006.01) |

(52) U.S. Cl.
CPC ............ *C12N 15/8286* (2013.01); *A01N 63/00* (2013.01); *A01N 63/02* (2013.01); *C07K 14/32* (2013.01); *C07H 21/04* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 5,625,136 | A | 4/1997 | Koziel et al. |
| 5,877,012 | A | 3/1999 | Estruch et al. |
| 6,107,279 | A | 8/2000 | Estruch et al. |
| 6,137,033 | A | 10/2000 | Estruch et al. |
| 6,174,860 | B1 | 1/2001 | Kramer et al. |
| 6,291,156 | B1 | 9/2001 | Estruch et al. |
| 6,369,213 | B1* | 4/2002 | Schnepf ............... C07K 14/325 424/93.461 |
| 8,686,232 | B2* | 4/2014 | Shen ...................... A01N 63/00 424/93.2 |

FOREIGN PATENT DOCUMENTS

| | | |
|---|---|---|
| WO | 9746105 | 12/1997 |
| WO | 9800546 | 1/1998 |
| WO | 9818932 | 5/1998 |
| WO | 9844137 | 10/1998 |
| WO | 9933991 | 7/1999 |
| WO | 9957282 | 11/1999 |
| WO | 02078437 | 10/2002 |

OTHER PUBLICATIONS

Argolo-Filho et al, 2014, Insects 5:62-91.*
Murray, E.E., et al., Codon usage in plant genes. Nucleic Acids Research. (1989). p. 477-498, 17(2).
Estruch et al., Vip3, a novel Bacillus thuringiensis vegetative insecticidal protein with a wide spectrum of activities against lepidopteran insects, Proceedings National Academy of Science, 1996, 93, p. 5389-5494.
Selvapandiyan, A. et al., The Bacillus thuringiensis Toxicity Analysis of N- and C-terminus-deleted Vegetative Insecticidal Protein from Bacillus thuringiensis, Applied and Environmental Microbiology, 2001, 67(12), p. 5855-5858.
Yu et al., The Bacillus Thuringiensis Vegetative Insecticidal Protein Vip3 a Lyses Midgut Epithelium Cells of Susceptible Insects, Applied and Environmental Microbiology, 1997, 63, p. 532-536.
Loguercio et al. First-tier screening for Vip-derived activities in tropical Bacillus thuringiensis strains by PCR and feeding bioassays: A critical assessment. GenBank Database [online], (Jul. 11, 2001), Accession No. AAK97481.
Loguercio et al. First-tier screening for Vip-derived activities in tropical Bacillus thuringiensis strains by PCR and feeding bioassays: A critical assessment. GenBank Database [online], (Jul. 11, 2001), Accession No. AAK97482.
Loguercio et al. First-tier screening for Vip-derived activities in tropical Bacillus thuringiensis strains by PCR and feeding bioassays: A critical assessment. GenBank Database [online], (Jul. 13, 2001), Accession No. AAK97484.
Loguercio et al. First-tier screening for Vip-derived activities in tropical Bacillus thuringiensis strains by PCR and feeding bioassays: A critical assessment. GenBank Database [online], (Jul. 13, 2001), Accession No. AAK97485.
Loguercio et al. First-tier screening for Vip-derived activities in tropical Bacillus thuringiensis strains by PCR and feeding bioassays: A critical assessment. GenBank Database [online], (Jul. 14, 2001), Accession No. AAK97486.
Loguercio et al. First-tier screening for Vip-derived activities in tropical Bacillus thuringiensis strains by PCR and feeding bioassays: A critical assessment. GenBank Database [online], (Jul. 11, 2001), Accession No. AAK97487.

(Continued)

*Primary Examiner* — Anne Kubelik
(74) *Attorney, Agent, or Firm* — Karen Magri

(57) ABSTRACT

Nucleic acid molecules encoding novel Vip3 toxins that are highly active against a wide range of lepidopteran insect pests are disclosed. The nucleic acid molecules can be used to transform various prokaryotic and eukaryotic organisms to express the Vip3 toxins. These recombinant organisms can be used to control lepidopteran insects in various environments.

27 Claims, No Drawings

(56) References Cited

OTHER PUBLICATIONS

Doss et al. Cloning and expression of the vegetative insecticidal protein (Vip3V) gene of Bacillus thuringiensis in *Escherichia coli*. GenBank Database [online], (Apr. 23, 2001), Accession No. AF373030.

Cai et al. Vegetative insecticidal protein gene vip83 from Bacillus thuringiensis server leesis strain YBT-833. GenBank Database [online], (Jul. 8, 2001), Accession No. AY044227.

Yu et al. Closing and expression of Vip3A gene from Bacillus thuringiensis strain S10-1. GenBank Database [online], (Jan. 17, 2002), Accession No. AY074706.

Chen et al. Cloning and expression of Vip3A gene from Bacillus thuringiensis strain S10-1. GenBank Database [online], (Jan. 17, 2002), Accession No. AY074707.

Chen et al. Cloning and expression of Vip3A gene from Bacillus thuringiensis strain S10-1. GenBank Database [online], (Jan. 17, 2002), Accession No. AY074708.

Lee et al., Appl. Environ. Microbiol., 2003, 69, p. 4648-4657.

Guo et al., Proc. Natl. Acad. Sci. USA, 2004, 101, p. 9205-9210.

International Search Report dated May 27, 2004 for International Patent Application No. PCT/US2003/004735.

* cited by examiner

VIP3 TOXINS AND METHODS OF USE

CROSS-REFERENCE TO RELATED APPLICATIONS

This application is a divisional of U.S. application Ser. No. 12/106,847 filed Apr. 21, 2008 (allowed), which is a divisional of U.S. application Ser. No. 10/505,315 (now U.S. Pat. No. 7,378,493), which claims priority under 35 U.S.C. §371 from PCT Application No. PCT/US03/04735, filed Feb. 20, 2003, which claims the benefit of U.S. Provisional Application No. 60/362,250 filed Mar. 6, 2002, which applications are incorporated herein by reference in their entirety.

FIELD OF THE INVENTION

The present invention relates to novel Vip3 toxins from *Bacillus thuringiensis*, nucleic acid sequences whose expression results in said toxins, and methods of making and methods of using the toxins and corresponding nucleic acid sequences to control insects.

BACKGROUND OF THE INVENTION

Plant pests are a major factor in the loss of the world's important agricultural crops. About $8 billion are lost every year in the U.S. alone due to infestations of non-mammalian pests including insects. In addition to losses in field crops, insect pests are also a burden to vegetable and fruit growers, to producers of ornamental flowers, and to home gardeners.

Insect pests are mainly controlled by intensive applications of chemical pesticides, which are active through inhibition of insect growth, prevention of insect feeding or reproduction, or cause death. Good insect control can thus be reached, but these chemicals can sometimes also affect other, beneficial insects. Another problem resulting from the wide use of chemical pesticides is the appearance of resistant insect varieties. This has been partially alleviated by various resistance management practices, but there is an increasing need for alternative pest control agents. Biological pest control agents, such as *Bacillus thuringiensis* strains expressing pesticidal toxins like δ-endotoxins, have also been applied to crop plants with satisfactory results, offering an alternative or compliment to chemical pesticides. The genes coding for some of these δ-endotoxins have been isolated and their expression in heterologous hosts have been shown to provide another tool for the control of economically important insect pests. In particular, the expression of insecticidal toxins in transgenic plants, such as *Bacillus thuringiensis* δ-endotoxins, has provided efficient protection against selected insect pests, and transgenic plants expressing such toxins have been commercialized, allowing farmers to reduce applications of chemical insect control agents.

Other, non-endotoxin genes and the proteins they encode have now been identified. U.S. Pat. Nos. 5,877,012, 6,107,279, 6,137,033, and 6,291,156, as well as Estruch et al. (1996, Proc. Natl. Acad. Sci. 93:5389-5394) and Yu et al. (1997, Appl. Environ. Microbiol. 63:532-536), herein incorporated by reference, describe a new class of insecticidal proteins called Vip3. Vip3 genes encode approximately 88 kDa proteins that are produced and secreted by *Bacillus* during its vegetative stages of growth (vegetative insecticidal proteins, VIP). The Vip3A protein possesses insecticidal activity against a wide spectrum of lepidopteran pests, including, but not limited to, black cutworm (BCW, *Agrotis ipsilon*), fall armyworm (FAW, *Spodoptera frugiperda*), tobacco budworm (TBW, *Heliothis virescens*), and corn earworm (CEW, *Helicoverpa zea*). More recently, plants expressing the Vip3A protein have been found to be resistant to feeding damage caused by hemipteran insect pests. Thus, the Vip3A protein displays a unique spectrum of insecticidal activities. Other disclosures, WO 98/18932, WO 98/33991, WO 98/00546, and WO 99/57282, have also now identified homologues of the Vip3 class of proteins.

The continued use of chemical and biological agents to control insect pests heightens the chance for insects to develop resistance to such control measures. Also, only a few specific insect pests are controllable with each control agent.

Therefore, there remains a need to discover new and effective pest control agents that provide an economic benefit to farmers and that are environmentally acceptable. Particularly needed are control agents that are targeted to a wide spectrum of economically important insect pests, to control agents that efficiently control insect strains that are or could become resistant to existing insect control agents, and those with increased potency compared to current control agents. Furthermore, agents whose application minimizes the burden on the environment are desirable.

SUMMARY

The present invention addresses the need for novel pest control agents by providing new genes and toxins that are distinct from those disclosed in U.S. Pat. Nos. 5,877,012, 6,107,279, and 6,137,033, and Estruch et al. (1996), and Yu et al. (1997), as well as WO 98/18932, WO 99/33991, WO 99/5782, and WO 98/00546.

Within the present invention, compositions and methods for controlling plant pests are provided. In particular, novel vip3 nucleic acid sequences isolated from *Bacillus thuringiensis*, and sequences substantially identical thereto, whose expression results in pesticidal toxins with toxicity to economically important insect pests, particularly insect pests that infest plants, are provided. The invention is further drawn to the novel pesticidal toxins resulting from the expression of the nucleic acid sequences, and to compositions and formulations containing the pesticidal toxins, which are capable of inhibiting the ability of insect pests to survive, grow and reproduce, or of limiting insect-related damage or loss to crop plants. The invention is also drawn to methods of using the nucleic acid sequences, for example in making hybrid toxins with enhanced pesticidal activity or in a recombinogenic procedure such as DNA shuffling. The invention is further drawn to a method of making the toxins and to methods of using the nucleic acid sequences, for example in microorganisms to control insects or in transgenic plants to confer protection from insect damage, and to a method of using the pesticidal toxins, and compositions and formulations comprising the pesticidal toxins, for example applying the pesticidal toxins or compositions or formulations to insect-infested areas, or to prophylactically treat insect-susceptible areas or plants to confer protection against the insect pests.

The nucleotide sequences of the present invention can be engineered using methods generally known in the art in order to alter the nucleotide sequences for a variety of purposes including, but not limited to, broadening the spectrum of pesticidal activity, or increasing the specific activity against a specific pest. DNA shuffling by random fragmentation and PCR reassembly of gene fragments and synthetic oligonucleotides may be used to engineer the nucleotide sequences.

The novel pesticidal toxins described herein are highly active against insects. For example, a number of economically important insect pests, such as the lepidopterans *Ostrinia nubilalis* (European corn borer), *Plutella xylostella*

(diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Diatraea grandiosella* (southwestern corn borer), *Diatraea saccharalis* (sugarcane borer), *Helicoverpa punctigera* (native budworm) and *Helicoverpa armigera* (cotton bollworm) can be controlled by the pesticidal toxins. The pesticidal toxins can be used singly or in combination with other insect control strategies to confer maximal pest control efficiency with minimal environmental impact.

According to one aspect, the present invention provides an isolated nucleic acid molecule comprising a nucleotide sequence that encodes a toxin that is active against insects, wherein the nucleotide sequence: (a) has a compliment that hybridizes to nucleotides 1981-2367 of SEQ ID NO: 1 in 7% sodium dodecyl sulfate (SDS), 0.5 M NaPO$_4$, 1 mM EDTA at 50° C. with washing in 0.1×SSC, 0.1% SDS at 65° C.; or (b) is isocoding with the nucleotide sequence of (a); or (c) comprises a consecutive 20 base pair nucleotide portion identical in sequence to a consecutive 20 base pair nucleotide portion of a nucleotide sequence of (a) or (b); or (d) has at least 93% sequence identity with SEQ ID NO: 1; or (e) encodes an amino acid sequence having at least 91% sequence identity with SEQ ID NO: 2.

In one embodiment of this aspect, the isolated nucleic acid molecule comprises a nucleotide sequence that has a compliment that hybridizes to nucleotides 1981-2367 of SEQ ID NO: 1 in 7% sodium dodecyl sulfate (SDS), 0.5 M NaPO$_4$, 1 mM EDTA at 50° C. with washing in 0.1×SSC, 0.1% SDS at 65° C.

In another embodiment of this aspect, the isolated nucleic acid molecule comprises a nucleotide sequence that is isocoding with a nucleotide sequence having a compliment that hybridizes to nucleotides 1981-2367 of SEQ ID NO: 1 in 7% sodium dodecyl sulfate (SDS), 0.5 M NaPO$_4$, 1 mM EDTA at 50° C. with washing in 0.1×SSC, 0.1% SDS at 65° C.

In yet another embodiment, the isolated nucleic acid molecule comprises a consecutive 20 base pair nucleotide portion identical in sequence to a consecutive 20 base pair nucleotide portion of nucleotides 1981-2367 of the nucleotide sequences set forth in SEQ ID NO: 1 or SEQ ID NO: 3.

In another embodiment, the isolated nucleic acid molecule comprises a nucleotide sequence that has at least 75% sequence identity with nucleotides 1981-2367 of SEQ ID NO: 1. Preferably, the isolated nucleic acid molecule comprises a nucleotide sequence that has at least 85% sequence identity with nucleotides 1981-2367 of SEQ ID NO: 1. More preferably, the isolated nucleic acid molecule comprises a nucleotide sequence that has at least 95% sequence identity with nucleotides 1981-2367 of SEQ ID NO: 1. Even more preferably, the isolated nucleic acid molecule comprises a nucleotide sequence that has at least 99% sequence identity with nucleotides 1981-2367 of SEQ ID NO: 1. Most preferably, the isolated nucleic acid molecule comprises nucleotides 1981-2367 of SEQ ID NO: 1 or SEQ ID NO: 3.

In another embodiment, the isolated nucleic acid molecule comprises a nucleotide sequence that has at least 93% sequence identity with SEQ ID NO: 1. Preferably, the isolated nucleic acid molecule comprises a nucleotide sequence that has at least 95% sequence identity with SEQ ID NO: 1. More preferably, the isolated nucleic acid molecule comprises a nucleotide sequence that has at least 99% sequence identity with SEQ ID NO: 1. Most preferably, the isolated nucleic acid molecule comprises nucleotides 1-2367 of a nucleotide sequence selected from the group consisting of SEQ ID NO: 1, SEQ ID NO: 3, SEQ ID NO: 10, SEQ ID NO: 31, and SEQ ID NO: 33.

In one embodiment of the present invention, the isolated nucleic acid molecule encodes a toxin comprising an amino acid sequence with at least 75% identity with amino acids 661-788 of the amino acid sequence of SEQ ID NO: 2. Preferably, the isolated nucleic acid molecule encodes a toxin comprising an amino acid sequence which has at least 85% identity with amino acids 661-788 of the amino acid sequence of SEQ ID NO: 2. More preferably, the isolated nucleic acid molecule encodes a toxin comprising an amino acid sequence which has at least 95% identity with amino acids 661-788 of the amino acid sequence of SEQ ID NO: 2. Even more preferably, the isolated nucleic acid molecule encodes a toxin comprising an amino acid sequence which has at least 99% identity with amino acids 661-788 of the amino acid sequence of SEQ ID NO: 2. Most preferably, the isolated nucleic acid molecule encodes a toxin comprising amino acids 661-788 of SEQ ID NO: 2.

In another embodiment, the isolated nucleic acid molecule encodes a toxin comprising an amino acid sequence which has at least 91% identity to the amino acid sequence set forth in SEQ ID NO: 2. Preferably, the isolated nucleic acid molecule encodes a toxin comprising an amino acid sequence which has at least 95% identity to the amino acid sequence set forth in SEQ ID NO: 2. More preferably, the isolated nucleic acid molecule encodes a toxin comprising an amino acid sequence which has at least 99% identity to the amino acid sequence set forth in SEQ ID NO: 2. Most preferably, the isolated nucleic acid molecule encodes a toxin comprising the amino acid sequence set forth in SEQ ID NO: 2 or SEQ ID NO: 12.

In one embodiment, the isolated nucleic acid molecule is comprised in a *Bacillus thuringiensis* isolate selected from the group consisting of C1674, designated NRRL accession B-30556; and C536, designated NRRL accession B-30557.

In another embodiment, the isolated nucleic acid molecule comprises the approximately 2.4 kb DNA fragment comprised in an *E. coli* clone selected from the group consisting of pNOV3910, designated NRRL accession B-30553; pNOV3911, designated NRRL accession B-30552; pNOV3906, designated NRRL accession B-30555; pNOV3905, designated NRRL accession B-30554; and pNOV3912, designated NRRL accession B-30551.

According to one embodiment of the invention, the isolated nucleic acid molecule encodes a toxin that is active against a lepidopteran insect. Preferably, according to this embodiment, the toxin has activity against *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth).

The present invention also provides a chimeric gene comprising a heterologous promoter sequence operatively linked to the nucleic acid molecule of the invention. Further, the present invention provides a recombinant vector comprising such a chimeric gene. Still further, the present invention provides a transgenic host cell comprising such a chimeric gene. A transgenic host cell according to this aspect of the invention may be an animal cell, an animal virus, a plant virus, a bacterial cell, a yeast cell or a plant cell, preferably, a plant cell. Even further, the present invention provides a transgenic plant comprising such a plant cell. A transgenic plant according to this aspect of the invention may be sorghum, wheat, sunflower, tomato, cole crops, cotton, rice, soybean, sugar beet, sugarcane, tobacco, barley, oilseed rape or maize, preferably maize and cotton. Still further, the present invention provides seed from the group of transgenic plants consisting of sorghum, wheat, sunflower, tomato, cole crops, cotton, rice, soybean, sugar beet, sugarcane, tobacco, barley, oilseed rape and maize. In a particularly preferred embodiment, the seed is from a transgenic maize plant or transgenic cotton plant.

Also provided by the invention are transgenic plants of the invention further comprising a second nucleic acid sequence or groups of nucleic acid sequences that encode a second pesticidal principle. Particularly preferred second nucleic acid sequences are those that encode a δ-endotoxin, those that encode another Vegetative Insecticidal Protein toxin or those that encode a pathway for the production of a non-proteinaceous pesticidal principle.

In yet another aspect, the present invention provides toxins produced by the expression of the nucleic acid molecules of the present invention.

In a preferred embodiment, the toxin is produced by the expression of the nucleic acid molecule comprising nucleotides 1-2367 of a nucleotide sequence selected from the group consisting of SEQ ID NO: 1, SEQ ID NO: 3, and SEQ ID NO: 10.

In another embodiment, the toxins of the invention are active against lepidopteran insects, preferably against *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth).

In one embodiment, the toxins of the present invention are produced by a *Bacillus thuringiensis* isolate selected from the group consisting of C1674, designated NRRL accession B-30556; and C536, designated NRRL accession B-30557.

In another embodiment, the toxins are produced by an *E. coli* clone selected from the group consisting of pNOV3910, designated NRRL accession B-30553; pNOV3911, designated NRRL accession B-30552; pNOV3906, designated NRRL accession B-30555; pNOV3905, designated NRRL accession B-30554; and pNOV3912, designated NRRL accession B-30551.

In one embodiment, a toxin of the present invention comprises an amino acid sequence which has at least 75% identity with amino acids 661-788 of the amino acid sequence of SEQ ID NO: 2. Preferably, the toxin comprises an amino acid sequence which has at least 85% identity with amino acids 661-788 of the amino acid sequence of SEQ ID NO: 2. More preferably, the toxin comprises an amino acid sequence which has at least 95% identity with amino acids 661-788 of the amino acid sequence of SEQ ID NO: 2. Even more preferably, the toxin comprises an amino acid sequence that has at least 99% identity with amino acids 661-788 of the amino acid sequence of SEQ ID NO: 2. Most preferably, the toxin comprises amino acids 661-788 of SEQ ID NO: 2.

In another embodiment, a toxin of the present invention comprises an amino acid sequence which has at least 91% identity with the amino acid sequence set forth in SEQ ID NO: 2. Preferably, the toxin comprises an amino acid sequence which has at least 95% identity with the amino acid sequence set forth in SEQ ID NO: 2. More preferably, the toxin comprises an amino acid sequence which has at least 99% identity with the amino acid sequence set forth in SEQ ID NO: 2. Most preferably, the toxin comprises the amino acid sequence set forth in SEQ ID NO: 2, SEQ ID NO: 11, or SEQ ID NO: 32.

The present invention also provides a composition comprising an effective insect-controlling amount of a toxin according to the invention.

In another aspect, the present invention provides a method of producing a toxin that is active against insects, comprising: (a) obtaining a transgenic host cell comprising a chimeric gene, which itself comprises a heterologous promoter sequence operatively linked to the nucleic acid molecule of the invention; and (b) expressing the nucleic acid molecule in the transgenic cell, which results in at least one toxin that is active against insects.

In a further aspect, the present invention provides a method of producing an insect-resistant transgenic plant, comprising introducing a nucleic acid molecule of the invention into the transgenic plant, wherein the nucleic acid molecule is expressible in the transgenic plant in an effective amount to control insects. According to one embodiment, the insects are lepidopteran insects, preferably selected from the group consisting of: *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth).

In still a further aspect, the present invention provides a method of controlling insects comprising delivering to the insects an effective amount of a toxin of the present invention. According to one embodiment, the insects are lepidopteran insects, preferably selected from the group consisting of: *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth). Preferably, the toxin is delivered to the insects orally. In one preferred embodiment, the toxin is delivered orally through a transgenic plant comprising a nucleic acid sequence that expresses a toxin of the present invention.

The present invention also provides hybrid toxins active against insects, wherein the hybrid toxins are encoded by a nucleic acid molecule comprising a nucleotide sequence according to the invention.

In one embodiment, the hybrid toxins of the invention are active against lepidopteran insects, preferably against *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth).

In another embodiment, the hybrid toxin is encoded by the approximately 2.4 kb DNA fragment comprised in the *E. coli* clone pNOV3912, designated NRRL accession B-30551. In a preferred embodiment, the hybrid toxin is encoded by the nucleotide sequence set forth in SEQ ID NO: 10.

The present invention also provides a composition comprising an insecticidally effective amount of a hybrid toxin according to the invention.

In another aspect, the present invention provides a method of producing a hybrid toxin active against insects, comprising: (a) obtaining a transgenic host cell comprising a chimeric gene, which itself comprises a heterologous promoter sequence operatively linked to the nucleic acid molecule of the invention; and (b) expressing the nucleic acid molecule in the transgenic cell, which results in at least one hybrid toxin that is active against insects.

In a further aspect, the present invention provides a method of producing an insect-resistant transgenic plant, comprising introducing a nucleic acid molecule of the invention into the plant, wherein the nucleic acid molecule encodes a hybrid toxin and wherein the hybrid toxin is expressible in the transgenic plant in an effective amount to control an insect. According to one embodiment, the insects are lepidopteran insects, preferably selected from the group consisting of *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth).

In still a further aspect, the present invention provides a method of controlling an insect comprising delivering to the insects an effective amount of a hybrid toxin of the present invention. According to one embodiment, the insects are lepidopteran insects, preferably selected from the group consisting of *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth). Preferably the hybrid toxin is delivered to the insects orally. In one preferred embodiment, the hybrid toxin is delivered orally through a transgenic plant comprising a nucleic acid sequence that expresses a hybrid toxin of the present invention.

The present invention also provides a hybrid toxin active against insects, comprising a carboxy-terminal region of a Vip3 toxin joined in the amino to carboxy direction to an amino-terminal region of a different Vip3 toxin, wherein the carboxy-terminal region comprises an amino acid sequence which has at least 75% identity, preferably at least 85% identity, more preferably at least 95% identity, most preferably at least 99% identity with amino acids 661-788 of SEQ ID NO: 2; and wherein the amino-terminal region has at least 75% identity, preferably at least 85% identity, more preferably at least 95% identity, most preferably at least 99% identity with amino acids 1-660 of SEQ ID NO: 5. In a preferred embodiment, the carboxy-terminal region comprises amino acids 661-788 of SEQ ID NO: 2, and the amino-terminal region comprises amino acids 1-660 of SEQ ID NO: 5. In a most preferred embodiment, the hybrid toxin comprises amino acids 1-788 of SEQ ID NO: 11.

The hybrid toxin, according to this aspect of the invention, is preferably active against lepidopteran insects, more preferably against lepidopteran insects selected from the group consisting of *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth).

Also encompassed by this aspect of the invention is a nucleic acid molecule comprising a nucleotide sequence that encodes the hybrid toxin of this aspect.

The invention further provides a method of controlling insects wherein a transgenic plant comprising a hybrid toxin of the invention further comprises a second nucleic acid sequence or groups of nucleic acid sequences that encode a second pesticidal principle. Particularly preferred second nucleic acid sequences are those that encode a δ-endotoxin, those that encode another Vegetative Insecticidal Protein toxin or those that encode a pathway for the production of a non-proteinaceous pesticidal principle.

Yet another aspect of the present invention is the provision of a method for mutagenizing a nucleic acid molecule according to the present invention, wherein the nucleic acid molecule has been cleaved into populations of double-stranded random fragments of a desired size, comprising: (a) adding to the population of double-stranded random fragments one or more single- or double-stranded oligonucleotides, wherein the oligonucleotides each comprise an area of identity and an area of heterology to a double-stranded template polynucleotide; (b) denaturing the resultant mixture of double-stranded random fragments and oligonucleotides into single-stranded fragments; (c) incubating the resultant population of single-stranded fragments with polymerase under conditions which result in the annealing of the single-stranded fragments at the areas of identity to form pairs of annealed fragments, the areas of identity being sufficient for one member of the pair to prime replication of the other, thereby forming a mutagenized double-stranded polynucleotide; and (d) repeating the second and third steps for at least two further cycles, wherein the resultant mixture in the second step of a further cycle includes the mutagenized double-stranded polynucleotide from the third step of the previous cycle, and wherein the further cycle forms a further mutagenized double-stranded polynucleotide.

Other aspects and advantages of the present invention will become apparent to those skilled in the art from a study of the following description of the invention and non-limiting examples.

BRIEF DESCRIPTION OF THE SEQUENCES IN THE SEQUENCE LISTING

SEQ ID NO: 1 is a native vip3C nucleotide sequence.
SEQ ID NO: 2 is the amino acid sequence encoded by SEQ ID NO: 1.
SEQ ID NO: 3 is a maize optimized vip3C nucleotide sequence.
SEQ ID NO: 4 is a native vip3A(a) nucleotide sequence.
SEQ ID NO: 5 is the amino acid sequence encoded by SEQ ID NO: 5.
SEQ ID NO: 6 is a native vip3B nucleotide sequence.
SEQ ID NO: 7 is the amino acid sequence encoded by SEQ ID NO: 7.
SEQ ID NO: 8 is a native vip3Z nucleotide sequence.
SEQ ID NO: 9 is the amino acid sequence encoded by SEQ ID NO: 9.
SEQ ID NO: 10 is a hybrid vip3A-C nucleotide sequence.
SEQ ID NO: 11 is the amino acid sequence encoded by SEQ ID NO: 10.
SEQ ID NO: 12-29 are primer sequences useful in practicing the invention.

SEQ ID NO: 30 is the nucleotide sequence of the vector pNOV2149.

SEQ ID NO: 31 is the vip3C-12168 nucleotide sequence.

SEQ ID NO: 32 is the amino acid sequence encoded by SEQ ID NO: 31.

SEQ ID NO: 33 is the maize optimized vip3C-12168 nucleotide sequence.

DEPOSITS

The following material was deposited with the Agricultural Research Service, Patent Culture Collection (NRRL), 1815 North University Street, Peoria, Ill. 61604, under the terms of the Budapest Treaty on the International Recognition of the Deposit of Microorganisms for the Purposes of Patent Procedure. All restrictions on the availability of the deposited material will be irrevocably removed upon granting of the patent.

| Isolate/Clone | Accession Number | Date of Deposit |
| --- | --- | --- |
| B. t. strain C1674 | NRRL B-30556 | Feb. 7, 2002 |
| B. t. strain C536 | NRRL B-30557 | Feb. 7, 2002 |
| E. coli BL21 (pNOV3906) | NRRL B-30555 | Feb. 7, 2002 |
| E. coli BL21 (pNOV3905) | NRRL B-30554 | Feb. 7, 2002 |
| E. coli DH5α (pNOV3910) | NRRL B-30553 | Feb. 7, 2002 |
| E. coli DH5α (pNOV3911) | NRRL B-30552 | Feb. 7, 2002 |
| E. coli DH5α (pNOV3912) | NRRL B-30551 | Feb. 7, 2002 |

DEFINITIONS

"Activity" of the toxins of the invention is meant that the toxins function as orally active insect control agents, have a toxic effect, or are able to disrupt or deter insect feeding, which may or may not cause death of the insect. When a toxin of the invention is delivered to the insect, the result is typically death of the insect, or the insect does not feed upon the source that makes the toxin available to the insect.

"Associated with/operatively linked" refer to two nucleic acid sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

A "chimeric gene" is a recombinant nucleic acid sequence in which a promoter or regulatory nucleic acid sequence is operatively linked to, or associated with, a nucleic acid sequence that codes for an mRNA or which is expressed as a protein, such that the regulator nucleic acid sequence is able to regulate transcription or expression of the associated nucleic acid sequence. The regulator nucleic acid sequence of the chimeric gene is not normally operatively linked to the associated nucleic acid sequence as found in nature.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

To "control" insects means to inhibit, through a toxic effect, the ability of insect pests to survive, grow, feed, and/or reproduce, or to limit insect-related damage or loss in crop plants. To "control" insects may or may not mean killing the insects, although it preferably means killing the insects.

Corresponding to: in the context of the present invention, "corresponding to" or "corresponds to" means that when the nucleic acid coding sequences or amino acid sequences of different Vip3 genes or proteins are aligned with each other, the nucleic or amino acids that "correspond to" certain enumerated positions are those that align with these positions but that are not necessarily in these exact numerical positions relative to the particular Vip3's respective nucleic acid coding sequence or amino acid sequence. Likewise, when the coding or amino acid sequence of a particular Vip3 (for example, Vip3Z) is aligned with the coding or amino acid sequence of a reference Vip3 (for example, Vip3C), the nucleic acids or amino acids in the Vip3Z sequence that "correspond to" certain enumerated positions of the Vip3C sequence are those that align with these positions of the Vip3C sequence, but are not necessarily in these exact numerical positions of the Vip3Z protein's respective nucleic acid coding sequence or amino acid sequence.

To "deliver" a toxin means that the toxin comes in contact with an insect, resulting in toxic effect and control of the insect. The toxin can be delivered in many recognized ways, e.g., orally by ingestion by the insect or by contact with the insect via transgenic plant expression, formulated protein composition(s), sprayable protein composition(s), a bait matrix, or any other art-recognized toxin delivery system.

"Effective insect-controlling amount" means that concentration of toxin that inhibits, through a toxic effect, the ability of insects to survive, grow, feed and/or reproduce, or to limit insect-related damage or loss in crop plants. "Effective insect-controlling amount" may or may not mean killing the insects, although it preferably means killing the insects.

"Expression cassette" as used herein means a nucleic acid sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development.

A "gene" is a defined region that is located within a genome and that, besides the aforementioned coding nucleic acid sequence, comprises other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

"Gene of interest" refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

A "heterologous" nucleic acid sequence is a nucleic acid sequence not naturally associated with a host cell into which it is introduced, including non-naturally occurring multiple copies of a naturally occurring nucleic acid sequence.

A "homologous" nucleic acid sequence is a nucleic acid sequence naturally associated with a host cell into which it is introduced.

"Homologous recombination" is the reciprocal exchange of nucleic acid fragments between homologous nucleic acid molecules.

"Hybrid toxin" as used herein is an insecticidal toxin made by the hand of man which comprises amino acid regions or fragments of one toxin joined with amino acid regions or fragments from a different toxin. For example, without limitation, joining the C-terminal region of Vip3C, from amino acids 661-788 of SEQ ID NO: 2, with the N-terminal region of Vip3A, from amino acid 1-660 of SEQ ID NO: 4, creates a hybrid toxin with an amino acid sequence set forth in SEQ ID NO: 11.

"Insecticidal" is defined as a toxic biological activity capable of controlling insects, preferably by killing them.

A nucleic acid sequence is "isocoding with" a reference nucleic acid sequence when the nucleic acid sequence encodes a polypeptide having the same amino acid sequence as the polypeptide encoded by the reference nucleic acid sequence.

An "isolated" nucleic acid molecule or an isolated protein or toxin is a nucleic acid molecule or protein or toxin that, by the hand of man, exists apart from its native environment and is therefore not a product of nature. An isolated nucleic acid molecule or protein or toxin may exist in a purified form or may exist in a non-native environment such as, for example, a recombinant host cell or a transgenic plant.

Native: refers to a gene that is present in the genome of an untransformed cell.

Naturally occurring: the term "naturally occurring" is used to describe an object that can be found in nature as distinct from being artificially produced by man. For example, a protein or nucleotide sequence present in an organism (including a virus), which can be isolated from a source in nature and which has not been intentionally modified by man in the laboratory, is naturally occurring.

A "nucleic acid molecule" or "nucleic acid sequence" is a linear segment of single- or double-stranded DNA or RNA that can be isolated from any source. In the context of the present invention, the nucleic acid molecule is preferably a segment of DNA.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A "promoter" is an untranslated DNA sequence upstream of the coding region that contains the binding site for RNA polymerase II and initiates transcription of the DNA. The promoter region may also include other elements that act as regulators of gene expression.

A "protoplast" is an isolated plant cell without a cell wall or with only parts of the cell wall.

"Regulatory elements" refer to sequences involved in controlling the expression of a nucleotide sequence. Regulatory elements comprise a promoter operably linked to the nucleotide sequence of interest and termination signals. They also typically encompass sequences required for proper translation of the nucleotide sequence.

A "shuffled" nucleic acid is a nucleic acid produced by a shuffling procedure such as any shuffling procedure set forth herein. Shuffled nucleic acids are produced by recombining (physically or virtually) two or more nucleic acids (or character strings), e.g., in an artificial, and optionally recursive, fashion. Generally, one or more screening steps are used in shuffling processes to identify nucleic acids of interest; this screening step can be performed before or after any recombination step. In some (but not all) shuffling embodiments, it is desirable to perform multiple rounds of recombination prior to selection to increase the diversity of the pool to be screened. The overall process of recombination and selection are optionally repeated recursively. Depending on context, shuffling can refer to an overall process of recombination and selection, or, alternately, can simply refer to the recombinational portions of the overall process.

Substantially identical: the phrase "substantially identical," in the context of two nucleic acid or protein sequences, refers to two or more sequences or subsequences that have at least 60%, preferably 80%, more preferably 90, even more preferably 95%, and most preferably at least 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In an especially preferred embodiment, the sequences are substantially identical over the entire length of the coding regions. Furthermore, substantially identical nucleic acid or protein sequences perform substantially the same function.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith &

Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., *J. Mol. Biol.* 215: 403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) *Laboratory Techniques in Biochemistry and Molecular Biology-Hybridization with Nucleic Acid* Probes part I chapter 2 "Overview of principles of hybridization and the strategy of nucleic acid probe assays" Elsevier, New York. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone homologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1%

SDS at 50° C., more desirably in 7% sodium dodecyl sulfate (SDS), 0.5 M NaPO₄, 1 mM EDTA at 50° C. with washing in 1×SSC, 0.1% SDS at 50° C., more desirably still in 7% sodium dodecyl sulfate (SDS), 0.5 M NaPO₄, 1 mM EDTA at 50° C. with washing in 0.5×SSC, 0.1% SDS at 50° C., preferably in 7% sodium dodecyl sulfate (SDS), 0.5 M NaPO₄, 1 mM EDTA at 50° C. with washing in 0.1×SSC, 0.1% SDS at 50° C., more preferably in 7% sodium dodecyl sulfate (SDS), 0.5 M NaPO₄, 1 mM EDTA at 50° C. with washing in 0.1× SSC, 0.1% SDS at 65° C.

A further indication that two nucleic acid sequences or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions.

"Synthetic" refers to a nucleotide sequence comprising structural characters that are not present in the natural sequence. For example, an artificial sequence that resembles more closely the G+C content and the normal codon distribution of dicot and/or monocot genes is said to be synthetic.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

The "Vip3 class of proteins" comprises Vip3A(a), Vip3A (b), Vip3A(c), Vip3B, Vip3C(a), Vip3C(b), Vip3Z, and their homologues. "Homologue" is used throughout to mean that the indicated protein or polypeptide bears a defined relationship to other members of the Vip3 class of proteins. This defined relationship includes but is not limited to, 1) proteins which are at least 70%, more preferably at least 80% and most preferably at least 90% identical at the sequence level to another member of the Vip3 class of proteins while also retaining pesticidal activity, 2) proteins which are cross-reactive to antibodies which immunologically recognize another member of the Vip3 class of proteins, 3) proteins which are cross-reactive with a receptor to another member of the Vip3 class of proteins and retain the ability to induce programmed cell death, and 4) proteins which are at least 70%, more preferably at least 80% and most preferably at least 90% identical at the sequence level to the toxic core region of another member of the Vip3 class of proteins while also retaining pesticidal activity. Other Vip3 homologues have been disclosed in WO 98/18932, WO 98/33991, WO 98/00546, and WO 99/57282.

Nucleotides are indicated by their bases by the following standard abbreviations: adenine (A), cytosine (C), thymine (T), and guanine (G) Amino acids are likewise indicated by the following standard abbreviations: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (H is; H), isoleucine (Ile; 1), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

DETAILED DESCRIPTION OF THE INVENTION

This invention relates to nucleic acid sequences whose expression results in novel toxins, and to the making and using of the toxins to control insect pests. The nucleic acid sequences are derived from *Bacillus*, a gram-positive spore-forming microorganism. In particular, novel Vip3 proteins, useful as pesticidal agents, are provided.

For purposes of the present invention, insect pests include insects selected from, for example, the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, and Trichoptera, particularly Lepidoptera.

Tables 1-7 give a list of pests associated with major crop plants. Such pests are included within the scope of the present invention.

TABLE 1

| Lepidoptera | |
|---|---|
| *Ostrinia nubilalis*, European corn borer | *Spodoptera frugiperda*, fall armyworm |
| *Agrotis ipsilon*, black cutworm | *Diatraea grandiosella*, southwestern corn borer |
| *Helicoverpa zea*, corn earworm | |
| *Elasmopalpus lignosellus*, lesser cornstalk borer | *Scirpophaga incertulas*, yellow stemborer |
| | *Chilo polychrysa*, darkheaded riceborer |
| *Diatraea saccharalis*, sugarcane borer | *Mythimna separata*, oriental armyworm |
| *Heliohtis virescens*, cotton bollworm | *Chilo partellus*, sorghum borer |
| *Spodoptera exigua*, beet armyworm | *Feltia subterranea*, granulate cutworm |
| *Pectinophora gossypiella*, pink bollworm | *Homoeosoma electellum*, sunflower head moth |
| *Scirpophaga innotata*, white stemborer | *Cochylis hospes*, banded sunflower moth |
| *Cnaphalocrocis medinalis*, leaffolder | *Pseudaletia unipunctata*, army worm |
| *Chilo plejadellus*, rice stalk borer | *Agrotis orthogonia*, pale western cutworm |
| *Nymphula depunctalis*, caseworm | *Pseudoplusia includens*, soybean looper |
| *Spodoptera litura*, cutworm | *Anticarsia gemmatalis*, velvetbean caterpillar |
| *Spodoptera mauritia*, rice swarming caterpillar | *Plathypena scabra*, green cloverworm |

TABLE 2

| Coleoptera | |
|---|---|
| *Diabrotica virgifera*, western corn rootworm | *Phyllophaga crinita*, white grub |
| *Diabrotica longicornis*, northern corn rootworm | *Melanotus* spp., Eleodes, Conoderus, and *Aeolus* spp., wireworms |
| *Diabrotica undecimpunctata*, southern corn rootworm | *Oulema melanopus*, cereal leaf beetle |
| *Cyclocephala borealis*, northern masked chafer (white grub) | *Chaetocnema pulicaria*, corn flea beetle |
| *Cyclocephala immaculata*, southern masked chafer (white grub) | *Oulema melanopus*, cereal leaf beetle |
| *Popillia japonica*, Japanese beetle | *Hypera punctata*, clover leaf weevil |
| *Chaetocnema pulicaria*, corn flea beetle | *Anthonomus grandis*, boll weevil |
| *Sphenophorus maidis*, maize billbug | *Colaspis brunnea*, grape colaspis |
| | *Lissorhoptrus oryzophilus*, rice water weevil |
| | *Sitophilus oryzae*, rice weevil |
| | *Epilachna varivestis*, Mexican bean beetle |

TABLE 3

| Homoptera | |
|---|---|
| *Rhopalosiphum maidis*, corn leaf aphid | *Anuraphis maidiradicis*, corn root aphid |
| *Sipha flava*, yellow sugarcane aphid | *Trialeurodes abutilonea*, bandedwinged whitefly |
| *Schizaphis graminum*, greenbug | *Nephotettix nigropictus*, rice leafhopper |
| *Macrosiphum avenae*, English grain aphid | *Myzus persicae*, green peach aphid |
| *Aphis gossypii*, cotton aphid | *Empoasca fabae*, potato leafhopper |
| *Pseudatomoscelis seriatus*, cotton fleahopper | |

TABLE 4

| Hemiptera | |
|---|---|
| *Blissus leucopterus leucopterus*, chinch bug | *Acrosternum hilare*, green stink bug |
| *Lygus lineolaris*, tarnished plant bug | *Euschistus servus*, brown stink bug |

TABLE 5

| Orthroptera |
|---|
| *Melanoplus femurrubrum*, redlegged grasshopper |
| *Melanoplus sanguinipes*, migratory grasshopper |
| *Melanoplus differentialis*, differential grasshopper |

TABLE 6

| Diptera | |
|---|---|
| *Hylemya platura*, seedcorn maggot | *Meromyza americana*, wheat stem maggot |
| *Agromyza parvicornis*, corn blotch leafminer | *Hylemya coarctata*, wheat bulb fly |
| *Contarinia sorghicola*, *sorghum* midge | *Neolasioptera murtfeldtiana*, sunflower seed midge |
| *Mayetiola destructor*, Hessian fly | |
| *Sitodiplosis mosellana*, wheat midge | |

TABLE 7

| Thysanoptera |
|---|
| *Anaphothrips obscurus*, grass thrips |
| *Frankliniella fusca*, tobacco thrips |
| *Thrips tabaci*, onion thrips |
| *Sericothrips variabilis*, soybean thrips |

The expression of the nucleic acid sequences of the present invention results in toxins that can be used to control lepidopteran insects, for example, without limitation, *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth).

In one preferred embodiment, the invention encompasses an isolated nucleic acid molecule comprising a nucleotide sequence that: (a) has a compliment that hybridizes to nucleotides 1981-2367 of SEQ ID NO: 1 in 7% sodium dodecyl sulfate (SDS), 0.5 M $NaPO_4$, 1 mM EDTA at 50° C. with washing in 0.1×SSC, 0.1% SDS at 65° C.; or (b) is isocoding with the nucleotide sequence of (a); or (c) comprises a consecutive 20 base pair nucleotide portion identical in sequence to a consecutive 20 base pair nucleotide portion of a nucleotide sequence of (a) or (b); or (d) has at least 93% sequence identity with SEQ ID NO: 1; or (e) encodes an amino acid sequence having at least 91% sequence identity with SEQ ID NO: 2, wherein expression of the isolated nucleic acid molecule results in insect control activity. When expressed in a heterologous host, the nucleic acid molecule of SEQ ID NO: 1, SEQ ID NO: 3, SEQ ID NO: 10, and SEQ ID NO: 31 results in insect control activity against *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth), showing that the nucleotide sequence set forth in SEQ ID NO: 1, SEQ ID NO: 3, SEQ ID NO: 10, and SEQ ID NO: 31 is sufficient for such insect control activity.

In one embodiment, the invention encompasses a nucleic acid molecule comprising a nucleotide sequence that has at least 75% sequence identity with nucleotides 1981-2367 of SEQ ID NO: 1. Preferably, the isolated nucleic acid molecule comprises a nucleotide sequence that has at least 85% sequence identity with nucleotides 1981-2367 of SEQ ID NO: 1. More preferably, the isolated nucleic acid molecule comprises a nucleotide sequence that has at least 95% sequence identity with nucleotides 1981-2367 of SEQ ID NO: 1. Even more preferably, the isolated nucleic acid molecule comprises a nucleotide sequence that has at least 99% sequence identity with nucleotides 1981-2367 of SEQ ID NO: 1. Most preferably, the isolated nucleic acid molecule comprises nucleotides 1981-2367 of SEQ ID NO: 1 or SEQ ID NO: 3.

In another embodiment, the invention encompasses a nucleic acid molecule comprising a nucleotide sequence that has at least 93% sequence identity with SEQ ID NO: 1. Preferably, the isolated nucleic acid molecule comprises a nucleotide sequence that has at least 95% sequence identity with SEQ ID NO: 1. More preferably, the isolated nucleic acid molecule comprises a nucleotide sequence that has at least 99% sequence identity with SEQ ID NO: 1. Most preferably, the isolated nucleic acid molecule comprises nucleotides 1-2367 of a nucleotide sequence selected from the group consisting of SEQ ID NO: 1, SEQ ID NO: 3, SEQ ID NO: 10, SEQ ID NO: 31, and SEQ ID NO: 33.

In yet another embodiment, the invention encompasses a nucleic acid molecule comprised in a *Bacillus thuringiensis* isolate selected from the group consisting of C1674, designated NRRL accession B-30556; and C536, designated NRRL accession B-30557. In a preferred embodiment, the invention encompasses a nucleic acid molecule comprised in an *E. coli* clone selected from the group consisting of pNOV3910, designated NRRL accession B-30553; pNOV3911, designated NRRL accession B-30552; pNOV3906, designated NRRL accession B-30555; pNOV3905, designated NRRL accession B-30554; and pNOV3912, designated NRRL accession B-30551, whose expression results in an insecticidal toxin.

The present invention also encompasses an isolated nucleic acid molecule which encodes a toxin comprising an amino acid sequence with at least 75% identity with amino acids 661-788 of the amino acid sequence of SEQ ID NO: 2. Preferably, the isolated nucleic acid molecule encodes a toxin comprising an amino acid sequence which has at least 85% identity with amino acids 661-788 of the amino acid sequence of SEQ ID NO: 2. More preferably, the isolated nucleic acid molecule encodes a toxin comprising an amino acid sequence which has at least 95% identity with amino acids 661-788 of the amino acid sequence of SEQ ID NO: 2. Even more preferably, the isolated nucleic acid molecule encodes a toxin comprising an amino acid sequence which has at least 99% identity with amino acids 661-788 of the amino acid sequence of SEQ ID NO: 2. Most preferably, the isolated nucleic acid molecule encodes a toxin comprising amino acids 661-788 of the amino acid sequence of SEQ ID NO: 2.

In another embodiment, the isolated nucleic acid molecule encodes a toxin comprising an amino acid sequence which has 91% identity to the amino acid sequence set forth in SEQ ID NO: 2. Preferably, the isolated nucleic acid molecule encodes a toxin comprising an amino acid sequence which has 95% identity to the amino acid sequence set forth in SEQ ID NO: 2. More preferably, the isolated nucleic acid molecule encodes a toxin comprising an amino acid sequence which has 99% identity to the amino acid sequence set forth in SEQ ID NO: 2. Most preferably, the isolated nucleic acid molecule encodes a toxin comprising the amino acid sequence set forth in SEQ ID NO: 2, SEQ ID NO: 11, or SEQ ID NO: 32.

The present invention also encompasses recombinant vectors comprising the nucleic acid sequences of this invention. In such vectors, the nucleic acid sequences are preferably comprised in expression cassettes comprising regulatory elements for expression of the nucleotide sequences in a transgenic host cell capable of expressing the nucleotide sequences. Such regulatory elements usually comprise promoter and termination signals and preferably also comprise elements allowing efficient translation of polypeptides encoded by the nucleic acid sequences of the present invention. Vectors comprising the nucleic acid sequences are usually capable of replication in particular host cells, preferably as extrachromosomal molecules, and are therefore used to amplify the nucleic acid sequences of this invention in the host cells.

In one embodiment, host cells for such vectors are microorganisms, such as bacteria, in particular *E. coli*. In another embodiment, host cells for such recombinant vectors are endophytes or epiphytes. A preferred host cell for such vectors is a eukaryotic cell, such as a yeast cell, a plant cell, or an insect cell. Plant cells such as maize cells or cotton are most preferred host cells. In another preferred embodiment, such vectors are viral vectors and are used for replication of the nucleotide sequences in particular host cells, e.g. insect cells or plant cells. Recombinant vectors are also used for transformation of the nucleotide sequences of this invention into transgenic host cells, whereby the nucleotide sequences are stably integrated into the DNA of such transgenic host cells. In one, such transgenic host cells are prokaryotic cells. In a preferred embodiment, such transgenic host cells are eukaryotic cells, such as yeast cells, insect cells, or plant cells. In a most preferred embodiment, the transgenic host cells are plant cells, such as maize cells or cotton cells.

In yet another aspect, the present invention provides toxins produced by the expression of the nucleic acid molecules of the present invention.

In preferred embodiments, the insecticidal toxins of the invention comprise a polypeptide encoded by a nucleotide sequence of the invention. In a further preferred embodiment, the toxin is produced by a *Bacillus thuringiensis* isolated selected from the group consisting of C1674, designated NRRL accession B-30556; and C536, designated NRRL accession B-30557.

In another embodiment, the toxins are produced by an *E. coli* clone selected from the group consisting of pNOV3910, designated NRRL accession B-30553; pNOV3911, designated NRRL accession B-30552; pNOV3906, designated NRRL accession B-30555; pNOV3905, designated NRRL accession B-30554; and pNOV3912, designated NRRL accession B-30551. In a preferred embodiment, the toxin is produced by the expression of the nucleic acid molecule comprising nucleotides 1-2367 of SEQ ID NO: 1 or nucleotides 1-2367 of SEQ ID NO: 3, or nucleotides 1-2367 of SEQ ID NO: 10, or nucleotides 1-2367 of SEQ ID NO: 31.

The present invention encompasses a toxin which comprises an amino acid sequence which has at least 75% identity with amino acids 661-788 of the amino acid sequence of SEQ ID NO: 2. Preferably, the toxin comprises an amino acid sequence which has at least 85% identity with amino acids 661-788 of the amino acid sequence of SEQ ID NO: 2. Even more preferably, the toxin comprises an amino acid sequence which has at least 95% identity with amino acids 661-788 of the amino acid sequence of SEQ ID NO: 2. Even more preferably, the toxin comprises an amino acid sequence which has at least 99% identity with amino acids 661-788 of the amino acid sequence of SEQ ID NO: 2. Most preferably, the toxin comprises amino acids 661-788 of SEQ ID NO: 2.

In another preferred embodiment, a toxin of the present invention comprises an amino acid sequence which has at least 91% identity with the amino acid sequence set forth in SEQ ID NO: 2. Preferably, the toxin comprises an amino acid sequence which has at least 95% identity with the amino acid sequence set forth in SEQ ID NO: 2. More preferably, the toxin comprises an amino acid sequence which has at least 99% identity with the amino acid sequence set forth in SEQ ID NO: 2. Most preferably, the toxin comprises the amino acid sequence set forth in SEQ ID NO: 2, SEQ ID NO: 11, or SEQ ID NO: 32.

The toxins of the present invention have insect control activity when tested against insect pests in bioassays. In another preferred embodiment, the toxins of the invention are active against lepidopteran insects, preferably against *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth). The insect controlling properties of the insecticidal toxins of the invention are further illustrated in Examples 6, 8, 9 and 13.

The present invention also encompasses hybrid toxins which are active against insects, wherein the hybrid toxins are encoded by nucleic acid molecules comprising a nucleotide sequence that: (a) has a compliment that hybridizes to nucleotides 1981-2367 of SEQ ID NO: 1 in 7% sodium dodecyl sulfate (SDS), 0.5 M $NaPO_4$, 1 mM EDTA at 50° C. with washing in 0.1×SSC, 0.1% SDS at 65° C.; or (b) is isocoding with the nucleotide sequence of (a); or (c) comprises a consecutive 20 base pair nucleotide portion identical in sequence to a consecutive 20 base pair nucleotide portion of a nucleotide sequence of (a) or (b), wherein expression of the nucleic acid molecule results in insect control activity. In a preferred embodiment, the hybrid toxin is encoded by the approximately 2.4 kb DNA fragment comprised in pNOV3912, deposited in the *E. coli* strain DH5α designated NRRL accession B-30551, whose expression results in an insecticidal hybrid toxin. Specifically exemplified herein is a hybrid toxin that is encoded by the nucleotide sequence set forth in SEQ ID NO: 10. When expressed in a heterologous host, the nucleic acid molecule of SEQ ID NO: 10 results in insect control activity against *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth). The insect controlling properties of the exemplified hybrid toxin of the invention is further illustrated in Example 9.

The present invention also encompasses hybrid toxins active against insects that comprise a carboxy-terminal region of a Vip3 toxin joined in the amino to carboxy direction to an amino-terminal region of a different Vip3 toxin, wherein the carboxy-terminal region comprises an amino acid sequence which has at least 75% identity, preferably at least 85% identity, more preferably at least 95% identity, most preferably at least 99% identity, with amino acids 661-788 of SEQ ID NO: 2; and wherein the amino-terminal region has at least 75% identity, preferably at least 85% identity, more preferably at least 95% identity, most preferably at least 99% identity, with amino acids 1-660 of SEQ ID NO: 5. In a preferred embodiment, the carboxy-terminal region comprises amino acids 661-788 of SEQ ID NO: 2, and the amino-terminal region comprises amino acids 1-660 of SEQ ID NO: 65 In a more preferred embodiment, the hybrid toxin comprises amino acids 1-788 of SEQ ID NO: 11.

In further embodiments, the nucleotide sequences of the invention can be modified by incorporation of random mutations in a technique known as in vitro recombination or DNA shuffling. This technique is described in Stemmer et al., Nature 370:389-391 (1994) and U.S. Pat. No. 5,605,793, which are incorporated herein by reference. Millions of mutant copies of a nucleotide sequence are produced based on an original nucleotide sequence of this invention and variants with improved properties, such as increased insecticidal activity, enhanced stability, or different specificity or range of target insect pests are recovered. The method encompasses forming a mutagenized double-stranded polynucleotide from a template double-stranded polynucleotide comprising a nucleotide sequence of this invention, wherein the template double-stranded polynucleotide has been cleaved into double-stranded-random fragments of a desired size, and comprises the steps of adding to the resultant population of double-stranded random fragments one or more single or double-stranded oligonucleotides, wherein said oligonucleotides comprise an area of identity and an area of heterology to the double-stranded template polynucleotide; denaturing the resultant mixture of double-stranded random fragments and oligonucleotides into single-stranded fragments; incubating the resultant population of single-stranded fragments with a polymerase under conditions which result in the annealing of said single-stranded fragments at said areas of identity to form pairs of annealed fragments, said areas of identity being sufficient for one member of a pair to prime replication of the other, thereby forming a mutagenized double-stranded polynucleotide; and repeating the second and third steps for at least two further cycles, wherein the resultant mixture in the second step of a further cycle includes the mutagenized double-stranded polynucleotide from the third step of the previous cycle, and the further cycle forms a further mutagenized double-stranded polynucleotide. In a preferred embodiment, the concentration of a single species of double-stranded random fragment in the population of double-stranded random fragments is less than 1% by weight of the total DNA. In a further preferred embodiment, the template double-stranded polynucleotide comprises at least about 100 species of polynucleotides. In another preferred embodiment, the size of the double-stranded random fragments is from about 5 by to 5 kb. In a further preferred embodiment, the fourth step of the method comprises repeating the second and the third steps for at least 10 cycles.

Expression of the Nucleotide Sequences in Heterologous Microbial Hosts

As biological insect control agents, the insecticidal toxins are produced by expression of the nucleotide sequences in heterologous host cells capable of expressing the nucleotide sequences. In a first embodiment, *B. thuringiensis* cells comprising modifications of a nucleotide sequence of this invention are made. Such modifications encompass mutations or deletions of existing regulatory elements, thus leading to altered expression of the nucleotide sequence, or the incorporation of new regulatory elements controlling the expression of the nucleotide sequence. In another embodiment, additional copies of one or more of the nucleotide sequences are added to *Bacillus thuringiensis* cells either by insertion into the chromosome or by introduction of extrachromosomally replicating molecules containing the nucleotide sequences.

In another embodiment, at least one of the nucleotide sequences of the invention is inserted into an appropriate expression cassette, comprising a promoter and termination signals. Expression of the nucleotide sequence is constitutive, or an inducible promoter responding to various types of stimuli to initiate transcription is used. In a preferred embodiment, the cell in which the toxin is expressed is a microorganism, such as a virus, a bacteria, or a fungus. In a preferred embodiment, a virus, such as a baculovirus, contains a nucleotide sequence of the invention in its genome and expresses large amounts of the corresponding insecticidal toxin after infection of appropriate eukaryotic cells that are suitable for virus replication and expression of the nucleotide sequence. The insecticidal toxin thus produced is used as an insecticidal agent. Alternatively, baculoviruses engineered to include the nucleotide sequence are used to infect insects in vivo and kill them either by expression of the insecticidal toxin or by a combination of viral infection and expression of the insecticidal toxin.

Bacterial cells are also hosts for the expression of the nucleotide sequences of the invention. In a preferred embodiment, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera *Agrobacterium, Alcaligenes, Azospirillum, Azotobacter, Bacillus, Clavibacter, Enterobacter, Erwinia, Flavobacter, Klebsiella, Pseudomonas, Rhizobium, Serratia, Streptomyces* and *Xanthomonas*. Symbiotic fungi, such as *Trichoderma* and *Gliocladium* are also possible hosts for expression of the inventive nucleotide sequences for the same purpose.

Techniques for these genetic manipulations are specific for the different available hosts and are known in the art. For example, the expression vectors pKK223-3 and pKK223-2 can be used to express heterologous genes in *E. coli*, either in transcriptional or translational fusion, behind the tac or trc promoter. For the expression of operons encoding multiple ORFs, the simplest procedure is to insert the operon into a vector such as pKK223-3 in transcriptional fusion, allowing the cognate ribosome binding site of the heterologous genes to be used. Techniques for overexpression in gram-positive species such as *Bacillus* are also known in the art and can be used in the context of this invention (Quax et al. In: Industrial Microorganisms: Basic and Applied Molecular Genetics, Eds. Baltz et al., American Society for Microbiology, Washington (1993)). Alternate systems for overexpression rely for example, on yeast vectors and include the use of *Pichia, Saccharomyces* and *Kluyveromyces* (Sreekrishna, In: Industrial microorganisms: basic and applied molecular genetics, Baltz, Hegeman, and Skatrud eds., American Society for Microbiology, Washington (1993); Dequin & Bane, Biotechnology L2:173-177 (1994); van den Berg et al., Biotechnology 8:135-139 (1990)).

Plant Transformation

In a particularly preferred embodiment, at least one of the insecticidal toxins of the invention is expressed in a higher organism, e.g., a plant. In this case, transgenic plants expressing effective amounts of the toxins protect themselves from insect pests. When the insect starts feeding on such a transgenic plant, it also ingests the expressed toxins. This will deter the insect from further biting into the plant tissue or may even harm or kill the insect. A nucleotide sequence of the present invention is inserted into an expression cassette, which is then preferably stably integrated in the genome of said plant. In another preferred embodiment, the nucleotide sequence is included in a non-pathogenic self-replicating virus. Plants transformed in accordance with the present invention may be monocots or dicots and include, but are not limited to, maize, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugar beet, sunflower, rapeseed, clover, tobacco, carrot, cotton, alfalfa, rice, potato, eggplant, cucumber, *Arabidopsis*, and woody plants such as coniferous and deciduous trees.

Once a desired nucleotide sequence has been transformed into a particular plant species, it may be propagated in that species or moved into other varieties of the same species, particularly including commercial varieties, using traditional breeding techniques.

A nucleotide sequence of this invention is preferably expressed in transgenic plants, thus causing the biosynthesis of the corresponding toxin in the transgenic plants. In this way, transgenic plants with enhanced resistance to insects are generated. For their expression in transgenic plants, the nucleotide sequences of the invention may require modification and optimization. Although in many cases genes from microbial organisms can be expressed in plants at high levels without modification, low expression in transgenic plants may result from microbial nucleotide sequences having codons that are not preferred in plants. It is known in the art that all organisms have specific preferences for codon usage, and the codons of the nucleotide sequences described in this invention can be changed to conform with plant preferences, while maintaining the amino acids encoded thereby. Furthermore, high expression in plants is best achieved from coding sequences that have at least about 35% GC content, preferably more than about 45%, more preferably more than about 50%, and most preferably more than about 60%. Microbial nucleotide sequences that have low GC contents may express poorly in plants due to the existence of ATTTA motifs that may destabilize messages, and AATAAA motifs that may cause inappropriate polyadenylation. Although preferred gene sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17:477-498 (1989)). In addition, the nucleotide sequences are screened for the existence of illegitimate splice sites that may cause message truncation. All changes required to be made within the nucleotide sequences such as those described above are made using well known techniques of site directed mutagenesis, PCR, and synthetic gene construction using the methods described in the published patent applications EP 0 385 962 (to Monsanto), EP 0 359 472 (to Lubrizol, and WO 93/07278 (to Ciba-Geigy).

In one embodiment of the invention synthetic genes are made according to the procedure disclosed in U.S. Pat. No. 5,625,136, herein incorporated by reference. In this procedure, maize preferred codons, i.e., the single codon that most frequently encodes that amino acid in maize, are used. The maize preferred codon for a particular amino acid can be derived, for example, from known gene sequences from maize. Maize codon usage for 28 genes from maize plants is found in Murray et al., Nucleic Acids Research 17:477-498 (1989), the disclosure of which is incorporated herein by reference. Specifically exemplified synthetic sequences of the present invention made with maize optimized codons are set forth in SEQ ID NO: 3 and SEQ ID NO: 33.

In this manner, the nucleotide sequences can be optimized for expression in any plant. It is recognized that all or any part of the gene sequence may be optimized or synthetic. That is, synthetic or partially optimized sequences may also be used.

For efficient initiation of translation, sequences adjacent to the initiating methionine may require modification. For example, they can be modified by the inclusion of sequences known to be effective in plants. Joshi has suggested an appropriate consensus for plants (NAR 15:6643-6653 (1987)) and Clonetech suggests a further consensus translation initiator (1993/1994 catalog, page 210). These consensuses are suitable for use with the nucleotide sequences of this invention. The sequences are incorporated into constructions comprising the nucleotide sequences, up to and including the ATG (whilst leaving the second amino acid unmodified), or alternatively up to and including the GTC subsequent to the ATG (with the possibility of modifying the second amino acid of the transgene).

The novel vip3 toxin genes of the present invention, either as their native sequence or as optimized synthetic sequences as described above, can be operably fused to a variety of promoters for expression in plants including constitutive, inducible, temporally regulated, developmentally regulated, chemically regulated, tissue-preferred and tissue-specific promoters to prepare recombinant DNA molecules, i.e., chimeric genes. The choice of promoter will vary depending on the temporal and spatial requirements for expression, and also depending on the target species. Thus, expression of the nucleotide sequences of this invention in leaves, in stalks or stems, in ears, in inflorescences (e.g. spikes, panicles, cobs, etc.), in roots, and/or seedlings is preferred. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell.

Preferred constitutive promoters include the CaMV 35S and 19S promoters (Fraley et al., U.S. Pat. No. 5,352,605 issued Oct. 4, 1994). An additionally preferred promoter is derived from any one of several of the actin genes, which are expressed in most cell types. The promoter expression cassettes described by McElroy et al. (Mol. Gen. Genet. 231: 150-160 (1991)) can be easily modified for the expression of the novel toxin gene and are particularly suitable for use in monocotyledonous hosts.

Yet another preferred constitutive promoter is derived from ubiquitin, which is another gene product known to accumulate in many cell types. A ubiquitin promoter has been cloned from several species for use in transgenic plants, for example, sunflower (Binet et al., 1991. Plant Science 79: 87-94), maize (Christensen et al., 1989. Plant Molec. Biol. 12: 619-632), and *arabidopsis* (Norris et al. 1993. Plant Molec. Biol. 21:895-906). The maize ubiquitin promoter has been developed in transgenic monocot systems and its sequence and vectors constructed for monocot transformation are disclosed in the patent publication EP 0 342 926. The ubiquitin promoter is suitable for the expression of the novel toxin gene in transgenic plants, especially monocotyledons.

Tissue-specific or tissue-preferential promoters useful for the expression of the novel toxin genes of the invention in plants, particularly maize, are those that direct expression in root, pith, leaf or pollen. Such promoters are disclosed in WO 93/07278, herein incorporated by reference in its entirety. Other tissue specific promoters useful in the present invention include the cotton rubisco promoter disclosed in U.S. Pat. No. 6,040,504; the rice sucrose synthase promoter disclosed in U.S. Pat. No. 5,604,121; and the cestrum yellow leaf curling virus promoter disclosed in WO 01/73087, all incorporated by reference. Chemically inducible promoters useful for directing the expression of the novel toxin gene in plants are disclosed in U.S. Pat. No. 5,614,395 herein incorporated by reference in its entirety.

The nucleotide sequences of this invention can also be expressed under the regulation of promoters that are chemically regulated. This enables the Vip3 toxins to be synthesized only when the crop plants are treated with the inducing chemicals. Preferred technology for chemical induction of gene expression is detailed in the published application EP 0 332 104 (to Ciba-Geigy) and U.S. Pat. No. 5,614,395. A preferred promoter for chemical induction is the tobacco PR-1a promoter.

A preferred category of promoters is that which is wound inducible. Numerous promoters have been described which are expressed at wound sites and also at the sites of phytopathogen infection. Ideally, such a promoter should only be active locally at the sites of infection, and in this way the insecticidal toxins only accumulate in cells that need to synthesize the insecticidal toxins to kill the invading insect pest. Preferred promoters of this kind include those described by Stanford et al. Mol. Gen. Genet. 215:200-208 (1989), Xu et al. Plant Molec. Biol. 22:573-588 (1993), Logemann et al. Plant Cell 1:151-158 (1989), Rohrmeier & Lehle, Plant Molec. Biol. 22:783-792 (1993), Firek et al. Plant Molec. Biol. 22:129-142 (1993), and Warner et al. Plant J. 3:191-201 (1993).

Preferred tissue specific expression patterns include green tissue specific, root specific, stem specific, and flower specific. Promoters suitable for expression in green tissue include many that regulate genes involved in photosynthesis and many of these have been cloned from both monocotyledons and dicotyledons. A preferred promoter is the maize PEPC promoter from the phosphoenol carboxylase gene (Hudspeth & Grula, Plant Molec. Biol. 12:579-589 (1989)). A preferred promoter for root specific expression is that described by de Framond (FEBS 290:103-106 (1991); EP 0 452 269 to Ciba-Geigy). A preferred stem specific promoter is that described in U.S. Pat. No. 5,625,136 (to Ciba-Geigy) and which drives expression of the maize trpA gene.

Further preferred embodiments are transgenic plants expressing the nucleotide sequences in a wound-inducible or pathogen infection-inducible manner.

In addition to the selection of a suitable promoter, constructions for expression of an insecticidal toxin in plants require an appropriate transcription terminator to be attached downstream of the heterologous nucleotide sequence. Several such terminators are available and known in the art (e.g. tml from CaMV, E9 from rbcS). Any available terminator known to function in plants can be used in the context of this invention.

Numerous other sequences can be incorporated into expression cassettes described in this invention. These include sequences that have been shown to enhance expression such as intron sequences (e.g. from Adhl and bronzel) and viral leader sequences (e.g. from TMV, MCMV and AMV).

It may be preferable to target expression of the nucleotide sequences of the present invention to different cellular localizations in the plant. In some cases, localization in the cytosol may be desirable, whereas in other cases, localization in some subcellular organelle may be preferred. Subcellular localization of transgene-encoded enzymes is undertaken using techniques well known in the art. Typically, the DNA encoding the target peptide from a known organelle-targeted gene product is manipulated and fused upstream of the nucleotide sequence. Many such target sequences are known for the chloroplast and their functioning in heterologous constructions has been shown. The expression of the nucleotide sequences of the present invention is also targeted to the endoplasmic reticulum or to the vacuoles of the host cells. Techniques to achieve this are well known in the art.

Numerous transformation vectors available for plant transformation are known to those of ordinary skill in the plant transformation art, and the nucleic acid molecules of the invention can be used in conjunction with any such vectors. The selection of vector will depend upon the preferred transformation technique and the target plant species for transformation. For certain target species, different antibiotic or herbicide selection markers may be preferred. Selection markers used routinely in transformation include the nptII gene, which confers resistance to kanamycin and related antibiotics (Messing & Vierra., 1982. Gene 19: 259-268; and Bevan et al., 1983. Nature 304:184-187), the bar gene, which confers resistance to the herbicide phosphinothricin (White et al., 1990. Nucl. Acids Res 18: 1062, and Spencer et al., 1990. Theor. Appl. Genet. 79: 625-631), the hph gene, which confers resistance to the antibiotic hygromycin (Blochinger & Diggelmann, Mol Cell Biol 4: 2929-2931), and the dhfr gene, which confers resistance to methatrexate (Bourouis et al., 1983. EMBO J. 2(7): 1099-1104), the EPSPS gene, which confers resistance to glyphosate (U.S. Pat. Nos. 4,940,935 and 5,188,642), and the mannose-6-phosphate isomerase gene, which provides the ability to metabolize mannose (U.S. Pat. Nos. 5,767,378 and 5,994,629). The choice of selectable marker is not, however, critical to the invention.

In another preferred embodiment, a nucleotide sequence of the present invention is directly transformed into the plastid genome. A major advantage of plastid transformation is that plastids are generally capable of expressing bacterial genes without substantial modification, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et al. (1994) Proc. Natl. Acad. Sci. USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps 12 genes conferring resistance to spectinomycin and/or streptomycin are utilized as selectable markers for transformation (Svab, Z., Hajdukiewicz, P., and Maliga, P. (1990) Proc. Natl. Acad. Sci. USA 87, 8526-8530; Staub, J. M., and Maliga, P. (1992) Plant Cell 4, 39-45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) EMBO J. 12, 601-606). Substantial increases in transformation frequency are obtained by replacement of the recessive rRNA or r-protein antibiotic resistance genes with a dominant selectable marker, the bacterial aadA gene encoding the spectinomycin-cletoxifying enzyme aminoglycoside-3'-adenyltransferase (Svab, Z., and Maliga, P. (1993) Proc. Natl. Acad. Sci. USA 90, 913-917). Previously, this marker had been used successfully for high-frequency transformation of the plastid genome of the green alga *Chlamydomonas reinhardtii* (Goldschmidt-Clermont, M. (1991) Nucl. Acids Res. 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleotide sequence of the present invention is inserted into a plastid-targeting vector and transformed into the plastid genome of a desired plant host. Plants homoplastic for plastid genomes containing a nucleotide sequence of the present invention are obtained, and are preferentially capable of high expression of the nucleotide sequence.

Combinations of Insect Control Principles

The pesticidal toxins of the invention can be used in combination with Bt δ-endotoxins or other pesticidal principles to increase pest target range. Furthermore, the use of the pesticidal toxins of the invention in combination with Bt δ-endotoxins or other pesticidal principles of a distinct nature has particular utility for the prevention and/or management of insect resistance.

The various insecticidal crystal proteins from *Bacillus thuringiensis* have been classified based upon their spectrum of activity and sequence similarity. The classification put forth by Hofte and Whiteley, Microbiol. Rev. 53: 242-255 (1989) placed the then known insecticidal crystal proteins into four major classes. Generally, the major classes are defined by the spectrum of activity, with the Cry1 proteins active against Lepidoptera, Cry2 proteins active against both Lepidoptera and Diptera, Cry3 proteins active against Coleoptera, and Cry4 proteins active against Diptera.

Within each major class, the δ-endotoxins are grouped according to sequence similarity. The Cry1 proteins are typically produced as 130-140 kDa protoxin proteins that are proteolytically cleaved to produce active toxins that are about 60-70 kDa. The active portion of the δ-endotoxin resides in the $NH_2$-terminal portion of the full-length molecule. Hofte and Whiteley, supra, classified the then known Cry1 proteins into six groups, 1Aa, 1Ab, 1Ac, 1B, 1C, and 1D. Since then, proteins classified as Cry1Ea, Cry1Fa, Cry9A, Cry9C and Cry9B, as well as others, have also been characterized.

The spectrum of insecticidal activity of an individual δ-endotoxin from *Bacillus thuringiensis* tends to be quite narrow, with a given δ-endotoxin being active against only a few insects. Specificity is the result of the efficiency of the various steps involved in producing an active toxin protein and its subsequent ability to interact with the epithelial cells in the insect digestive tract. In one preferred embodiment, expression of the nucleic acid molecules of the invention in transgenic plants is accompanied by the expression of one or more Bt δ-endotoxins. Particularly preferred Bt δ-endotoxins are those disclosed in U.S. Pat. No. 5,625,136, herein incorporated by reference.

It is well known that many δ-endotoxin proteins from *Bacillus thuringiensis* are actually expressed as protoxins. These protoxins are solubilized in the alkaline environment of the insect gut and are proteolytically converted by proteases into a toxic core fragment (Hofte and Whiteley, Microbiol. Rev. 53: 242-255 (1989)). For δ-endotoxin proteins of the Cry1 class, the toxic core fragment is localized in the N-terminal half of the protoxin. It is within the scope of the present invention that genes encoding either the full-length protoxin form or the truncated toxic core fragment of the novel toxin proteins can be used in plant transformation vectors to confer insecticidal properties upon the host plant.

Other insecticidal principles include protease inhibitors (both serine and cysteine types), lectins, α-amylase, peroxidase and cholesterol oxidase. Other Vip genes, such as vip1A (a) and vip2A(a) as disclosed in U.S. Pat. No. 5,849,870 and herein incorporated by reference, are also useful in the present invention.

This co-expression of more than one insecticidal principle in the same transgenic plant can be achieved by genetically engineering a plant to contain and express all the genes necessary. Alternatively, a plant, Parent 1, can be genetically engineered for the expression of genes of the present invention. A second plant, Parent 2, can be genetically engineered for the expression of a supplemental insect control principle. By crossing Parent 1 with Parent 2, progeny plants are obtained which express all the genes introduced into Parents 1 and 2.

The present invention further encompasses variants of the disclosed nucleic acid molecules. Naturally occurring variant sequences can be identified and/or isolated with the use of well-known molecular biology techniques, as, for example, with PCR and hybridization techniques as outlined below.

Variant vip3 nucleotide sequences include synthetically derived nucleotide sequences, such as those generated, for example, by using site-directed mutagenesis or those made by whole domain swaps, but which still exhibit pesticidal activity. Methods for mutagenesis and nucleotide sequence alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Generally, a nucleotide sequence of the invention will have at least 80%, preferably 85%, 90%, 95%, up to 98% or more sequence identity to its respective reference vip3 nucleotide sequence, and have pesticidal activity.

Variant vip3 nucleotide sequences also encompass sequences derived from a mutagenic and recombinogenic procedure such as DNA shuffling. With such a procedure, one or more different vip3 sequences of the present invention, for example, without limitation, vip3C(a), vip3C(b), vip3A-C, and vip3C-12168 can be recombined together or with other vip3 or related sequences, for example, without limitation, vip3A (SEQ ID NO: 4), vip3B (SEQ ID NO: 6), and vip3Z (SEQ ID NO: 8), to create new vip3 nucleic acid molecules encoding Vip3 toxins possessing the desired properties. In this manner, libraries of recombinant vip3 polynucleotides are generated from a population of sequence related vip3 polynucleotides comprising sequence regions that have substantial sequence identity and can be homologously recombined in vitro or in vivo. Strategies for such DNA shuffling are known in the art. See, for example, Stemmer (1994) Proc. Natl. Acad. Sci. USA 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) Proc. Natl. Acad. Sci. USA 94:4504-4509; Crameri et al. (1998) Nature 391:288-291; International Patent Application WO 99/57128, and U.S. Pat. Nos. 5,605,793, 5,837,458 and 6,335,179.

Mutagenesis methods as disclosed herein can be combined with high-throughput, screening methods to detect the pesticidal activity of cloned, mutagenized Vip3 polypeptides in host cells. Mutagenized DNA molecules that encode active Vip3 polypeptides (e.g., secreted and detected by antibodies; or insecticidal in an insect bioassay) can be recovered from the host cells and rapidly sequenced using standard art procedures. These methods allow the rapid determination of the importance of individual amino acid residues in a Vip3 polypeptide of interest, and can be applied to polypeptides of unknown structure.

The libraries of recombinant vip3 genes that are produced using DNA shuffling methods are screened to identify those that exhibit improved properties for use in protecting plants against pests. Included among properties for which DNA shuffling is useful for obtaining improved vip3 pest resistance genes are increased potency against a target pest, increased target pest range, decreased susceptibility to development of resistance by pests, increased expression level, increased resistance to protease degradation, increased stability in environmental conditions, and reduced toxicity to a host plant. By using an appropriate screening strategy, one can simultaneously or sequentially obtain vip3 genes that are optimized for more than one property.

DNA shuffling is useful for obtaining vip3 pest resistance genes that encode toxins that exhibit enhanced potency against a target pest. Once the shuffling is completed, the resulting library of shuffled vip3 genes is screened to identify those that exhibit enhanced pesticidal activity. One way of performing this screening is to clone the protein-coding region of the shuffled vip3 genes into an expression vector that is suitable for expressing the genes in a chosen host cell such as, for example, *E. coli* or a crystal minus strain of *Bacillus thuringiensis*. One skilled in the art will recognize the advantages and disadvantages of using either of these two expression systems. For example, *Bacillus thuringiensis* would be more desirable in producing secreted Vip3 proteins. If desired, clones can be subjected to a preliminary screen, for example, by immunoassay, to identify those that produce a Vip3 protein of the correct size. Those that are positive in the preliminary screen are then tested in a functional screen to identify shuffled vip3 genes that encode a toxin having the desired enhanced activity.

A whole insect assay can be used for determining toxicity. In these assays, the Vip3 toxins expressed from the shuffled vip3 genes are placed on insect diet, for example, artificial diet or plant tissue, and consumed by the target insect. Those clones causing growth inhibition or mortality to the target insect can be tested in further bioassays to determine potency. Shuffled vip3 genes encoding toxins with enhanced potency can be identified as those that have a decreased $EC_{50}$ (concentration of toxin necessary to reduce insect growth by 50%) and/or $LC_{50}$ (concentration of toxin necessary to cause 50% mortality).

In vitro assays can also be used for screening shuffled vip3 gene libraries. Such assays typically involve the use of cultured insect cells that are susceptible to Vip3 toxins, and/or cells that express a receptor for the Vip3 toxins, either naturally or as a result of expression of a heterologous gene. Other in vitro assays can be used, for example, detection of morphological changes in cells, dyes and labels useful for detecting cell death, or detection of the release of ATPase by cells. One example of a suitable in vitro assay using cultured insect cells for Vip3 toxicity is Sf9 (*Spodoptera frugiperda*) cells. Sf9 is highly sensitive to Vip3 toxins. When Vip3 toxins are mixed with Sf9 cells, the cell membrane becomes highly permeable to small molecules. When a dye such as trypan blue is added to the cell suspension, those cells which are killed by the Vip3 toxin are stained blue. Thus, the cytotoxicity of the Vip3 toxin can be determined by image analysis.

Additional in vitro assays involve the use of receptors for the Vip3 toxins. One such receptor is disclosed in U.S. Pat. No. 6,291,156, herein incorporated by reference. The Vip3 receptor protein can be immobilized on a receiving surface, for example, without limitation, a 96-well plate or a nitrocellulose membrane, and exposed to clones comprising shuffled vip3 genes. Thus, shuffled vip3 genes that encode functional toxins can be identified on the basis of binding affinity to the Vip3 receptor. Further, the gene encoding the Vip3 receptor can be transformed into a non-Vip3 susceptible cell line, for example the Schneider 2 (S2) *Drosophila* cell line, using methods known in the art (see for example, Clem and Miller, 1194, Mol. Cel. Biol. 14:5212-522). The transformed S2 cells can then be exposed to clones comprising shuffled vip3 genes. Thus, shuffled vip3 genes that encode functional toxins can be identified on the basis of induction of cell death.

EXAMPLES

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel (ed.), Current Protocols in Molecular Biology, John Wiley and Sons, Inc. (1994); J. Sambrook, et al., Molecular Cloning: *A Laboratory Manual*, 3d Ed., Cold Spring Harbor, N.Y.: Cold Spring Harbor Laboratory Press (2001); and by T. J. Silhavy, M. L. Berman, and L. W. Enquist, Experiments with Gene Fusions, Cold Spring Harbor Laboratory, Cold Spring Harbor, N.Y. (1984).

Example 1

Identification of Bt Isolates That Harbor Vip3 Homologous Proteins

Three sets of PCR primers, whose sequences are based on the vip3A gene (SEQ ID NO: 5), were used in a PCR reaction to amplify fragments of possible homologous vip3 genes from *Bacillus thuringiensis* (Bt) isolates. The three primer sets used were:

```
                                     (SEQ ID NO: 12)
1F: 5'-ATGAACAAGAATAATACTAAATTAAGCACAAGAGCC-3'

(SEQ ID NO: 13)
1R: 5'-CTCAACATAGAGGTAATTTTAGGTAGATATACCCG-3'

(SEQ ID NO: 14)
p3: 5'-GATGATGGGTGTATATGCCGTTAG-3'

(SEQ ID NO: 15)
p4: 5'-AATAAATTGTGAAATTCCTCCGTCC-3'

(SEQ ID NO: 16)
4F: 5'-AGTCAAAATGGAGATCAAGGTTGGGGAGATAAC-3'

(SEQ ID NO: 17)
4R: 5'-TTACTTAATAGAGAGATCGTGGAAATGTACAATA-3'
```

Three PCR products were expected if a Bt isolate comprised a gene identical to the vip3A gene (SEQ ID NO: 4). The size of the PCR product generated by primer sets 1F/1R, p3/p4, and 4F/4R were 377 bp, 344 bp, and 419 bp, respectively. Isolates that produced only one or two PCR products, which indicated they may comprise a vip3 gene with some sequence difference to vip3A, were subjected to further sequence analysis.

Example 2

Cloning and Sequencing of PCR Products to Confirm Vip3 Homologous Sequences Bt isolates identified in Example 1 as producing one or two PCR products were subjected to PCR again with primer set 1F/1R (SEQ ID NO: 12/SEQ ID NO: 13) as well as the following two primers:

```
                                     (SEQ ID NO: 18)
p5: 5'- AATGGAGATGAAGCTTGGGGAGAT-3'

(SEQ ID NO: 19)
p6: 5'-CGTGGAAATGTACAATAGGACCACC-3'
```

The PCR products were then cloned into a pCR2.1-Topo (Invitrogen) vector and sequenced using standard art procedures.

Three Bt isolates were identified as comprising homologous vip3 genes, designated vip3C, with significant sequence differences to vip3A. These Bt isolates were designated C536, C1674 and AB727.

Example 3

PCR Cloning the Full-Length vip3C Gene

The 3' end of the vip3C gene was obtained by PCR using total plasmid DNA isolated from Bt strain C536 or C1674 as the template. The primers used were:

```
                                     (SEQ ID NO: 20)
Vip3CF4: 5'-GTTTAGAAGATTTTCAAACCATTAC-3'

(SEQ ID NO: 21)
T7: 5'-TTAATACGACTCACTATAGGG-3'
```

Primer T7 is a non-gene specific primer that recognizes the flanking nucleotide sequence 3' to the vip3C gene.

The PCR products were cloned and sequenced using standard art procedures. The final full-length vip3C gene was obtained by PCR using the two primers located at the 3' and 5' ends of vip3C:

```
                                     (SEQ ID NO: 22)
Vip3Cc: 5'-TTTATTTAATAGAAACGTTTTCAAATGATATATG-3'

(SEQ ID NO: 23)
Vip3Cn: 5'-CACCATGAACAAGAATAATACTAAATTAAGCACAAGAG-3'
```

Two full-length vip3C genes were obtained. The vip3C gene from Bt isolate C536 was designated vip3C(a), and the vip3C gene isolated from C1674 was designated vip3C(b). Vip3C(a) and vip3C(b) differ by one nucleotide at position 2213 (See SEQ ID NO: 1), wherein vip3C(a) comprises the nucleotide "a" at position 2213, thereby encoding the amino acid Glu at position 738 of SEQ ID NO: 2, and wherein vip3C(b) comprises the nucleotide "g" at position 2213, thereby encoding a Gly at position 738 of SEQ ID NO: 2.

The vip3C(a) and the vip3C(b) genes were each cloned into pET101/D-Topo expression vectors and designated pNOV3911 and pNOV3910, deposited in *E. coli* DH5α cells, and given the accession numbers NRRL B-30552 and NRRL B-30553, respectively.

Example 4

Cosmid Cloning the Full-Length vip3Z Gene

Total DNA was isolated from AB727 by treating freshly grown cells resuspended in 100 mM Tris pH 8, 10 mM EDTA with 2 mg/ml lysozyme for 30 minutes at 37° C. Proteinase K was added to a final concentration of 100 µg/ml in 1% SDS, 50 mM EDTA, 1M urea and incubated at 55° C. An equal volume of phenol-chloroform-isoamyl alcohol was added. The sample was gently mixed for 5 minutes and centrifuged at 3K. This was repeated twice. The aqueous phase was then mixed with 0.7 volumes isopropanol and centrifuged. The DNA pellet was washed three times with 70% ethanol and gently resuspended in 0.5×TE. 12 µg of DNA were treated with 0.3 unit of Sau3A per µg of DNA at 37° C. in a volume of 100 µl. Samples were taken at 2-min intervals for 10 minutes. Then 1/10 volume 10×TE was added and samples were heated for 30 minutes at 65° C. to inactivate the enzyme. The samples were subjected to electrophoresis to determine which fraction is in the 40-kb range and this sample was used in the ligation.

SuperCos cosmid vector (Stratagene, La Jolla, Calif.) was prepared as described by the supplier utilizing the BamHI cloning site. Prepared SuperCos at 100 ng/ml was ligated with the AB727 DNA previously digested with Sau3A at a ratio of 2:1 in a 5 µl volume overnight at 6° C. The ligation mixture was packaged using Gigapack XL III (Stratagene) as described by the supplier. Packaged phages were infected into XL-1MR *E. coli* cells (Stratagene) as described by the supplier. The cosmid library was plated on L-agar with 50 µg/ml kanamycin and incubated 16 hours at 37° C. 200 colonies were picked and grown for screening for the presence of the vip3Z gene.

The 200 cosmid clones were screened for the presence of the vip3Z gene by

```
                                        (SEQ ID NO: 28)
PCR using primer Vip3ZA: 5'-GGCATTTATGGATTTGCCACT
GGTATC-3'
and
                                        (SEQ ID NO: 29)
primer Vip3ZB: 5'-TCCTTTGATACGCAGGTGTAATTTCAG-3'.
```

One cosmid clone, designated 5 g, was shown to comprise the vip3Z gene (SEQ ID NO: 8) encoding the Vip3Z protein (SEQ ID NO: 9).

Example 5

Maize Optimized vip3C Gene Construction

A maize optimized vip3C gene was made according to the procedure disclosed in U.S. Pat. No. 5,625,136, incorporated herein by reference. In this procedure, maize preferred codons, i.e., the single codon that most frequently encodes that amino acid in maize, are used. The maize preferred codon for a particular amino acid is derived from know gene sequences from maize. Maize codon usage for 28 genes from maize plants is found in Murray et al. (1989, Nucleic Acids Res. 17:477-498).

Synthetic vip3C(a) and vip3C(b) genes were made which encode the amino acid sequence depicted in SEQ ID NO: 2. At positions 2213 and 2214 of SEQ ID NO: 3, the synthetic vip3C(a) gene comprises nucleotides "a" and "g", respectively, encoding the amino acid Glu at position 738 of SEQ ID NO: 2, and the synthetic vip3C(b) gene comprises nucleotides "g" and "a", respectively, encoding the amino acid Gly at position 738 of SEQ ID NO: 2. The synthetic vip3C(a) and vip3C(b) genes were separately cloned into pET101/D-Topo expression vectors and the resulting vectors designated pNOV3905, deposited in *E. coli* BL21 cells and given accession number NRRL B-30554, and pNOV3906, deposited in *E. coli* BL21 cells and given the accession number NRRL B-30555.

Example 6

Bioassay of the Vip3C Protein

Black cutworm diet (BioServ, Frenchtown, N.J.) was poured into 50 mm petri dishes. The diet was allowed to cool off and a 200 µl suspension of *E. coli* cells comprising pNOV3905, pNOV3906, pNOV3910 or pNOV3911 was pipetted onto the diet surface. The solution was uniformly spread with a bacterial loop so that the suspension covered the entire surface of the diet. The surface was allowed to dry thoroughly. First instar larvae of the lepidopteran species listed in the table below were placed on the diet with a fine tip brush. Each species was tested separately. Larval mortality, as well as the occurrence of feeding and growth inhibition, was recorded at 3 days and 5 days after larval infestation of the diet. A sample containing *E. coli* cells without an expression vector acted as the negative control. Vip3A protein can also be tested in the same bioassay for comparative purposes or for this example, Vip3C data was compared to the known activity spectrum of Vip3A.

Results are shown in Table 8. Insecticidal activity was observed five days after the plates were infested with insects. The data show that Vip3C(a) (from pNOV3911 and pNOV3905) and Vip3C(b) (from pNOV3910 and 3906) have a broader spectrum of activity than the Vip3A toxin. Tests also indicated that the Vip3C toxin is not active against the environmental beneficial insect *Danaus plexippus*.

TABLE 8

| | % Insect Mortality | | Activity Spectrum of |
|---|---|---|---|
| Insect Tested | Vip3C(a) | Vip3C(b) | Vip3A[b] |
| *Agrotis ipsilon* | 100 | 100 | + |
| *Helicoverpa zea* | 75[a] | 75[a] | + |
| *Heliothis virescens* | 80 | 50 | + |
| *Spodoptera exigua* | 100 | 100 | + |
| *Spodoptera frugiperda* | 70[a] | 70[a] | + |
| *Trichoplusia ni* | 100 | 100 | + |
| *Pectinophora gossypiella* | 50[a] | 60[a] | + |
| *Cochylis hospes* | 90 | 90 | + |
| *Homoeosoma electellum* | 40[a] | 30[a] | + |
| *Ostrinia nubilalis* | 100 | 100 | − |
| *Plutella xylostella* | 100 | 100 | − |

[a]Surviving insects were observed to have severe feeding and growth inhibition.
[b]A "+" indicates an insect species that is susceptible to Vip3A. A "−" indicates an insect species with little or no susceptibility to Vip3A.

Example 7

Creation of Transgenic Maize Plants Comprising a vip3C Gene

Maize optimized vip3C (SEQ ID NO: 3) was chosen for transformation into maize plants. An expression cassette comprising the vip3C(a) sequence was transferred to a suitable vector for *Agrobacterium*-mediated maize transformation. For this example, an expression cassette comprised, in addition to the vip3C(a) gene, the maize ubiquitin promoter and the nos terminater which are known in the art, as well as the phosphomannose isomerase (PMI) gene for selection of transgenic lines (Negrotto et al. (2000) Plant Cell Reports 19: 798-803). The resulting vector was designated pNOV2149 (SEQ ID NO: 30).

Transformation of immature maize embryos was performed essentially as described in Negrotto et al., 2000, Plant Cell Reports 19: 798-803. For this example, all media constituents were as described in Negrotto et al., supra. However, various media constituents known in the art may be substituted.

*Agrobacterium* strain LBA4404 (pSB1) containing the plant transformation plasmid was grown on YEP (yeast extract (5 g/L), peptone (10 g/L), NaCl (5 g/L), 15 g/l agar, pH 6.8) solid medium for 2-4 days at 28° C. Approximately 0.8×10$^9$ *Agrobacterium* were suspended in LS-inf media supplemented with 100 μM As (Negrotto et al., (2000) Plant Cell Rep 19: 798-803). Bacteria were pre-induced in this medium for 30-60 minutes.

Immature embryos from the A188 maize genotype were excised from 8-12 day old ears into liquid LS-inf+100 μM As. Embryos were rinsed once with fresh infection medium. *Agrobacterium* solution was then added and embryos were vortexed for 30 seconds and allowed to settle with the bacteria for 5 minutes. The embryos were then transferred scutellum side up to LSAs medium and cultured in the dark for two to three days. Subsequently, between 20 and 25 embryos per petri plate were transferred to LSDc medium supplemented with cefotaxime (250 mg/l) and silver nitrate (1.6 mg/l) and cultured in the dark for 28° C. for 10 days.

Immature embryos, producing embryogenic callus were transferred to LSD 1M0.5S medium. The cultures were selected on this medium for 6 weeks with a subculture step at 3 weeks. Surviving calli were transferred to Reg1 medium supplemented with mannose. Following culturing in the light (16 hour light/8 hour dark regiment), green tissues were then transferred to Reg2 medium without growth regulators and incubated for 1-2 weeks. Plantlets were transferred to Magenta GA-7 boxes (Magenta Corp, Chicago Ill.) containing Reg3 medium and grown in the light. After 2-3 weeks, plants were tested for the presence of the PMI genes and the vip3C(a) gene by PCR. Positive plants from the PCR assay were transferred to the greenhouse and tested for resistance to lepidopteran pests.

Example 8

Analysis of Transgenic Maize Plants

Plants were sampled as they are being transplanted from Magenta GA-7 boxes into soil. Sampling consisted of cutting two small pieces of leaf (ca. 2-4 cm long) and placing each in a small petri dish. Negative controls were either transgenic plants that were PCR negative for the vip3C(a) gene from the same experiment, or from non-transgenic plants (of a similar size to test plants) that were being grown in the phytotron.

Leaf samples from each plant were inoculated with either European corn borer (*Ostrinia nubilalis*) or fall armyworm (*Spodoptera frugiperda*) by placing 10 first instar larvae onto each leaf piece. Petri dishes were then tightly sealed.

At 3-4 days post inoculation, data were collected. The percent mortality of the larvae was calculated along with a visual damage rating of the leaf. Feeding damage was rated as high, moderate, low, or absent and given a numerical value of 3, 2, 1 or 0, respectively.

Results shown in Table 9 indicate that transgenic maize plants comprising the vip3C(a) gene and expressing the Vip3C(a) protein, are insecticidal to European corn borer (ECB) and fall armyworm (FAW).

TABLE 9

| Event | Plant No. | ECB Mortality | Damage Rating | FAW Mortality | Damage Rating |
|---|---|---|---|---|---|
| 557 | 12A | 80% | 2 | 100% | 0 |
| 557 | 20B | 100% | 1 | 100% | 0 |
| 557 | 8A | 80% | 1 | 70% | 0 |
| 557 | 11A | 100% | 2 | 100% | 0 |
| 557 | 16B | 95% | 2 | 95% | 0 |
| 557 | 18B | 90% | 2 | 100% | 0 |
| 557 | 14B | 100% | 1 | 100% | 0 |
| 556 | 1A | 100% | 1 | 100% | 0 |
| 556 | 3B | 80% | 1 | 100% | 0 |
| 556 | 4A | 95% | 1 | 100% | 0 |
| 556 | 13A | 100% | 1 | 100% | 0 |
| A188 | NEG | 0 | 10 | 0% | 10 |

Example 9

Hybrid Vip3 Toxins

Vip3C is toxic to *Ostrinia nubilalis* (European corn borer) and *Plutella xylostella* (diamond back moth), whereas homologous Vip3 toxins, for example, Vip3A(a), Vip3A(b), and Vip3A(c) are not. Vip3C and Vip3A differ primarily in the C-terminal region of their respective amino acid sequences particularly in the region from amino acid 661 to amino acid 788 of SEQ ID NO: 2. In order to demonstrate that this C-terminal region of Vip3C is the portion of the Vip3C toxin that is responsible for the activity against European corn borer and diamond back moth, a hybrid toxin comprising the C-terminal region of Vip3C, amino acid number 661 to amino acid number 788 of SEQ ID NO: 2, was joined in an amino to carboxy direction with the N-terminal region, from amino acid number 1 to amino acid number 660 of SEQ ID NO: 5, of Vip3A. This hybrid toxin was designated Vip3A-C.

A nucleic acid molecule encoding the Vip3A-C hybrid toxin, was constructed using two steps of PCR with the following primers:

```
                                        (SEQ ID NO: 24)
Vip3A-N: 5'-CACCATGAACAAGAATAATACTAAATTAAGCACAAGAG-
3'

(SEQ ID NO: 25)
Vip3A2050: 5'-TAAAGTTATCTCCCCAAGCTTCATCTCCA-3'

(SEQ ID NO: 26)
Vip3C-C1: 5'-AATGGAGATGAAGCTTGGGGAGAT-3'

(SEQ ID NO: 27)
Vip3C-C2: 5'-TTTATTTAATAGAAACGTTTTCAAATGATATATG-3'
```

In the first PCR step primers Vip3A-N (SEQ ID NO: 24) and Vip3A2050 (SEQ ID NO: 25) were used to generate an approximately 2.0 kb fragment of the 5' end of the vip3A gene, encoding the N-terminal region, and primers Vip3C-C1 (SEQ ID NO: 26) and Vip3C-C2 (SEQ ID NO: 27) were used to generate an approximately 0.4 kb fragment of the 3' end of the vip3C gene, encoding the C-terminal region. In the second PCR step, these two fragments were combined as the templates for primers Vip3A-N (SEQ ID NO: 24) and Vip3C-C2 (SEQ ID NO: 27) to generate an approximately 2.4 kb hybrid vip3A-vip3C gene, designated vip3A-C.

A hybrid vip3A-vip3C(b) gene was made, the sequence of which is set forth in SEQ ID NO: 10. The hybrid vip3A-C gene was cloned into pET101D (Novagen), and the resulting vector designated pNOV3912, and transformed into E. coli DH5a for expression. This E. coli clone, (NRRLB-30551), was tested against the insect species listed in Table 10. The Vip3C protein was used as comparative controls. Data were compared to the known activity spectrum of Vip3A.

The results shown in the Table 10 confirm that the C-terminal region of Vip3C, amino acid number 661 to amino acid number 788 of SEQ ID NO: 2, is sufficient to confer European corn borer and diamond back moth activity on the hybrid toxin.

TABLE 10

| Insect Tested | % Insect Mortality | | Activity Spectrum of |
| --- | --- | --- | --- |
| | Vip3A-C | Vip3C(b)[b] | Vip3A[c] |
| Agrotis ipsilon | 100 | 100 | + |
| Helicoverpa zea | 100 | 75[a] | + |
| Heliothis virescens | 60 | 50 | + |
| Spodoptera exigua | 80 | 100 | + |
| Spodoptera frugiperda | 70[a] | 70[a] | + |
| Trichoplusia ni | 80 | 100 | + |
| Pectinophora gossypiella | 80 | 60[a] | + |
| Cochylis hospes | 100 | 90 | + |
| Homoeosoma electellum | 40[a] | 30[a] | + |
| Ostrinia nubilalis | 100 | 100 | − |
| Plutella xylostella | 100 | 100 | − |

[a]Surviving insects were observed to have severe feeding and growth inhibition.
[b]Data from Example 6.
[c]A "+" indicates an insect species that is susceptible to Vip3A. A "−" indicates an insect species with little or no susceptibility to Vip3A.

Example 10

In vitro Recombination of vip3 Genes by DNA Shuffling

One of the vip3 genes of the present invention (SEQ ID NO: 1, 3, or 11) is amplified by PCR. The resulting DNA fragment is digested by DNaseI treatment essentially as described in Stemmer et al., PNAS 91: 10747-10751 (1994), and the PCR primers are removed from the reaction mixture. A PCR reaction is carried out without primers and is followed by a PCR reaction with the primers, both as described in Stemmer et al. (1994). The resulting DNA fragments are cloned into pTRC99a (Pharmacia, Cat no: 27-5007-01) and transformed into E. coli strain SASX38 by electroporation using the Biorad Gene Pulser and the manufacturer's conditions. The transformed bacteria are grown on medium overnight and screened for insecticidal activity.

In a similar reaction, PCR-amplified DNA fragments comprising one of the vip3 genes described herein (SEQ ID NO: 1, 3, 5, 7, 9, or 11, or mutants thereof), and PCR-amplified DNA fragments comprising at least one other of the vip3 genes described herein (or a mutant thereof) are recombined in vitro and resulting variants with improved insecticidal properties are recovered as described below.

In order to increase the diversity of the shuffled vip3 gene library, a vip3 gene or genes (called the primary genes) are shuffled using synthetic oligonucleotide shuffling. A plurality (e.g., 2, 5, 10, 20, 50, 75, or 100 or more) of oligonucleotides corresponding to at least one region of diversity are synthesized. These oligonucleotides can be shuffled directly, or can be recombined with one or more of the family of nucleic acids.

The oligonucleotide sequence can be taken from other vip3 genes called secondary genes. The secondary genes have a certain degree of homology to the primary genes. There are several ways to select parts of the secondary gene for the oligonucleotide synthesis. For example, portions of the secondary gene can be selected at random. The DNA shuffling process will select those oligonucleotides, which can be incorporated into the shuffled genes.

The selected portions can be any lengths as long as they are suitable to synthesize. The oligonucleotides can also be designed based on the homology between the primary and secondary genes. A certain degree of homology is necessary for crossover, which must occur among DNA fragments during the shuffling. At the same time, strong heterogeneity is desired for the diversity of the shuffled gene library. Furthermore, a specific portion of the secondary genes can be selected for the oligonucleotide synthesis based on the knowledge in the protein sequence and function relationship.

The present invention has disclosed that the C-terminal domain of Vip3 is in part responsible for spectrum of activity of the Vip3 toxins. When the insecticidal spectrum is modified by the current invention utilizing the DNA shuffling technology, the C-terminal region of the nucleotide sequence of the secondary genes can be selected as a target region for synthesizing oligonucleotides used in an oligonucleotide shuffling procedure.

Since the insecticidal activity of the Vip3 protein is dependent, at least in part, to the N-terminal region, the N-terminal region of the secondary genes can be selected for oligonucleotide shuffling for increased insecticidal activity.

In one aspect, the primary vip3C(a) and vip3C(b) genes are shuffled with several oligonucleotides that are synthesized based on the secondary vip3A gene sequence. Vip3C(a) and vip3C(b) are highly homologous, but vip3A is substantially different from these genes. Therefore, it is desirable to shuffle vip3A along with the vip3C(a) and vip3C(b) to increase the diversity of resulting shuffled recombinant nucleic acids. Portions of the vip3A sequence, which are substantially different from the corresponding portions of vip3C(a) and vip3C(b), are selected, and a series of 50-mer oligonucleotides that cover these portions are synthesized. These oligonucleotides are shuffled with the vip3C(a) and vip3C(b). A certain number of the clones are then selected from the shuffled gene library and examined for the diversity by restriction mapping. The diversity is contemplated to be more than normally expected from the shuffling of vip3C(a) and vip3C(b) alone.

Example 11

High-Throughput Screen for Insecticidal Activity

Shuffled vip3 gene libraries in either E. coli or Bacillus thuringiensis are screened for insecticidal activity. Colonies are picked with a Q-bot (Beckman), placed in growth media in a standard 96-well format and grown over night. Each clone is then layered onto the surface of an insect diet in 96-well format and the surface allowed to dry. Optionally, pools of transformed cells are added to each well to increase the number of clones that are tested in the initial screening round. For example, screening 100 clones per well and using 10,000 wells provides a screen of $10^6$ clones.

Several neonate larvae of a target insect, for example, Heliothis virescens, Helicoverpa zea or Spodoptera frugiperda, are added to each well. The plate is covered with an air permeable membrane that retains the larvae in the wells into which they were placed. After 5 days the wells are evaluated for amount of diet consumed and/or insect mortality.

Clones in wells indicating that little or no diet is consumed and/or where high insect mortality is observed are chosen for further analysis. Several clones should be found to have enhanced activity against the target insect.

Example 12

Cosmid Cloning a Full-Length vip3C Gene

Total DNA was isolated from C1674 (NRRL B-30556) by treating freshly grown cells resuspended in 100 mM Tris pH 8, 10 mM EDTA with 2 mg/ml lysozyme for 30 minutes at 37° C. Proteinase K was added to a final concentration of 100 µg/ml in 1% SDS, 50 mM EDTA, 1M urea and incubated at 55° C. An equal volume of phenol-chloroform-isoamyl alcohol was added. The sample was gently mixed for 5 minutes and centrifuged at 3K. This was repeated twice. The aqueous phase was then mixed with 0.7 volumes isopropanol and centrifuged. The DNA pellet was washed three times with 70% ethanol and gently resuspended in 0.5×TE. 12 µg of DNA were treated with 0.3 unit of Sau3A per µg of DNA at 37° C. in a volume of 100 µl. Samples were taken at 2-min intervals for 10 minutes. Then 1/10 volume 10×TE was added and samples were heated for 30 minutes at 65° C. to inactivate the enzyme. The samples were subjected to electrophoresis to determine which fraction is in the 40-kb range and this sample was used in the ligation.

SuperCos cosmid vector (Stratagene, La Jolla, Calif.) was prepared as described by the supplier utilizing the BamHI cloning site. Prepared SuperCos at 100 ng/ml was ligated with the C1674 DNA previously digested with Sau3A at a ratio of 2:1 in a 5 µl volume overnight at 6° C. The ligation mixture was packaged using Gigapack XL III (Stratagene) as described by the supplier. Packaged phages were infected into XL-1MR E. coli cells (Stratagene) as described by the supplier. The cosmid library was plated on L-agar with 50 µg/ml kanamycin and incubated 16 hours at 37° C. 200 colonies were picked and grown for screening for the presence of the vip3C gene.

The 200 cosmid clones were screened for the presence of the vip3C gene by PCR using vip3C specific primers.

Two cosmid clones were shown to comprise a vip3C coding sequence. After several sequencing runs the sequence was confirmed to be the sequence set forth in SEQ ID NO: 31. This vip3C coding sequence was designated vip3C-12168 and encodes the Vip3C-12168 protein (SEQ ID NO: 32).

Example 13

Bioassay of Vip3C-12168

E. coli cells comprising an expression vector (pTrcHis; Invitrogen) comprising the vip3C-12168 coding sequence were tested for biological activity using the protocol described in Example 6. The insect species tested were, European corn borer (ECB), fall armyworm (FAW), black cutworm (BCW), tobacco budworm (TBW), and corn earworm (CEW). Larval mortality, as well as the occurrence of feeding and growth inhibition, was recorded at 7 days after larval infestation of the diet. A sample containing E. coli cells with an empty expression vector (pTrcHis) acted as the negative control. E. coli cells expressing the δ-endotoxin Cry1Ab and E. coli cells expressing Vip3A protein were also tested in the same bioassay for comparison of spectrum of activity.

Results are shown in Table 11. The data show that Vip3C-12168 has the same spectrum of activity as a combination of Cry1Ab and Vip3A.

TABLE 11

|  | % Mortality | | | | |
| --- | --- | --- | --- | --- | --- |
| Treatment | ECB | FAW | BCW | TBW | CEW |
| Cry1Ab | 100 | 0 | 10 | 0[a] | 8 |
| Vip3A | 0 | 100 | 100 | 83[b] | 100 |
| Vip3C-12168 | 100 | 100 | 100 | 92[b] | 100 |
| PTrcHis (empty vector) | 0 | 0 | 10 | 0 | 8 |

[a] Growth inhibition;
[b] Feeding inhibition

Example 14

Maize Optimized Vip3C-12168

A maize optimized vip3C-12168 coding sequence was designed according to the procedure described in Example 5. The nucleotide sequence of the maize optimized vip3C-12168 coding sequence is shown in SEQ ID NO: 33.

All publications and patent applications mentioned in this specification are indicative of the level of skill of those skilled in the art that this invention pertains. All publications and patent applications are herein incorporated by reference to the same extent as if each individual publication or patent application was specifically and individually indicated to be incorporated by reference.

It should be understood that the examples and embodiments described herein are for illustrative purposes only and that various modifications or changes in light thereof will be suggested to persons skilled in the art and are to be included within the spirit and purview of this application and the scope of the appended claims.

---

What is claimed is:

1. A transgenic host cell comprising an expression cassette comprising a heterologous promoter operably linked to a nucleic acid encoding a toxin that is active against European corn borer, wherein said toxin comprises an amino acid sequence that has at least 97% sequence identity with SEQ ID NO: 2 and wherein the C-terminus of said toxin comprises amino acids 661-788 of SEQ ID NO: 2.

2. The transgenic host cell of claim 1, wherein said cell is a bacterial cell.

3. The transgenic host cell of claim 1, wherein said cell is a plant cell.

4. A transgenic plant comprising the transgenic plant cell of claim 3.

5. The transgenic host cell according to claim 1, wherein said toxin comprises an amino acid sequence that has at least 99% identity with SEQ ID NO: 2.

6. The transgenic host cell according to claim 5, wherein said toxin comprises SEQ ID NO: 2.

7. The transgenic host cell according to claim 5, wherein said toxin comprises SEQ ID NO: 11.

8. The transgenic host cell according to claim 5, wherein said toxin comprises SEQ ID NO: 32.

9. The transgenic host cell according to claim 1, wherein said nucleic acid comprises SEQ ID NO: 1.

10. The transgenic host cell according to claim 1, wherein said nucleic acid comprises SEQ ID NO: 3.

11. The transgenic host cell according to claim 1, wherein said nucleic acid comprises SEQ ID NO: 10.

12. The transgenic host cell according to claim 1, wherein said nucleic acid comprises SEQ ID NO: 31.

13. The transgenic host cell according to claim 1, wherein said nucleic acid comprises SEQ ID NO: 33.

14. The transgenic host cell according to claim 1, wherein said toxin is active against a lepidopteran insect selected from the group consisting of *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth).

15. A method of controlling insects, comprising delivering to said insects an effective amount of the transgenic host cell according to claim 1.

16. The method of claim 15, wherein said toxin is active against lepidopteran insects selected from the group consisting of: *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth).

17. The transgenic plant according to claim 4, wherein said toxin comprises an amino acid sequence that has at least 99% identity with SEQ ID NO: 2.

18. The transgenic plant according to claim 17, wherein said toxin comprises SEQ ID NO: 2.

19. The transgenic plant according to claim 17, wherein said toxin comprises SEQ ID NO: 11.

20. The transgenic plant according to claim 17, wherein said toxin comprises SEQ ID NO: 32.

21. The transgenic plant according to claim 4, wherein said nucleic acid comprises SEQ ID NO: 1.

22. The transgenic plant according to claim 4, wherein said nucleic acid comprises SEQ ID NO: 3.

23. The transgenic plant according to claim 4, wherein said nucleic acid comprises SEQ ID NO: 10.

24. The transgenic plant according to claim 4, wherein said nucleic acid comprises SEQ ID NO: 31.

25. The transgenic plant according to claim 4, wherein said nucleic acid comprises SEQ ID NO: 33.

26. A method of controlling insects, comprising delivering to said insects an effective amount of the transgenic plant according to claim 4.

27. The method of claim 26, wherein said toxin is active against lepidopteran insects selected from the group consisting of: *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth).

\* \* \* \* \*

SEQUENCE LISTING

```
<160> NUMBER OF SEQ ID NOS: 33

<210> SEQ ID NO 1
<211> LENGTH: 2367
<212> TYPE: DNA
<213> ORGANISM: Bacillus thuringiensis
<220> FEATURE:
<221> NAME/KEY: misc_feature
<222> LOCATION: (1)..(2367)
<223> OTHER INFORMATION: Native vip3C coding sequence.
      An "r" at position 2213 represents the nucleotide g or a.

<400> SEQUENCE: 1
atgaacaaga ataatactaa attaagcaca agagccctac cgagttttat tgattatttt      60
```

```
aatggcattt atggatttgc cactggtatc aaagacatta tgaatatgat ttttaaaacg    120
gatacaggtg gtaatctaac cttagacgaa atcctaaaga atcagcagtt actaaatgag    180
atttctggta aattggatgg ggtaaatggg agcttaaatg atcttatcgc acagggaaac    240
ttaaatacag aattatctaa ggaaatctta aaaatcgcaa atgaacagaa tcaagtctta    300
aatgatgtta ataacaaact cgatgcgata aatacgatgc ttcatatata tctacctaaa    360
attacatcta tgttaagtga tgtaatgaag caaaattatg cgctaagtct gcaaatagaa    420
tacttaagta agcaattgca agaaatttct gataaattag atattattaa cgtaaatgtt    480
cttattaact ctacacttac tgaaattaca cctgcatatc aacggattaa atatgtgaat    540
gaaaaatttg aagaattaac ttttgctaca gaaccacttt aaaagtaaaa aaggatagc    600 tcgcctgctg atattcttga tgagttaact gaattaactg aactagcgaa aagtgttaca    660
aaaaatgacg ttgatggttt tgaattttac cttaatacat tccacgatgt aatggtagga    720
aataatttat tcgggcgttc agcttttaaaa actgcttcag aattaattgc taagaaaat    780 gtgaaaacaa gtggcagtga agtaggaaat gtttataatt tcttaattgt attaacagct    840
ctacaagcaa aagcttttct tactttaaca acatgccgaa aattattagg cttagcaggt    900
attgattata cttctattat gaatgaacat ttaaataagg aaaagagga atttagagta    960 aacatccttc ctacactttc taatactttt tctaatccta attatgcaaa agttaaagga   1020
agtgatgaag atgcaaagat gattgtggaa gctaaaccag acatgcatt ggttgggttt   1080 gaaatgagca atgattcaat cacagtatta aagtatatg aggctaagct aaaacaaaat   1140
tatcaagttg ataaggattc cctatcggag gttatttatg gtgatacgga taaattattt   1200
tgtccagatc aatctgaaca atatatattat acaaataaca tagtattccc aaatgaatat   1260
gtaattacta aaattgattt cactaaaaaa atgaaaactt aagatatga ggtaacagcg   1320 aattttatg attcttctac aggagaaatt gacttaaata agaaaaagt agaatcaagt   1380 gaagcggagt atagaacgtt aagtgctaat gatgatggag tgtatatgcc attaggtgtc   1440
atcagtgaaa cattttttgac tccgataaat gggtttggcc ttcaagctga tgaaaattca   1500
agattaatta ctttaacatg taaatcatat ttaagagaac tactgctagc aacagactta   1560
agcaataaag aaactaaatt gatcgtccca ccaagtggtt ttattagcaa tattgtagag   1620
aacgggtcca tagaagagga caatttagag ccgtggaaag caaataataa gaatgcgtat   1680
gtagatcata caggcggagt gaatggaact aaagctttat atgttcataa ggacggagga   1740
ttttcacaat ttattggaga taagttaaaa ccgaaaactg agtatgtaat ccaatatact   1800
gttaaaggaa aaccttctat tcatttaaaa gatgaaaata ctggatatat tcattatgaa   1860
gatacaaata taattttaaa agattatcaa actattacta aacgttttac tacaggaact   1920
gatttaaagg gagtgtattt aattttaaaa agtcaaaatg gagatgaagc ttggggagat   1980
aaatttacaa ttttagaaat taagcctgcg gaggatttat taagcccaga attaattaat   2040
ccgaattctt ggattacgac tccagggct agcatttcag gaaataaact tttcattaac   2100
ttggggacaa atgggacctt tagacaaagt cttcattaa acagttattc aacttatagt   2160
ataagcttta ctgcatcagg accatttaat gtgacggtaa gaaattctag ggragtatta   2220
tttgaacgaa gcaaccttat gtcttcaact agtcatattt ctgggacatt caaaactgaa   2280
tccaataata ccggattata tgtagaactt tcccgtcgct ctggtggtgg tggtcatata   2340
tcatttgaaa acgtttctat taaataa                                       2367
```

```
<210> SEQ ID NO 2
<211> LENGTH: 788
<212> TYPE: PRT
<213> ORGANISM: Bacilus thuringiensis
<220> FEATURE:
<221> NAME/KEY: MISC_FEATURE
<222> LOCATION: (1)..(788)
<223> OTHER INFORMATION: Vip3C Toxin
      The Xaa at position 738 is either the amino acid Glu or Gly.

<400> SEQUENCE: 2

Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Ser Pro Ala Asp Ile Leu Asp Glu
        195                 200                 205

Leu Thr Glu Leu Thr Glu Leu Ala Lys Ser Val Thr Lys Asn Asp Val
210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Gly Ile Asp Tyr Thr
290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350
```

```
Pro Gly His Ala Leu Val Gly Phe Glu Met Ser Asn Asp Ser Ile Thr
            355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Thr Asp Lys Leu Phe
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
                420                 425                 430

Thr Leu Arg Tyr Glu Val Thr Ala Asn Phe Tyr Asp Ser Ser Thr Gly
            435                 440                 445

Glu Ile Asp Leu Asn Lys Lys Lys Val Glu Ser Ser Glu Ala Glu Tyr
        450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Gly Ser Ile
    530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Phe Ser Gln Phe Ile Gly Asp Lys Leu Lys Pro Lys
            580                 585                 590

Thr Glu Tyr Val Ile Gln Tyr Thr Val Lys Gly Lys Pro Ser Ile His
        595                 600                 605

Leu Lys Asp Glu Asn Thr Gly Tyr Ile His Tyr Glu Asp Thr Asn Asn
610                 615                 620

Asn Leu Lys Asp Tyr Gln Thr Ile Thr Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Lys Phe Thr Ile Leu Glu Ile Lys Pro Ala Glu Asp
            660                 665                 670

Leu Leu Ser Pro Glu Leu Ile Asn Pro Asn Ser Trp Ile Thr Thr Pro
        675                 680                 685

Gly Ala Ser Ile Ser Gly Asn Lys Leu Phe Ile Asn Leu Gly Thr Asn
    690                 695                 700

Gly Thr Phe Arg Gln Ser Leu Ser Leu Asn Ser Tyr Ser Thr Tyr Ser
705                 710                 715                 720

Ile Ser Phe Thr Ala Ser Gly Pro Phe Asn Val Thr Val Arg Asn Ser
                725                 730                 735

Arg Xaa Val Leu Phe Glu Arg Ser Asn Leu Met Ser Ser Thr Ser His
            740                 745                 750

Ile Ser Gly Thr Phe Lys Thr Glu Ser Asn Asn Thr Gly Leu Tyr Val
        755                 760                 765

Glu Leu Ser Arg Arg Ser Gly Gly Gly Gly His Ile Ser Phe Glu Asn
```

```
                770            775             780
Val Ser Ile Lys
785

<210> SEQ ID NO 3
<211> LENGTH: 2367
<212> TYPE: DNA
<213> ORGANISM: Artificial Sequence
<220> FEATURE:
<223> OTHER INFORMATION: Maize optimized vip3C coding sequence.
      An "r" at positions 2213 and 2214 represents the nucleotide g or
      a.

<400> SEQUENCE: 3
atgaacaaga caacaccaa gctctccacc cgcgccctcc cgtccttcat cgactacttc    60
aacggcatct acggcttcgc caccggcatc aaggacatca tgaacatgat cttcaagacc   120
gacaccggcg gcaacctcac cctcgacgag atcctcaaga ccagcagct cctcaacgag   180 atcagcggca agctcgacgg cgtgaacggc tccctcaacg acctcatcgc ccagggcaac   240
ctcaacaccg agctgtccaa ggagatcctc aagatcgcca acgagcagaa ccaggtgctc   300
aacgacgtga acaacaagct cgacgccatc aacaccatgc tccacatcta cctcccgaag   360
atcacctcca tgctctccga cgtgatgaag cagaactacg ccctctcccct ccagatcgag   420 tacctctcca gcagctcca ggagatcagc gacaagctcg acatcatcaa cgtgaacgtg   480
ctcatcaact ccaccctcac cgagatcacc ccggcctacc agcgcatcaa gtacgtgaac   540
gagaagttcg aggagctgac cttcgccacc gagaccaccc tcaaggtgaa gaaggactcc   600
tccccggccg acatcctcga cgagctgacc gagctgaccg agctggccaa gtccgtgacc   660
aagaacgacg tggacggctt cgagttctac ctcaacaccc tccacgacgt gatggtgggc   720
aacaacctct tcggccgctc cgccctcaag accgcctccg agctgatcgc caaggagaac   780
gtgaagacct ccggctccga ggtgggcaac gtgtacaact tcctcatcgt gctcaccgcc   840
ctgcaggcca aggccttcct cacccctcacc acctgccgca agctcctcgg cctcgccggc   900
atcgactaca cctccatcat gaacgagcac ctcaacaagg agaaggagga gttccgcgtg   960
aacatcctcc cgaccctctc caacaccttc tccaacccga actacgccaa ggtgaagggc  1020
tccgacgagg acgccaagat gatcgtggag gccaagccgg ccacgcccct cgtgggcttc  1080
gagatgtcca acgactccat caccgtgctc aaggtgtacg aggccaagct caagcagaac  1140
taccaggtgg acaaggactc cctctccgag gtgatctacg gcgacaccga caagctcttc  1200
tgccccgacc agtccgagca gatatactac accaacaaca tcgtgttccc gaacgagtac  1260
gtgatcacca agatcgactt caccaagaag atgaagaccc tccgctacga ggtgaccgcc  1320
aacttctacg actcctccac cggcgagatc gacctcaaca agaagaaggt ggagtcctcc  1380
gaggccgagt accgcaccct ctccgccaac gacgacggcg tgtacatgcc gctcggcgtg  1440
atctccgaaa ccttcctcac cccgatcaac ggcttcggcc tccaggccga cgagaactcc  1500
cgcctcatca ccctcacctg caagtcctac ctccgcgagc tgctcctcgc caccgacctc  1560
tccaacaagg agaccaagct catcgtgccg ccgtccggct tcatctccaa catcgtggag  1620
aacggctcca tcgaggagga caacctcgag ccgtggaagg ccaacaacaa gaacgcctac  1680
gtggaccaca cccggcggcgt gaacggcacc aaggccctct acgtgcacaa ggacggcggc  1740
ttctcccagt tcatcggcga caagctcaag ccgaagaccg agtacgtgat ccagtacacc  1800
gtgaagggca agccgtccat ccacctcaag gacgagaaca ccggctacat ccactacgag  1860
```

```
gacaccaaca acaacctcaa ggactaccag accatcacca agcgcttcac caccggcacc      1920
gacctcaagg gcgtgtacct catcctcaag tcccagaacg gcgacgaggc ctggggcgac      1980
aagttcacca tccttgagat caagccggcc gaggacctcc tctccccgga gctgatcaac      2040
ccgaactcct ggatcaccac cccgggcgcc tccatctccg gcaacaagct cttcatcaac      2100
ctcggcacca acggcacctt ccgccagtcc ctctccctca ctcctactc cacctactcc       2160 atctccttca ccgcctccgg cccgttcaac gtgaccgtgc gcaactcccg cgrrgtgctc      2220
ttcgagcgct ccaacctcat gtcctccacc tcccacatct ccggcacctt caagaccgag      2280
tccaacaaca ccggcctcta cgtggagctg tcccgccgct ccggcggcgg cggccacatc      2340
tccttcgaga acgtgtccat caagtag                                          2367

<210> SEQ ID NO 4
<211> LENGTH: 2370
<212> TYPE: DNA
<213> ORGANISM: Bacillus thuringiensis
<220> FEATURE:
<221> NAME/KEY: misc_feature
<222> LOCATION: (1)..(2370)
<223> OTHER INFORMATION: vip3A(a) native coding sequence.

<400> SEQUENCE: 4
atgaacaaga taatactaa attaagcaca agagccttac caagtttat tgattatttt        60 aatggcattt atggatttgc cactggtatc aaagacatta tgaacatgat ttttaaaacg      120
gatacaggtg gtgatctaac cctagacgaa atttaaaga atcagcagtt actaaatgat       180
atttctggta aattggatgg ggtgaatgga agcttaaatg atcttatcgc acagggaaac     240
ttaaatacag aattatctaa ggaaatatta aaaattgcaa atgaacaaaa tcaagttta      300 aatgatgtta ataacaaact cgatgcgata atacgatgc ttcgggtata tctacctaaa     360
attacctcta tgttgagtga tgtaatgaaa caaaattatg cgctaagtct gcaaatagaa     420
tacttaagta acaattgca agagatttct gataagttgg atattattaa tgtaaatgta      480
cttattaact ctacacttac tgaaattaca cctgcgtatc aaaggattaa atatgtgaac     540
gaaaaatttg aggaattaac ttttgctaca gaaactagtt caaaagtaaa aaaggatggc     600
tctcctgcag atattcttga tgagttaact gagttaactg aactagcgaa aagtgtaaca     660
aaaaatgatg tggatggttt tgaattttac cttaatacat tccacgatgt aatggtagga     720
aataatttat tcgggcgttc agctttaaaa actgcatcgg aattaattac taaagaaaat     780
gtgaaaacaa gtggcagtga ggtcggaaat gtttataact tcttaattgt attaacagct     840
ctgcaagcaa aagcttttct tactttaaca acatgccgaa attattagg cttagcagat      900 attgattata cttctattat gaatgaacat ttaaataagg aaaagagga atttagagta      960 aacatcctcc ctacactttc taatactttt tctaatccta ttatgcaaa agttaaagga      1020 agtgatgaag atgcaaagat gattgtggaa gctaaaccag acatgcatt gattgggttt     1080 gaaattagta atgattcaat tacagtatta aaagtatatg aggctaagct aaaacaaaat     1140
tatcaagtcg ataaggattc cttatcggaa gttatttatg gtgatatgga taaattattg    1200
tgcccagatc aatctgaaca aatctattat acaataacaa tagtatttcc aaatgaatat    1260
gtaattacta aaattgattt cactaaaaaa atgaaaactt aagatatga ggtaacagcg     1320 aatttttatg attcttctac aggagaaatt gacttaaata agaaaaagt agaatcaagt    1380 gaagcggagt atagaacgtt aagtgctaat gatgatgggg tgtatatgcc gttaggtgtc    1440
atcagtgaaa cattttgac tccgattaat gggtttggcc tccaagctga tgaaaattca     1500
```

```
agattaatta ctttaacatg taaatcatat ttaagagaac tactgctagc aacagactta   1560
agcaataaag aaactaaatt gatcgtcccg ccaagtggtt ttattagcaa tattgtagag   1620
aacgggtcca tagaagagga caatttagag ccgtggaaag caaataataa gaatgcgtat   1680
gtagatcata caggcggagt gaatggaact aaagctttat atgttcataa ggacggagga   1740
atttcacaat ttattggaga taagttaaaa ccgaaaactg agtatgtaat ccaatatact   1800
gttaaaggaa aaccttctat tcatttaaaa gatgaaaata ctggatatat tcattatgaa   1860
gatacaaata taatttaga agattatcaa actattaata aacgttttac tacaggaact   1920
gatttaaagg gagtgtattt aattttaaaa agtcaaaatg gagatgaagc ttggggagat   1980
aactttatta ttttggaaat tagtccttct gaaaagttat taagtccaga attaattaat   2040
acaaataatt ggacgagtac gggatcaact aatattagcg gtaatacact cactctttat   2100
cagggaggac gagggattct aaaacaaaac cttcaattag atagttttc aacttataga   2160 gtgtatttt ctgtgtccgg agatgctaat gtaaggatta gaaattctag ggaagtgtta   2220
tttgaaaaaa gatatatgag cggtgctaaa gatgtttctg aaatgttcac tacaaaattt   2280
gagaaagata actttatat agagctttct caagggaata atttatatgg tggtcctatt   2340 gtacatttt acgatgtctc tattaagtaa                                    2370
```

<210> SEQ ID NO 5
<211> LENGTH: 789
<212> TYPE: PRT
<213> ORGANISM: Bacillus thuringiensis
<220> FEATURE:
<221> NAME/KEY: MISC_FEATURE
<222> LOCATION: (1)..(789)
<223> OTHER INFORMATION: Vip3A toxin

<400> SEQUENCE: 5

```
Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
                20                  25                  30

Ile Met Asn Met Ile Phe Lys Thr Asp Thr Gly Gly Asp Leu Thr Leu
            35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190
```

-continued

```
Ser Ser Lys Val Lys Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Ile Gly Phe Glu Ile Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Lys Val Glu Ser Ser Glu Ala Glu Tyr
    450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Gly Ser Ile
    530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Ile Ser Gln Phe Ile Gly Asp Lys Leu Lys Pro Lys
            580                 585                 590

Thr Glu Tyr Val Ile Gln Tyr Thr Val Lys Gly Lys Pro Ser Ile His
        595                 600                 605

Leu Lys Asp Glu Asn Thr Gly Tyr Ile His Tyr Glu Asp Thr Asn Asn
```

```
                    610                 615                 620
Asn Leu Glu Asp Tyr Gln Thr Ile Asn Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
                660                 665                 670

Leu Leu Ser Pro Glu Leu Ile Asn Thr Asn Asn Trp Thr Ser Thr Gly
            675                 680                 685

Ser Thr Asn Ile Ser Gly Asn Thr Leu Thr Leu Tyr Gln Gly Gly Arg
        690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
                740                 745                 750

Ser Glu Met Phe Thr Thr Lys Phe Glu Lys Asp Asn Phe Tyr Ile Glu
            755                 760                 765

Leu Ser Gln Gly Asn Asn Leu Tyr Gly Gly Pro Ile Val His Phe Tyr
770                 775                 780

Asp Val Ser Ile Lys
785

<210> SEQ ID NO 6
<211> LENGTH: 2364
<212> TYPE: DNA
<213> ORGANISM: Bacillus thuringiensis
<220> FEATURE:
<221> NAME/KEY: misc_feature
<222> LOCATION: (1)..(2364)
<223> OTHER INFORMATION: vip3B native coding sequence.

<400> SEQUENCE: 6
atgaacaaga ataatactaa attaaacgca agggccttac cgagttttat tgattatttt      60
aatggcattt atggatttgc cactggtatc aaagacatta tgaacatgat ttttaaaacg     120
gatacaggtg gaaatctaac cctagacgaa atttttaaaaa atcagcagtt attaaatgag    180
atttctggta aattggatgg ggtaaatggg agcttaaacg atcttatcgc acagggaaac    240
ttaaatacag aattatctaa ggaaatctta aaaattgcaa atgagcagaa tcaagtctta    300
aatgatgtta taacaaact taatgcgata aatacaatgc ttcacatata tctacctaaa    360
attacatcta tgttaaatga tgtaatgaaa caaaattatg cactaagtct gcaaatagaa    420
tacctaagta aacaattgca agaaatttcc gacaagttag atgtcattaa cgtgaatgta    480
cttattaact ctacacttac tgaaattaca cctgcgtatc aacggatgaa atatgtaaat    540
gaaaaatttg aagattaaac ttttgctaca gaaaccactt taaagtaaa aaagaatagc    600 tcccctgcag atattcttga tgagttaact gagttaactg aactagcgaa aagtgtaaca    660
aaaaatgacg tggatggttt tgaattttac cttaatacat tccacgatgt aatggtagga    720 aacaattat tcgggcgttc agctttaaaa actgcttcgg aattaatcgc taaagaaaat    780
gtgaaaacaa gtggcagtga ggtaggaaat gtttataatt tcttaattgt attaacagct    840
ctgcaagcaa aagctttttct tactttaaca acatgccgga aattattagg cttagcagat    900
attgattata ctttcattat gaatgaacat ttagataagg aaaaagagga atttagagta    960
```

```
aatatccttc ctacactttc taatactttt tctaatccta actatgcaaa agctaaagga    1020
agcaatgaag atgcaaagat aattgtggaa gctaaaccag atatgctttt ggttggattt    1080
gaaatgagca atgattcaat cacagtatta aaagcatatc aggctaagct aaaacaagat    1140
tatcaagttg ataaagattc gttatcagaa attgtctatg gtgatatgga taaattattg    1200
tgcccggatc aatctgaaca aatatattat acaaataaca ttgcttttcc caatgaatat    1260
gtaattacta aaattacttt tactaaaaaa atgaatagtt taagatatga ggcaacagct    1320
aatttttatg attcttctac aggggatatt gatctaaata agacaaaagt agaatcaagt    1380
gaagcagagt atagtacgct aagtgctagt actgatggag tctatatgcc gttaggtatt    1440
atcagtgaaa catttttgac tccaattaat gggtttggaa tcgtagtcga tgaaaattca    1500
aaattagtaa atttaacatg taatcatat ttaagagagg tattattagc aacagactta    1560
agtaataaag aaactaaatt gattgtccca cctattggtt ttattagcaa tattgtagaa    1620
aatgggaact tagagggaga aaacttagag ccgtggaaag caaataacaa aaatgcgtat    1680
gtagatcata caggcggcgt aaatggaact aaagctttat atgttcataa ggatggtgag    1740
ttttcacaat ttattggaga taagttgaaa tcgaaaacag aatatgtaat tcaatatatt    1800 gtaagggaa aagcttctat tcttttgaaa gatgaaaaaa atggtgattg catttatgaa    1860
gatacaaata atggtttaga agattttcaa accattacta aaagttttat tacaggaacg    1920
gattcttcag gagttcattt aatatttaat agtcaaaatg gcgatgaagc atttggggaa    1980
aactttacta tttcagaaat taggctttcc gaagatttat taagtccaga attgataaat    2040
tcagatgctt gggttggatc tcagggaact tggatctcag gaaattcact cactattaat    2100
agtaatgtga atggaacttt tcgacaaaac ctttcgttag aaagctattc aacttatagt    2160
atgaacttta atgtgaatgg atttgccaag gtgacagtaa gaaattcccg tgaagtatta    2220
tttgaaaaaa attatccgca gctttcacct aaagatattt ctgaaaaatt cacaactgca    2280
gccaataata ccgggttgta tgtagagctt tctcgtttta catcgggtgg cgctataaat    2340
ttccggaatt tttcgattaa gtga                                           2364
```

<210> SEQ ID NO 7
<211> LENGTH: 787
<212> TYPE: PRT
<213> ORGANISM: Bacillus thuringiensis
<220> FEATURE:
<221> NAME/KEY: MISC_FEATURE
<222> LOCATION: (1)..(787)
<223> OTHER INFORMATION: Vip3B Toxin

<400> SEQUENCE: 7

```
Met Asn Lys Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asn Ala Ile Asn Thr
```

```
            100                 105                 110
Met Leu His Ile Tyr Leu Pro Lys Ile Thr Ser Met Leu Asn Asp Val
            115                 120                 125

Met Lys Gln Asn Tyr Ala Leu Ser Leu Gln Ile Glu Tyr Leu Ser Lys
            130                 135                 140

Gln Leu Gln Glu Ile Ser Asp Lys Leu Asp Val Ile Asn Val Asn Val
145                 150                 155                 160

Leu Ile Asn Ser Thr Leu Thr Glu Ile Thr Pro Ala Tyr Gln Arg Met
                165                 170                 175

Lys Tyr Val Asn Glu Lys Phe Glu Asp Leu Thr Phe Ala Thr Glu Thr
            180                 185                 190

Thr Leu Lys Val Lys Lys Asn Ser Ser Pro Ala Asp Ile Leu Asp Glu
            195                 200                 205

Leu Thr Glu Leu Thr Glu Leu Ala Lys Ser Val Thr Lys Asn Asp Val
            210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
            275                 280                 285

Leu Thr Thr Cys Arg Lys Leu Leu Gly Leu Ala Asp Ile Asp Tyr Thr
            290                 295                 300

Phe Ile Met Asn Glu His Leu Asp Lys Glu Lys Glu Phe Arg Val
305                 310                 315                 320

Asn Ile Leu Pro Thr Leu Ser Asn Thr Phe Ser Asn Pro Asn Tyr Ala
                325                 330                 335

Lys Ala Lys Gly Ser Asn Glu Asp Ala Lys Ile Ile Val Glu Ala Lys
            340                 345                 350

Pro Gly Tyr Ala Leu Val Gly Phe Glu Met Ser Asn Asp Ser Ile Thr
            355                 360                 365

Val Leu Lys Ala Tyr Gln Ala Lys Leu Lys Gln Asp Tyr Gln Val Asp
            370                 375                 380

Lys Asp Ser Leu Ser Glu Ile Val Tyr Gly Asp Met Asp Lys Leu Leu
385                 390                 395                 400

Cys Pro Asp Gln Ser Glu Gln Ile Tyr Tyr Thr Asn Asn Ile Ala Phe
                405                 410                 415

Pro Asn Glu Tyr Val Ile Thr Lys Ile Thr Phe Thr Lys Lys Met Asn
            420                 425                 430

Ser Leu Arg Tyr Glu Ala Thr Ala Asn Phe Tyr Asp Ser Ser Thr Gly
            435                 440                 445

Asp Ile Asp Leu Asn Lys Thr Lys Val Glu Ser Ser Glu Ala Glu Tyr
            450                 455                 460

Ser Thr Leu Ser Ala Ser Thr Asp Gly Val Tyr Met Pro Leu Gly Ile
465                 470                 475                 480

Ile Ser Glu Thr Phe Leu Thr Pro Ile Asn Gly Phe Gly Ile Val Val
                485                 490                 495

Asp Glu Asn Ser Lys Leu Val Asn Leu Thr Cys Lys Ser Tyr Leu Arg
            500                 505                 510

Glu Val Leu Leu Ala Thr Asp Leu Ser Asn Lys Glu Thr Lys Leu Ile
            515                 520                 525
```

```
Val Pro Pro Ile Gly Phe Ile Ser Asn Ile Val Glu Asn Gly Asn Leu
    530                 535                 540
Glu Gly Glu Asn Leu Glu Pro Trp Lys Ala Asn Asn Lys Asn Ala Tyr
545                 550                 555                 560
Val Asp His Thr Gly Gly Val Asn Gly Thr Lys Ala Leu Tyr Val His
                565                 570                 575
Lys Asp Gly Glu Phe Ser Gln Phe Ile Gly Asp Lys Leu Lys Ser Lys
            580                 585                 590
Thr Glu Tyr Val Ile Gln Tyr Ile Val Lys Gly Lys Ala Ser Ile Leu
        595                 600                 605
Leu Lys Asp Glu Lys Asn Gly Asp Cys Ile Tyr Glu Asp Thr Asn Asn
    610                 615                 620
Gly Leu Glu Asp Phe Gln Thr Ile Thr Lys Ser Phe Ile Thr Gly Thr
625                 630                 635                 640
Asp Ser Ser Gly Val His Leu Ile Phe Asn Ser Gln Asn Gly Asp Glu
                645                 650                 655
Ala Phe Gly Glu Asn Phe Thr Ile Ser Glu Ile Arg Leu Ser Glu Asp
            660                 665                 670
Leu Leu Ser Pro Glu Leu Ile Asn Ser Asp Ala Trp Val Gly Ser Gln
        675                 680                 685
Gly Thr Trp Ile Ser Gly Asn Ser Leu Thr Ile Asn Ser Asn Val Asn
    690                 695                 700
Gly Thr Phe Arg Gln Asn Leu Ser Leu Glu Ser Tyr Ser Thr Tyr Ser
705                 710                 715                 720
Met Asn Phe Asn Val Asn Gly Phe Ala Lys Val Thr Val Arg Asn Ser
                725                 730                 735
Arg Glu Val Leu Phe Glu Lys Asn Tyr Pro Gln Leu Ser Pro Lys Asp
            740                 745                 750

Ile Ser Glu Lys Phe Thr Thr Ala Ala Asn Asn Thr Gly Leu Tyr Val
        755                 760                 765
Glu Leu Ser Arg Phe Thr Ser Gly Gly Ala Ile Asn Phe Arg Asn Phe
    770                 775                 780
Ser Ile Lys
785

<210> SEQ ID NO 8
<211> LENGTH: 2407
<212> TYPE: DNA
<213> ORGANISM: Bacillus thuringiensis
<220> FEATURE:
<221> NAME/KEY: misc_feature
<222> LOCATION: (1)..(2406)
<223> OTHER INFORMATION: vip3Z native coding sequence.

<400> SEQUENCE: 8
atgaataata ctaagttaaa cgcaagggct ttaccaagtt ttattgatta ttttaatggc      60
atttatggat ttgccactgg tatcaaagac attatgaaca tgatttttaa aacggataca     120
ggtggtggta atttaacact agatgaaatt ttaaagaatc aagatttatt aaatcaaatc     180
tcagataaac tcgatggaat taatggagat ttaggtgatc ttattgcaca aggcaattta     240
aattcagaac taactaagga attattaaaa attgcgaatg agcagaatct gatgttaaat     300
aatgttaatg ctcaacttaa ttcaataaat tcaacactta acacctatct gccaaaaatt     360
acatctatgc taagtgaggt aatgaaacaa aactatgtat taagtctaca aatagaattt     420
cttagtgaac aattacaaga aatatcagat aaacttgatg ttatcaattt aaatgtatta     480
```

```
attaactcta cattgacaga aattacgcct gcatatcaac gtattaaata tgtaaatgat      540
aaatttgatg aattgacttc tactgtggaa aaaaatccga aaattaatca agataatttt      600
actgaagatg ttattgataa tttaactgat ttaactgaac tagcacgaag tgtaacgaga      660
aatgatatgg atagttttga atttatatt aaaactttcc atgatgtgat gataggaaat       720
aatttattca gtcgttctgc attaaaaact gcttcagaat taattgctaa ggaaaatata      780
catactatgg aagtgaaat tggtaatgtc tacacttta tggttgtttt gacttcctta        840
caagcaaaag cgttcctaac tttaactgca tgccgtaaat tattaggatt aacagatatc      900
gattatacac aaattatgaa tgaaaattta aatagaaaa agaggaatt tcgcttaaat        960 attcttccta cactttctaa tgatttttct aatcctaatt atacagaaac tttaggaagt     1020
gatcttgtag atcctattgt tacgttagaa gctgatcctg ttatgctttt aataggtttt     1080
gagattctca atgatccact tccagtatta aaagtatatc aggcaaagct aaaaccaaat     1140
tatcaagtcg acaaagagtc gattatgaa atatttatg gaaatatcca caactactt       1200 tgtccaaaac aacgtcacca aaaatattat ataaaagaca ttacatttcc tgaaggttat     1260
gtaatcacca aaattgtttt tgaaaaaaaa ttgaatctat taggatatga agtaacagca     1320
aatctttatg acccatttac aggaagtatc gatttgaata agactattct agaatcatgg     1380
aaggaagaat gctgtgaaga agaatgctgt gaagaagaat gctgtgaaga agaatgctgt     1440
gaagaattat ataaaattat agaggcggat actaacggtg tttatatgcc gttgggagta     1500
attagtgaaa catttttaac accaatctat agttttaaac taattattga cgaaagaaca     1560
aagagaatat ctttagcggg taaatcttat ttacgtgaat ctttactagc cacagattta     1620
gttaataaag atacgaattt aattccttca cccaatggtt tcattaacag tattgtggaa     1680
aattggaata taacatcgga taatatagag ccctggaaag cgaataataa aaatgcatat     1740
gtcgataaga cggatgacat ggtgggattt aactctttat atactcataa ggatggggaa     1800
ttcttgcaat ttattggagc taagttaaag gctaaaactg agtatatcat tcaatatact     1860
gtaaaaggga gtccggaagt ttatttgaaa acaataaag gtatcttta tgaggataca      1920 acaaataaat ttgatacgtt tcaaactata actaaaaagt tcaattcagg agtagatcca     1980
tccgaaatat atctagtttt taaaaatcaa attggatatg aagcatgggg aaataaattt     2040
attatactag aaatcaagtc atttgaaacc ctaccacaaa tattaaaacc tgaaaattgg     2100
atgccttttg gtaatgctga gattaaagaa gatggaaaaa ttgagatttc aggtaatgga     2160
actatgacgc aaaatattca attagaacag aattccaagt atcatctaag attttctgta     2220
aaaggaaaag ggagagtagc gatacaaact caaagctccc atataaatgt accagctaca     2280
aacgaagagg tttctacaat gattacaact agaaacttat acggtgaagg tatgatatac     2340
ctatttaatg atgacgtgga gaactccaaa gttattttt cggatgtatc tctagttaaa     2400
gaatagg                                                              2407
```

<210> SEQ ID NO 9
<211> LENGTH: 801
<212> TYPE: PRT
<213> ORGANISM: Bacillus thuringiensis
<220> FEATURE:
<221> NAME/KEY: MISC_FEATURE
<222> LOCATION: (1)..(801)
<223> OTHER INFORMATION: Vip3Z toxin

<400> SEQUENCE: 9

```
Met Asn Asn Thr Lys Leu Asn Ala Arg Ala Leu Pro Ser Phe Ile Asp
1               5                   10                  15

Tyr Phe Asn Gly Ile Tyr Gly Phe Ala Thr Gly Ile Lys Asp Ile Met
            20                  25                  30

Asn Met Ile Phe Lys Thr Asp Thr Gly Gly Asn Leu Thr Leu Asp
        35                  40                  45

Glu Ile Leu Lys Asn Gln Asp Leu Leu Asn Gln Ile Ser Asp Lys Leu
50                  55                  60

Asp Gly Ile Asn Gly Asp Leu Gly Asp Leu Ile Ala Gln Gly Asn Leu
65                  70                  75                  80

Asn Ser Glu Leu Thr Lys Glu Leu Leu Lys Ile Ala Asn Glu Gln Asn
            85                  90                  95

Leu Met Leu Asn Asn Val Asn Ala Gln Leu Asn Ser Ile Asn Ser Thr
        100                 105                 110

Leu Asn Thr Tyr Leu Pro Lys Ile Thr Ser Met Leu Ser Glu Val Met
        115                 120                 125

Lys Gln Asn Tyr Val Leu Ser Leu Gln Ile Glu Phe Leu Ser Glu Gln
        130                 135                 140

Leu Gln Glu Ile Ser Asp Lys Leu Asp Val Ile Asn Leu Asn Val Leu
145                 150                 155                 160

Ile Asn Ser Thr Leu Thr Glu Ile Thr Pro Ala Tyr Gln Arg Ile Lys
                165                 170                 175

Tyr Val Asn Asp Lys Phe Asp Glu Leu Thr Ser Thr Val Glu Lys Asn
            180                 185                 190

Pro Lys Ile Asn Gln Asp Asn Phe Thr Glu Asp Val Ile Asp Asn Leu
        195                 200                 205

Thr Asp Leu Thr Glu Leu Ala Arg Ser Val Thr Arg Asn Asp Met Asp
210                 215                 220

Ser Phe Glu Phe Tyr Ile Lys Thr Phe His Asp Val Met Ile Gly Asn
225                 230                 235                 240

Asn Leu Phe Ser Arg Ser Ala Leu Lys Thr Ala Ser Glu Leu Ile Ala
            245                 250                 255

Lys Glu Asn Ile His Thr Met Gly Ser Glu Ile Gly Asn Val Tyr Thr
        260                 265                 270

Phe Met Val Val Leu Thr Ser Leu Gln Ala Lys Ala Phe Leu Thr Leu
        275                 280                 285

Thr Ala Cys Arg Lys Leu Leu Gly Leu Thr Asp Ile Asp Tyr Thr Gln
        290                 295                 300

Ile Met Asn Glu Asn Leu Asn Arg Glu Lys Glu Glu Phe Arg Leu Asn
305                 310                 315                 320

Ile Leu Pro Thr Leu Ser Asn Asp Phe Ser Asn Pro Asn Tyr Thr Glu
                325                 330                 335

Thr Leu Gly Ser Asp Leu Val Asp Pro Ile Val Thr Leu Glu Ala Asp
            340                 345                 350

Pro Gly Tyr Ala Leu Ile Gly Phe Glu Ile Leu Asn Asp Pro Leu Pro
        355                 360                 365

Val Leu Lys Val Tyr Gln Ala Lys Leu Lys Pro Asn Tyr Gln Val Asp
        370                 375                 380

Lys Glu Ser Ile Met Glu Asn Ile Tyr Gly Asn Ile His Lys Leu Leu
385                 390                 395                 400

Cys Pro Lys Gln Arg His Gln Lys Tyr Ile Lys Asp Ile Thr Phe
            405                 410                 415

Pro Glu Gly Tyr Val Ile Thr Lys Ile Val Phe Glu Lys Lys Leu Asn
```

```
                420             425             430
Leu Leu Gly Tyr Glu Val Thr Ala Asn Leu Tyr Asp Pro Phe Thr Gly
            435             440             445

Ser Ile Asp Leu Asn Lys Thr Ile Leu Glu Ser Trp Lys Glu Glu Cys
        450             455             460

Cys Glu Glu Cys Glu Glu Cys Cys Glu Glu Cys Cys Glu Glu Cys Cys
465             470             475             480

Glu Glu Leu Tyr Lys Ile Ile Glu Ala Asp Thr Asn Gly Val Tyr Met
                485             490             495

Pro Leu Gly Val Ile Ser Glu Thr Phe Leu Thr Pro Ile Tyr Ser Phe
            500             505             510

Lys Leu Ile Ile Asp Glu Arg Thr Lys Arg Ile Ser Leu Ala Gly Lys
        515             520             525

Ser Tyr Leu Arg Glu Ser Leu Leu Ala Thr Asp Leu Val Asn Lys Asp
    530             535             540

Thr Asn Leu Ile Pro Ser Pro Asn Gly Phe Ile Asn Ser Ile Val Glu
545             550             555             560

Asn Trp Asn Ile Thr Ser Asp Asn Ile Glu Pro Trp Lys Ala Asn Asn
            565             570             575

Lys Asn Ala Tyr Val Asp Lys Thr Asp Asp Met Val Gly Phe Asn Ser
                580             585             590

Leu Tyr Thr His Lys Asp Gly Glu Phe Leu Gln Phe Ile Gly Ala Lys
            595             600             605

Leu Lys Ala Lys Thr Glu Tyr Ile Ile Gln Tyr Thr Val Lys Gly Ser
        610             615             620

Pro Glu Val Tyr Leu Lys Asn Asn Lys Gly Ile Phe Tyr Glu Asp Thr
625             630             635             640

Thr Asn Lys Phe Asp Thr Phe Gln Thr Ile Thr Lys Lys Phe Asn Ser
            645             650             655

Gly Val Asp Pro Ser Glu Ile Tyr Leu Val Phe Lys Asn Gln Ile Gly
                660             665             670

Tyr Glu Ala Trp Gly Asn Lys Phe Ile Ile Leu Glu Ile Lys Ser Phe
            675             680             685

Glu Thr Leu Pro Gln Ile Leu Lys Pro Glu Asn Trp Met Pro Phe Gly
        690             695             700

Asn Ala Glu Ile Lys Glu Asp Gly Lys Ile Glu Ile Ser Gly Asn Gly
705             710             715             720

Thr Met Thr Gln Asn Ile Gln Leu Glu Gln Asn Ser Lys Tyr His Leu
            725             730             735

Arg Phe Ser Val Lys Gly Lys Gly Arg Val Ala Ile Gln Thr Gln Ser
                740             745             750

Ser His Ile Asn Val Pro Ala Thr Asn Glu Glu Val Ser Thr Met Ile
            755             760             765

Thr Thr Arg Asn Leu Tyr Gly Glu Gly Met Ile Tyr Leu Phe Asn Asp
        770             775             780

Asp Val Glu Asn Ser Lys Val Ile Phe Ser Asp Val Ser Leu Val Lys
785             790             795             800

Glu

<210> SEQ ID NO 10
<211> LENGTH: 2367
<212> TYPE: DNA
<213> ORGANISM: Artificial Sequence
<220> FEATURE:
```

<223> OTHER INFORMATION: vip3A-C Hybrid toxin coding sequence.

<400> SEQUENCE: 10

```
atgaacaaga ataatactaa attaagcaca agagccttac caagtttat tgattatttt      60
aatggcattt atggatttgc cactggtatc aaagacatta tgaacatgat ttttaaaacg     120
gatacaggtg gtgatctaac cctagacgaa attttaaaga atcagcagtt actaaatgat    180
atttctggta aattggatgg ggtgaatgga agcttaaatg atcttatcgc acagggaaac    240
ttaaatacag aattatctaa ggaaatatta aaaattgcaa atgaacaaaa tcaagtttta    300
aatgatgtta ataacaaact cgatgcgata aatacgatgc ttcgggtata tctacctaaa    360
attacctcta tgttgagtga tgtaatgaaa caaaattatg cgctaagtct gcaaatagaa    420
tacttaagta aacaattgca agagatttct gataagttgg atattattaa tgtaaatgta    480
cttattaact ctacacttac tgaaattaca cctgcgtatc aaaggattaa atatgtgaac    540
gaaaaatttg aggaattaac ttttgctaca gaaactagtt caaaagtaaa aaaggatggc    600
tctcctgcag atattcttga tgagttaact gagttaactg aactagcgaa aagtgtaaca    660
aaaaatgatg tggatggttt tgaattttac cttaatacat ccacgatgt aatggtagga    720
aataatttat tcgggcgttc agcttttaaaa actgcatcgg aattaattac taagaaaat    780
gtgaaaacaa gtggcagtga ggtcggaaat gtttataact tcttaattgt attaacagct    840
ctgcaagcaa aagcttttct tactttaaca acatgccgaa aattattagg cttagcagat    900
attgattata cttctattat gaatgaacat ttaaataagg aaaagagga atttagagta    960
aacatcctcc ctacactttc taatactttt tctaatccta attatgcaaa agttaaagga   1020
agtgatgaag atgcaaagat gattgtggaa gctaaaccag acatgcatt gattgggttt   1080
gaaattagta atgattcaat tacagtatta aaagtatatg aggctaagct aaaacaaaat   1140
tatcaagtcg ataaggattc cttatcggaa gttatttatg gtgatatgga taaattattg   1200
tgcccagatc aatctgaaca aatctattat acaaataaca tagtatttcc aaatgaatat   1260
gtaattacta aaattgattt cactaaaaaa atgaaaactt taagatatga ggtaacagcg   1320
aatttttatg attcttctac aggagaaatt gacttaaata agaaaaagt agaatcaagt   1380
gaagcggagt atagaacgtt aagtgctaat gatgatgggg tgtatatgcc gttaggtgtc   1440
atcagtgaaa cattttttgac tccgattaat gggtttggcc tccaagctga tgaaaattca   1500
agattaatta ctttaacatg taatcatat ttaagagaac tactgctagc aacagactta   1560
agcaataaag aaactaaatt gatcgtcccg ccaagtggtt ttattagcaa tattgtagag   1620
aacgggtcca tagaagagga caatttagag ccgtggaaag caataataaa gaatgcgtat   1680
gtagatcata caggcggagt gaatggaact aaagctttat atgttcataa ggacggagga   1740
atttcacaat tattggaga taagttaaaa ccgaaaactg agtatgtaat ccaatatact   1800
gttaaaggaa aaccttctat tcatttaaaa gatgaaaata ctggatatat tcattatgaa   1860
gatacaaata taatttaga agattatcaa actattaata acgttttac tacaggaact   1920
gatttaaagg gagtgtattt aattttaaaa agtcaaaatg gagatgaagc ttggggagat   1980
aaatttacaa ttttagaaat taagcctgcg gaggatttat aagcccaga attaattaat   2040
ccgaattctt ggattacgac tccagggct agcatttcag gaaataaact tttcattaac   2100
ttggggacaa atgggacctt tagacaaagt ctttcattaa acagttattc aacttatagt   2160
ataagcttta ctgcatcagg accatttaat gtgacggtaa gaattctag ggagtatta   2220
tttgaacgaa gcaaccttat gtcttcaact agtcatattt ctgggacatt caaaactgaa   2280
```

-continued

```
tccaataata ccggattata tgtagaactt tcccgtcgct ctggtggtgg tggtcatata    2340
tcatttgaaa acgtttctat taaataa                                        2367
```

<210> SEQ ID NO 11
<211> LENGTH: 788
<212> TYPE: PRT
<213> ORGANISM: Artificial sequence
<220> FEATURE:
<223> OTHER INFORMATION: Hybrid Vip3A-C toxin

<400> SEQUENCE: 11

```
Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
```

-continued

```
                340                 345                 350
Pro Gly His Ala Leu Ile Gly Phe Glu Ile Ser Asn Asp Ser Ile Thr
            355                 360                 365
Val Leu Lys Val Tyr Glu Ala Lys Leu Lys Gln Asn Tyr Gln Val Asp
        370                 375                 380
Lys Asp Ser Leu Ser Glu Val Ile Tyr Gly Asp Met Asp Lys Leu Leu
385                 390                 395                 400
Cys Pro Asp Gln Ser Glu Gln Ile Tyr Tyr Thr Asn Asn Ile Val Phe
                405                 410                 415
Pro Asn Glu Tyr Val Ile Thr Lys Ile Asp Phe Thr Lys Lys Met Lys
            420                 425                 430
Thr Leu Arg Tyr Glu Val Thr Ala Asn Phe Tyr Asp Ser Ser Thr Gly
        435                 440                 445
Glu Ile Asp Leu Asn Lys Lys Val Glu Ser Glu Ala Glu Tyr
450                 455                 460
Arg Thr Leu Ser Ala Asn Asp Asp Gly Val Tyr Met Pro Leu Gly Val
465                 470                 475                 480
Ile Ser Glu Thr Phe Leu Thr Pro Ile Asn Gly Phe Gly Leu Gln Ala
                485                 490                 495
Asp Glu Asn Ser Arg Leu Ile Thr Leu Thr Cys Lys Ser Tyr Leu Arg
            500                 505                 510
Glu Leu Leu Leu Ala Thr Asp Leu Ser Asn Lys Glu Thr Lys Leu Ile
        515                 520                 525
Val Pro Pro Ser Gly Phe Ile Ser Asn Ile Val Glu Asn Gly Ser Ile
    530                 535                 540
Glu Glu Asp Asn Leu Glu Pro Trp Lys Ala Asn Asn Lys Asn Ala Tyr
545                 550                 555                 560
Val Asp His Thr Gly Gly Val Asn Gly Thr Lys Ala Leu Tyr Val His
                565                 570                 575
Lys Asp Gly Gly Ile Ser Gln Phe Ile Gly Asp Lys Leu Lys Pro Lys
            580                 585                 590
Thr Glu Tyr Val Ile Gln Tyr Thr Val Lys Gly Lys Pro Ser Ile His
        595                 600                 605
Leu Lys Asp Glu Asn Thr Gly Tyr Ile His Tyr Glu Asp Thr Asn Asn
    610                 615                 620
Asn Leu Glu Asp Tyr Gln Thr Ile Asn Lys Arg Phe Thr Thr Gly Thr
625                 630                 635                 640
Asp Leu Lys Gly Val Tyr Leu Ile Leu Lys Ser Gln Asn Gly Asp Glu
                645                 650                 655
Ala Trp Gly Asp Lys Phe Thr Ile Leu Glu Ile Lys Pro Ala Glu Asp
            660                 665                 670
Leu Leu Ser Pro Glu Leu Ile Asn Pro Asn Ser Trp Ile Thr Thr Pro
        675                 680                 685
Gly Ala Ser Ile Ser Gly Asn Lys Leu Phe Ile Asn Leu Gly Thr Asn
    690                 695                 700
Gly Thr Phe Arg Gln Ser Leu Ser Leu Asn Ser Tyr Ser Thr Tyr Ser
705                 710                 715                 720
Ile Ser Phe Thr Ala Ser Gly Pro Phe Asn Val Thr Arg Asn Ser
                725                 730                 735
Arg Gly Val Leu Phe Glu Arg Ser Asn Leu Met Ser Ser Thr Ser His
            740                 745                 750
Ile Ser Gly Thr Phe Lys Thr Glu Ser Asn Asn Thr Gly Leu Tyr Val
        755                 760                 765
```

Glu Leu Ser Arg Arg Ser Gly Gly Gly Gly His Ile Ser Phe Glu Asn
    770                 775                 780

Val Ser Ile Lys
785

<210> SEQ ID NO 12
<211> LENGTH: 36
<212> TYPE: DNA
<213> ORGANISM: Artificial Sequence
<220> FEATURE:
<223> OTHER INFORMATION: 1F Forward primer

<400> SEQUENCE: 12
atgaacaaga ataatactaa attaagcaca agagcc                           36

<210> SEQ ID NO 13
<211> LENGTH: 35
<212> TYPE: DNA
<213> ORGANISM: Artificial Sequence
<220> FEATURE:
<223> OTHER INFORMATION: 1R reverse primer

<400> SEQUENCE: 13
ctcaacatag aggtaatttt aggtagatat acccg                            35

<210> SEQ ID NO 14
<211> LENGTH: 25
<212> TYPE: DNA
<213> ORGANISM: Artificial Sequence
<220> FEATURE:
<223> OTHER INFORMATION: Primer P3

<400> SEQUENCE: 14
gatgatgggg tgtatatgcc gttag                                       25

<210> SEQ ID NO 15
<211> LENGTH: 25
<212> TYPE: DNA
<213> ORGANISM: Artificial Sequence
<220> FEATURE:
<223> OTHER INFORMATION: Primer P4

<400> SEQUENCE: 15
aataaattgt gaaattcctc cgtcc                                       25

<210> SEQ ID NO 16
<211> LENGTH: 33
<212> TYPE: DNA
<213> ORGANISM: Artificial Sequence
<220> FEATURE:
<223> OTHER INFORMATION: Primer 4F

<400> SEQUENCE: 16
agtcaaaatg gagatcaagg ttggggagat aac                              33

<210> SEQ ID NO 17
<211> LENGTH: 34
<212> TYPE: DNA
<213> ORGANISM: Artificial Sequence
<220> FEATURE:
<223> OTHER INFORMATION: Primer 4R

<400> SEQUENCE: 17
ttacttaata gagagatcgt ggaaatgtac aata                             34

<210> SEQ ID NO 18
<211> LENGTH: 23
<212> TYPE: DNA
<213> ORGANISM: Artificial Sequence
<220> FEATURE:
<223> OTHER INFORMATION: Primer P5

<400> SEQUENCE: 18
aatggagatg aagcttgggg aga                                              23

<210> SEQ ID NO 19
<211> LENGTH: 25
<212> TYPE: DNA
<213> ORGANISM: Artificial Sequence
<220> FEATURE:
<223> OTHER INFORMATION: Primer P6

<400> SEQUENCE: 19
cgtggaaatg tacaatagga ccacc                                            25

<210> SEQ ID NO 20
<211> LENGTH: 25
<212> TYPE: DNA
<213> ORGANISM: Artificial Sequence
<220> FEATURE:
<223> OTHER INFORMATION: Primer Vip3CF4

<400> SEQUENCE: 20
gtttagaaga ttttcaaacc attac                                            25

<210> SEQ ID NO 21
<211> LENGTH: 21
<212> TYPE: DNA
<213> ORGANISM: Artificial Sequence
<220> FEATURE:
<223> OTHER INFORMATION: Primer T7

<400> SEQUENCE: 21
ttaatacgac tcactatagg g                                                21

<210> SEQ ID NO 22
<211> LENGTH: 34
<212> TYPE: DNA
<213> ORGANISM: Artificial Sequence
<220> FEATURE:
<223> OTHER INFORMATION: Primer Vip3Cc

<400> SEQUENCE: 22
tttatttaat agaaacgttt tcaaatgata tatg                                  34

<210> SEQ ID NO 23
<211> LENGTH: 38
<212> TYPE: DNA
<213> ORGANISM: Artificial Sequence
<220> FEATURE:
<223> OTHER INFORMATION: Primer Vip3Cn

<400> SEQUENCE: 23
caccatgaac aagaataata ctaaattaag cacaagag                              38

<210> SEQ ID NO 24
<211> LENGTH: 38
<212> TYPE: DNA
<213> ORGANISM: Artificial Sequence
<220> FEATURE:
<223> OTHER INFORMATION: Primer Vip3A-N -continued

```
<400> SEQUENCE: 24
caccatgaac aagaataata ctaaattaag cacaagag                                38

<210> SEQ ID NO 25
<211> LENGTH: 29
<212> TYPE: DNA
<213> ORGANISM: Artificial Sequence
<220> FEATURE:
<223> OTHER INFORMATION: Primer Vip3A2050

<400> SEQUENCE: 25
taaagttatc tccccaagct tcatctcca                                          29

<210> SEQ ID NO 26
<211> LENGTH: 24
<212> TYPE: DNA
<213> ORGANISM: Artificial Sequence
<220> FEATURE:
<223> OTHER INFORMATION: Vip3C-C1

<400> SEQUENCE: 26
aatggagatg aagcttgggg agat                                               24

<210> SEQ ID NO 27
<211> LENGTH: 34
<212> TYPE: DNA
<213> ORGANISM: Artificial Sequence
<220> FEATURE:
<223> OTHER INFORMATION: Vip3C-C2

<400> SEQUENCE: 27
tttatttaat agaaacgttt tcaaatgata tatg                                    34

<210> SEQ ID NO 28
<211> LENGTH: 27
<212> TYPE: DNA
<213> ORGANISM: Artificial Sequence
<220> FEATURE:
<223> OTHER INFORMATION: Primer Vip3Za

<400> SEQUENCE: 28
ggcatttatg gatttgccac tggtatc                                            27

<210> SEQ ID NO 29
<211> LENGTH: 27
<212> TYPE: DNA
<213> ORGANISM: Artificial Sequence
<220> FEATURE:
<223> OTHER INFORMATION: Primer Vip3Zb

<400> SEQUENCE: 29
tcctttgata cgcaggtgta atttcag                                            27

<210> SEQ ID NO 30
<211> LENGTH: 13829
<212> TYPE: DNA
<213> ORGANISM: Artificial Sequence
<220> FEATURE:
<223> OTHER INFORMATION: pNOV2149

<400> SEQUENCE: 30
aagcttgcat gcctgcagtg cagcgtgacc cggtcgtgcc cctctctaga gataatgagc        60
attgcatgtc taagttataa aaaattacca catatttttt ttgtcacact tgtttgaagt       120
```

-continued

```
gcagtttatc tatctttata catatattta aacttactc tacgaataat ataatctata    180
gtactacaat aatatcagtg ttttagagaa tcatataaat gaacagttag acatggtcta    240
aaggacaatt gagtattttg acaacaggac tctacagttt tatcttttta gtgtgcatgt    300
gttctccttt ttttttgcaa atagcttcac ctatataata cttcatccat tttattagta    360
catccattta gggtttaggg ttaatggttt ttatagacta atttttttag tacatctatt    420
ttattctatt ttagcctcta aattaagaaa actaaaactc tattttagtt tttttattta    480
ataatttaga tataaaatag aataaaataa agtgactaaa aattaaacaa ataccctta     540
agaaattaaa aaaactaagg aaacattttt cttgtttcga gtagataatg ccagcctgtt    600
aaacgccgtc gacgagtcta acggacacca accagcgaac cagcagcgtc gcgtcgggcc    660
aagcgaagca gacggcacgg catctctgtc gctgcctctg gaccctctc gagagttccg     720
ctccaccgtt ggacttgctc cgctgtcggc atccagaaat tgcgtggcgg agcggcagac    780
gtgagccggc acggcaggcg gcctcctcct cctctcacgg caccggcagc tacgggggat    840
tcctttccca ccgctccttc gctttccctt cctcgcccgc cgtaataaat agacaccccc    900
tccacaccct ctttccccaa cctcgtgttg ttcggagcgc acacacacac aaccagatct    960
cccccaaatc caccgtcgg cacctccgct tcaaggtacg ccgctcgtcc tccccccccc   1020
cccctctcta ccttctctag atcggcgttc cggtccatgg ttagggcccg gtagttctac   1080
ttctgttcat gtttgtgtta gatccgtgtt tgtgttagat ccgtgctgct agcgttcgta   1140
cacggatgcg acctgtacgt cagacacgtt ctgattgcta acttgccagt gtttctcttt   1200
ggggaatcct gggatggctc tagccgttcc gcagacggga tcgatttcat gattttttt    1260
gtttcgttgc atagggtttg gtttgccctt ttcctttatt tcaatatatg ccgtgcactt   1320
gtttgtcggg tcatcttttc atgctttttt ttgtcttggt tgtgatgatg tggtctggtt   1380
gggcggtcgt tctagatcgg agtagaattc tgtttcaaac tacctggtgg atttattaat   1440
tttggatctg tatgtgtgtg ccatacatat tcatagttac gaattgaaga tgatggatgg   1500
aaatatcgat ctaggatagg tatacatgtt gatgcgggtt ttactgatgc atatacagag   1560
atgcttttg ttcgcttggt tgtgatgatg tggtgtggtt gggcggtcgt tcattcgttc   1620
tagatcggag tagaatactg tttcaaacta cctggtgtat ttattaattt tggaactgta   1680
tgtgtgtgtc atacatcttc atagttacga gtttaagatg gatggaaata tcgatctagg   1740
ataggtatac atgttgatgt gggttttact gatgcatata catgatggca tatgcagcat   1800
ctattcatat gctctaacct tgagtaccta tctattataa taaacaagta tgttttataa   1860
ttattttgat cttgatatac ttggatgatg gcatatgcag cagctatatg tggattttt    1920
tagccctgcc ttcatacgct atttatttgc ttggtactgt ttcttttgtc gatgctcacc   1980
ctgttgtttg gtgttacttc tgcagggatc caccatgaac aagaacaaca ccaagctctc   2040
cacccgcgcc ctcccgtcct tcatcgacta cttcaacggc atctacgct tcgccaccgg    2100
catcaaggac atcatgaaca tgatcttcaa gaccgacacc ggcggcaacc tcaccctcga   2160
cgagatcctc aagaaccagc agctcctcaa cgagatcagc ggcaagctcg acggcgtgaa   2220
cggctccctc aacgacctca tcgcccaggg caacctcaac accgagctgt ccaaggagat   2280
cctcaagatc gccaacgagc agaaccaggt gctcaacgac gtgaacaaca agctcgacgc   2340
catcaacacc atgctccaca tctacctccc gaagatcacc tccatgctct ccgacgtgat   2400
gaagcagaac tacgccctct ccctccagat cgagtacctc tccaagcagc tccaggagat   2460
cagcgacaag ctcgacatca tcaacgtgaa cgtgctcatc aactccaccc tcaccgagat   2520
```

```
caccccggcc taccagcgca tcaagtacgt gaacgagaag ttcgaggagc tgaccttcgc   2580
caccgagacc accctcaagg tgaagaagga ctcctccccg gccgacatcc tcgacgagct   2640
gaccgagctg accgagctgg ccaagtccgt gaccaagaac gacgtggacg gcttcgagtt   2700
ctacctcaac accttccacg acgtgatggt gggcaacaac ctcttcggcc gctccgccct   2760
caagaccgcc tccgagctga tcgccaagga gaacgtgaag acctccggct ccgaggtggg   2820
caacgtgtac aacttcctca tcgtgctcac cgccctgcag gccaaggcct tcctcaccct   2880
caccacctgc cgcaagctcc tcggcctcgc cggcatcgac tacacctcca tcatgaacga   2940
gcacctcaac aaggagaagg aggagttccg cgtgaacatc ctcccgaccc tctccaacac   3000
cttctccaac ccgaactacg ccaaggtgaa gggctccgac gaggacgcca agatgatcgt   3060
ggaggccaag ccgggccacg ccctcgtggg cttcgagatg tccaacgact ccatcaccgt   3120
gctcaaggtg tacgaggcca agctcaagca gaactaccag gtggacaagg actccctctc   3180
cgaggtgatc tacggcgaca ccgacaagct cttctgcccg gaccagtccg agcagatata   3240
ctacaccaac aacatcgtgt cccgaacga gtacgtgatc accaagatcg acttcaccaa   3300
gaagatgaag accctccgct acgaggtgac cgccaacttc tacgactcct ccaccggcga   3360
gatcgacctc aacaagaaga aggtggagtc ctccgaggcc gagtaccgca ccctctccgc   3420
caacgacgac ggcgtgtaca tgccgctcgg cgtgatctcc gaaaccttcc tcaccccgat   3480
caacggcttc ggcctccagg ccgacgagaa ctcccgcctc atcaccctca cctgcaagtc   3540
ctacctccgc gagctgctcc tcgccaccga cctctccaac aaggagacca agctcatcgt   3600
gccgccgtcc ggcttcatct ccaacatcgt ggagaacggc tccatcgagg aggacaacct   3660
cgagccgtgg aaggccaaca acaagaacgc ctacgtggac cacaccggcg gcgtgaacgg   3720
caccaaggcc ctctacgtgc acaaggacgg cggcttctcc cagttcatcg gcgacaagct   3780
caagccgaag accgagtacg tgatccagta caccgtgaag ggcaagccgt ccatccacct   3840
caaggacgag aacaccggct acatccacta cgaggacacc aacaacaacc tcaaggacta   3900
ccagaccatc accaagcgct tcaccaccgg caccgacctc aagggcgtgt acctcatcct   3960
caagtcccag aacggcgacg aggcctgggg cgacaagttc accatccttg agatcaagcc   4020
ggccgaggac ctcctctccc cggagctgat caacccgaac tcctggatca ccaccccggg   4080
cgcctccatc tccggcaaca agctcttcat caacctcggc accaacggca ccttccgcca   4140
gtccctctcc ctcaactcct actccaccta ctccatctcc ttcaccgcct ccggcccgtt   4200
caacgtgacc gtgcgcaact cccgcagggt gctcttcgag cgctccaacc tcatgtcctc   4260 caccctcccac atctccggca ccttcaagac cgagtccaac aacaccggcc tctacgtgga   4320
gctgtcccgc cgctccggcg gcggcggcca catctccttc gagaacgtgt ccatcaagta   4380
gatctgagct ctagatcccc gaatttcccc gatcgttcaa acatttggca ataaagtttc   4440
ttaagattga atcctgttgc cggtcttgcg atgattatca taaatttct gttgaattac   4500 gttaagcatg taataattaa catgtaatgc atgacgttat ttatgagatg gttttttatg   4560
attagagtcc cgcaattata catttaatac gcgatagaaa acaaaatata gcgcgcaaac   4620
taggataaat tatcgcgcgc ggtgtcatct atgttactag atcgggaatt gggtaccagc   4680
ttgcatgcct gcagtgcagc gtgacccggt cgtgcccctc tctagagata atgagcattg   4740
catgtctaag ttataaaaaa ttaccacata ttttttttgt cacacttgtt tgaagtgcag   4800
tttatctatc tttatacata tatttaaact ttactctacg aataatataa tctatagtac   4860
```

```
tacaataata tcagtgtttt agagaatcat ataaatgaac agttagacat ggtctaaagg    4920
acaattgagt attttgacaa caggactcta cagttttatc ttttagtgt gcatgtgttc      4980 tcctttttt ttgcaaatag cttcacctat ataatacttc atccatttta ttagtacatc     5040
catttagggt ttaggttaa tggttttat agactaattt ttttagtaca tctatttat       5100 tctatttag cctctaaatt aagaaaacta aactctatt ttagttttt tatttaataa        5160 tttagatata aaatagaata aaataaagtg actaaaaatt aaacaaatac ccttaagaa      5220 attaaaaaaa ctaaggaaac atttttcttg tttcgagtag ataatgccag cctgttaaac    5280
gccgtcgacg agtctaacgg acaccaacca gcgaaccagc agcgtcgcgt cgggccaagc    5340
gaagcagacg gcacggcatc tctgtcgctg cctctggacc cctctcgaga gttccgctcc    5400
accgttggac ttgctccgct gtcggcatcc agaaattgcg tggcggagcg gcagacgtga    5460
gccggcacgg caggcggcct cctcctcctc tcacggcacc ggcagctacg ggggattcct    5520
ttcccaccgc tccttcgctt ttccttcctc gcccgccgta ataaatagac acccctcca     5580 caccctcttt ccccaacctc gtgttgttcg gagcgcacac acacacaacc agatctcccc    5640
caaatccacc cgtcggcacc tccgcttcaa ggtacgccgc tcgtcctccc cccccccccc    5700
tctctacctt ctctagatcg gcgttccggt ccatggttag ggcccggtag ttctacttct    5760
gttcatgttt gtgttagatc cgtgtttgtg ttagatccgt gctgctagcg ttcgtacacg    5820
gatgcgacct gtacgtcaga cacgttctga ttgctaactt gccagtgttt ctctttgggg    5880
aatcctggga tggctctagc cgttccgcag acgggatcga tttcatgatt ttttttgttt    5940
cgttgcatag ggtttggttt gccctttcc tttatttcaa tatatgccgt gcacttgttt     6000
gtcgggtcat cttttcatgc ttttttttgt cttggttgtg atgatgtggt ctggttgggc    6060
ggtcgttcta gatcggagta gaattctgtt tcaaactacc tggtggattt attaattttg    6120
gatctgtatg tgtgtgccat acatattcat agttacgaat tgaagatgat ggatggaaat    6180
atcgatctag gataggtata catgttgatg cgggttttac tgatgcatat acagagatgc    6240
tttttgttcg cttggttgtg atgatgtggt gtggttgggc ggtcgttcat tcgttctaga    6300
tcggagtaga atactgtttc aaactacctg gtgtatttat taattttgga actgtatgtg    6360
tgtgtcatac atcttcatag ttacgagttt aagatggatg gaaatatcga tctaggatag    6420
gtatacatgt tgatgtgggt tttactgatg catatacatg atggcatatg cagcatctat    6480
tcatatgctc taaccttgag tacctatcta ttataataaa caagtatgtt ttataattat    6540
tttgatcttg atatacttgg atgatggcat atgcagcagc tatatgtgga tttttttagc    6600
cctgccttca tacgctattt atttgcttgg tactgtttct tttgtcgatg ctcaccctgt    6660
tgtttggtgt tacttctgca gggatccccg atcatgcaaa aactcattaa ctcagtgcaa    6720
aactatgcct ggggcagcaa aacggcgttg actgaacttt atggtatgga aaatccgtcc    6780
agccagccga tggccgagct gtggatgggc gcacatccga aaagcagttc acgagtgcag    6840
aatgccgccg gagatatcgt ttcactgcgt gatgtgattg agagtgataa atcgactctg    6900
ctcggagagg ccgttgccaa acgctttggc gaactgcctt tcctgttcaa agtattatgc    6960
gcagcacagc cactctccat tcaggttcat ccaaacaaac acaattctga aatcggtttt    7020
gccaaagaaa atgccgcagg tatcccgatg gatgccgccg agcgtaacta taaagatcct    7080
aaccacaagc cggagctggt ttttgcgctg acgcctttcc ttgcgatgaa cgcgtttcgt    7140
gaattttccg agattgtctc cctactccag ccggtcgcag gtgcacatcc ggcgattgct    7200
cactttttac aacagcctga tgccgaacgt ttaagcgaac tgttcgccag cctgttgaat    7260
```

```
atgcagggtg aagaaaaatc ccgcgcgctg gcgattttaa aatcggccct cgatagccag    7320
cagggtgaac cgtggcaaac gattcgttta atttctgaat tttacccgga agacagcggt    7380
ctgttctccc cgctattgct gaatgtggtg aaattgaacc ctggcgaagc gatgttcctg    7440
ttcgctgaaa caccgcacgc ttacctgcaa ggcgtggcgc tggaagtgat ggcaaactcc    7500
gataacgtgc tgcgtgcggg tctgacgcct aaatacattg atattccgga actggttgcc    7560
aatgtgaaat tcgaagccaa accggctaac cagttgttga cccagccggt gaaacaaggt    7620
gcagaactgg acttcccgat tccagtggat gattttgcct tctcgctgca tgaccttagt    7680
gataaagaaa ccaccattag ccagcagagt gccgccattt tgttctgcgt cgaaggcgat    7740
gcaacgttgt ggaaaggttc tcagcagtta cagcttaaac cgggtgaatc agcgtttatt    7800
gccgccaacg aatcaccggt gactgtcaaa ggccacggcc gtttagcgcg tgtttacaac    7860
aagctgtaag agcttactga aaaaattaac atctcttgct aagctgggag ctcgatccgt    7920
cgacctgcag atcgttcaaa catttggcaa taaagtttct taagattgaa tcctgttgcc    7980
ggtcttgcga tgattatcat ataatttctg ttgaattacg ttaagcatgt aataattaac    8040
atgtaatgca tgacgttatt tatgagatgg gttttatga ttagagtccc gcaattatac    8100
atttaatacg cgatagaaaa caaaatatag cgcgcaaact aggataaatt atcgcgcgcg    8160
gtgtcatcta tgttactaga tctgctagcc ctgcaggaaa tttaccggtg cccgggcggc    8220
cagcatggcc gtatccgcaa tgtgttatta agttgtctaa gcgtcaattt gtttacacca    8280
caatatatcc tgccaccagc cagccaacag ctcccccgacc ggcagctcgg cacaaaatca    8340
ccactcgata caggcagccc atcagaatta attctcatgt ttgacagctt atcatcgact    8400
gcacggtgca ccaatgcttc tggcgtcagg cagccatcgg aagctgtggt atggctgtgc    8460
aggtcgtaaa tcactgcata attcgtgtcg ctcaaggcgc actcccgttc tggataatgt    8520
tttttgcgcc gacatcataa cggttctggc aaatattctg aaatgagctg ttgacaatta    8580
atcatccggc tcgtataatg tgtggaattg tgagcggata acaatttcac acaggaaaca    8640
gaccatgagg gaagcgttga tcgccgaagt atcgactcaa ctatcagagg tagttggcgt    8700
catcgagcgc catctcgaac cgacgttgct ggccgtacat ttgtacggct ccgcagtgga    8760
tggcggcctg aagccacaca gtgatattga tttgctggtt acggtgaccg taaggcttga    8820
tgaaacaacg cggcgagctt tgatcaacga ccttttggaa acttcggctt ccctggaga    8880 gagcgagatt ctccgcgctg tagaagtcac cattgttgtg cacgacgaca tcattccgtg    8940
gcgttatcca gctaagcgcg aactgcaatt tggagaatgg cagcgcaatg acattcttgc    9000
aggtatcttc gagccagcca cgatcgacat tgatctggct atcttgctga caaaagcaag    9060
agaacatagc gttgccttgg taggtccagc ggcggaggaa ctctttgatc cggttcctga    9120
acaggatcta tttgaggcgc taaatgaaac cttaacgcta tggaactcgc cgcccgactg    9180
ggctggcgat gagcgaaatg tagtgcttac gttgtcccgc atttggtaca gcgcagtaac    9240
cggcaaaatc gcgccgaagg atgtcgctgc cgactgggca atggagcgcc tgccggccca    9300
gtatcagccc gtcatacttg aagctaggca ggcttatctt ggacaagaag atcgcttggc    9360
ctcgcgcgca gatcagttgg aagaatttgt tcactacgtg aaaggcgaga tcaccaaagt    9420
agtcggcaaa taaagctcta gtggatctcc gtaccccccgg gggatctggc tcgcggcgga    9480
cgcacgacgc cggggcgaga ccataggcga tctcctaaat caatagtagc tgtaacctcg    9540
aagcgtttca cttgtaacaa cgattgagaa ttttttgtcat aaaattgaaa tacttggttc    9600
```

-continued

```
gcattttgt catccgcggt cagccgcaat tctgacgaac tgcccattta gctggagatg    9660
attgtacatc cttcacgtga aaatttctca agcgctgtga acaagggttc agattttaga    9720
ttgaaaggtg agccgttgaa acacgttctt cttgtcgatg acgacgtcgc tatgcggcat    9780
cttattattg aataccttac gatccacgcc ttcaaagtga ccgcggtagc cgacagcacc    9840
cagttcacaa gagtactctc ttccgcgacg gtcgatgtcg tggttgttga tctaaattta    9900
ggtcgtgaag atgggctcga gatcgttcgt aatctggcgg caaagtctga tattccaatc    9960
ataattatca gtggcgaccg ccttgaggag acggataaag ttgttgcact cgagctagga   10020
gcaagtgatt ttatcgctaa gccgttcagt atcagagagt ttctagcacg cattcgggtt   10080
gccttgcgcg tgcgcccaa cgttgtccgc tccaaagacc gacggtcttt tgtttttact    10140
gactggacac ttaatctcag gcaacgtcgc ttgatgtccg aagctggcgg tgaggtgaaa   10200
cttacggcag gtgagttcaa tcttctcctc gcgttttag agaaacccg cgacgttcta    10260 tcgcgcgagc aacttctcat tgccagtcga gtacgcgacg aggaggttta tgacaggagt   10320
atagatgttc tcattttgag gctgcgccgc aaacttgagg cagatccgtc aagccctcaa   10380
ctgataaaaa cagcaagagg tgccggttat ttctttgacg cggacgtgca ggtttcgcac   10440
ggggggacga tggcagcctg agccaattcc cagatccccg aggaatcggc gtgagcggtc   10500
gcaaaccatc cggcccggta caaatcggcg cggcgctggg tgatgacctg gtggagaagt   10560
tgaaggccgc gcaggccgcc cagcggcaac gcatcgaggc agaagcacgc cccggtgaat   10620
cgtggcaagc ggccgctgat cgaatccgca agaatcccg gcaaccgccg gcagccggtg    10680
cgccgtcgat taggaagccg cccaagggcg acgagcaacc agatttttc gttccgatgc    10740 tctatgacgt gggcacccgc gatagtcgca gcatcatgga cgtggccgtt tccgtctgt    10800 cgaagcgtga ccgacgagct ggcgaggtga tccgctacga gcttccagac gggcacgtag   10860
aggtttccgc agggccggcc ggcatggcca gtgtgtggga ttacgacctg gtactgatgg   10920
cggtttccca tctaaccgaa tccatgaacc gataccggga agggaaggga gacaagcccg   10980
gccgcgtgtt ccgtccacac gttgcggacg tactcaagtt ctgccggcga ccgatggcg    11040 gaaagcagaa agacgacctg gtagaaacct gcattcggtt aaacaccacg cacgttgcca   11100
tgcagcgtac gaagaaggcc aagaacggcc gcctggtgac ggtatccgag ggtgaagcct   11160
tgattagccg ctacaagatc gtaaagagcg aaaccgggcg gccggagtac atcgagatcg   11220
agctagctga ttggatgtac cgcgagatca cagaaggcaa gaacccggac gtgctgacgg   11280
ttcaccccga ttacttttg atcgatcccg gcatcggccg ttttctctac cgcctggcac   11340
gccgcgccgc aggcaaggca gaagccagat ggttgttcaa gacgatctac gaacgcagtg   11400
gcagcgccgg agagttcaag aagttctgtt tcaccgtgcg caagctgatc gggtcaaatg   11460
acctgccgga gtacgatttg aaggaggagg cggggcaggc tggcccgatc ctagtcatgc   11520
gctaccgcaa cctgatcgag ggcgaagcat ccgccggttc ctaatgtacg gagcagatgc   11580
tagggcaaat tgccctagca ggggaaaaag gtcgaaaagg tctctttcct gtggatagca   11640
cgtacattgg gaacccaaag ccgtacattg ggaaccggaa cccgtacatt gggaacccaa   11700
agccgtacat tgggaaccgg tcacacatgt aagtgactga tataaaagag aaaaaaggcg   11760 attttccgc ctaaaactct ttaaaactta ttaaaactct aaaaaccgc ctggcctgtg     11820 cataactgtc tggccagcgc acagccgaag agctgcaaaa agcgcctacc cttcggtcgc   11880
tgcgctccct acgcccgcc gcttcgcgtc ggcctatcgc ggccgctggc cgctcaaaaa    11940
tggctggcct acggccaggc aatctaccag ggcgcggaca agccgcgccg tcgccactcg   12000
```

```
accgccggcg ctgaggtctg cctcgtgaag aaggtgttgc tgactcatac caggcctgaa    12060
tcgccccatc atccagccag aaagtgaggg agccacggtt gatgagagct tgttgtagg     12120 tggaccagtt ggtgattttg aacttttgct ttgccacgga acggtctgcg ttgtcgggaa    12180
gatgcgtgat ctgatccttc aactcagcaa aagttcgatt tattcaacaa agccgccgtc    12240
ccgtcaagtc agcgtaatgc tctgccagtg ttacaaccaa ttaaccaatt ctgattagaa    12300
aaactcatcg agcatcaaat gaaactgcaa tttattcata tcaggattat caataccata    12360
tttttgaaaa agccgtttct gtaatgaagg agaaaactca ccgaggcagt tccataggat    12420
ggcaagatcc tggtatcggt ctgcgattcc gactcgtcca acatcaatac aacctattaa    12480
tttcccctcg tcaaaaataa ggttatcaag tgagaaatca ccatgagtga cgactgaatc    12540
cggtgagaat ggcaaaagct ctgcattaat gaatcggcca acgcgcgggg agaggcggtt    12600
tgcgtattgg cgctcttcc gcttcctcgc tcactgactc gctgcgctcg tcgttcggc     12660 tgcggcgagc ggtatcagct cactcaaagg cggtaatacg gttatccaca gaatcagggg    12720
ataacgcagg aaagaacatg tgagcaaaag gccagcaaaa ggccaggaac cgtaaaaagg    12780
ccgcgttgct ggcgtttttc cataggctcc gccccctga cgagcatcac aaaaatcgac      12840
gctcaagtca gaggtggcga aacccgacag gactataaag ataccaggcg tttccccctg    12900
gaagctccct cgtgcgctct cctgttccga ccctgccgct taccggatac ctgtccgcct    12960
ttctcccttc gggaagcgtg gcgctttctc atagctcacg ctgtaggtat ctcagttcgg    13020
tgtaggtcgt tcgctccaag ctgggctgtg tgcacgaacc ccccgttcag cccgaccgct    13080
gcgccttatc cggtaactat cgtcttgagt ccaacccggt aagacacgac ttatcgccac    13140
tggcagcagc cactggtaac aggattagca gagcgaggta tgtaggcggt gctacagagt    13200
tcttgaagtg gtggcctaac tacggctaca ctagaagaac agtatttggt atctgcgctc    13260
tgctgaagcc agttaccttc ggaaaaagag ttggtagctc ttgatccggc aaacaaacca    13320
ccgctggtag cggtggtttt tttgtttgca agcagcagat tacgcgcaga aaaaaggat    13380 ctcaagaaga tccttgatc ttttctacgg ggtctgacgc tcagtggaac gaaaactcac    13440
gttaagggat tttggtcatg agattatcaa aaaggatctt cacctagatc cttttgatcc    13500
ggaattaatt cctgtggttg gcatgcacat acaaatggac gaacggataa accttttcac    13560
gcccttttaa atatccgatt attctaataa acgctctttt ctcttaggtt tacccgccaa    13620
tatatcctgt caaacactga tagtttaaac tgaaggcggg aaacgacaat ctgatcatga    13680
gcggagaatt aagggagtca cgttatgacc cccgccgatg acgcgggaca agccgttta    13740 cgtttggaac tgacagaacc gcaacgctgc aggaattggc cgcagcggcc atttaaatca    13800
attgggcgcg ccgaattcga gctcggtac                                     13829
```

<210> SEQ ID NO 31
<211> LENGTH: 2367
<212> TYPE: DNA
<213> ORGANISM: Bacillus thuringiensis
<220> FEATURE:
<221> NAME/KEY: misc_feature
<222> LOCATION: (1)..(2367)
<223> OTHER INFORMATION: Vip3C-12168 coding sequence
<400> SEQUENCE: 31

```
atgaatatga ataatactaa attaaacgca agggccctac cgagtttat tgattatttt       60 aatggcattt atgatttgc cactggtatc aaagacatta tgaatatgat ttttaaaacg       120
```

```
gatacaggtg gtaatctaac cttagacgaa atcctaaaga atcagcagtt actaaatgag      180
atttctggta aattggatgg ggtaaatggg agcttaaatg atcttatcgc acagggaaac      240
ttaaatacag aattatctaa ggaaatctta aaaattgcaa atgaacagaa tcaagtctta      300
aatgatgtta ataacaaact cgatgcgata aatacgatgc ttcatatata tctacctaaa      360
attacatcta tgttaagtga tgtaatgaag caaaattatg cgctaagtct gcaaatagaa      420
tacttaagta agcaattgca agaaatttct gataaattag atattattaa cgtaaatgtt      480
cttattaact ctacacttac tgaaattaca cctgcatatc aacggattaa atatgtgaat      540
gaaaaatttg aagaattaac ttttgctaca gaaaccactt taaaagtaaa aaaggatagc      600
tcgcctgctg atattcttga tgagttaact gaattaactg aactagcgaa aagtgttaca      660
aaaaatgacg ttgatggttt tgaattttac cttaatacat ccacgatgt aatggtagga      720 aataatttat tcgggcgttc agctttaaaa actgcttcag aattaattgc taagaaaat      780 gtgaaaacaa gtggcagtga agtaggaaat gtttataatt tcttaattgt attaacagct      840
ctacaagcaa aagcttttct tactttaaca acatgccgaa attattaagg cttagcagat      900
attgattata cttctattat gaatgaacat ttaaataagg aaaagagga atttagagta      960 aacatccttc ctacactttc taatactttt tctaatccta attatgcaaa agttaaagga     1020
agtgatgaag atgcaaagat gattgtggaa gctaaaccag acatgcatt ggttgggttt     1080 gaaatgagca atgattcaat cacagtatta aagtatatg aggctaagct aaaacaaaat     1140
tatcaagttg ataaggattc cttatcggag gttatttatg gtgatacgga taaattattt     1200
tgtccagatc aatctgaaca aatatattat acaaataaca tagtattccc aaatgaatat     1260
gtaattacta aaattgattt cactaaaaaa atgaaaactt taagatatga ggtaacagcg     1320 aattttatg attcttctac aggagaaatt gacttaaata agaaaaagt agaatcaagt     1380 gaagcggagt atagaacgtt aagtgctaat gatgatggag tgtatatgcc attaggtgtc     1440
atcagtgaaa catttttgac tccgataaat gggtttggcc tccaagctga tgaaattca     1500 agattaatta ctttaacatg taaatcatat ttaagagaac tactgctagc aacagactta     1560
agcaataaag aaactaaatt gatcgtccca ccaagtggtt ttattagcaa tattgtagag     1620
aacgggtcca tagaagagga caatttagag ccgtggaaag caataataa gaatgcgtat     1680 gtagatcata caggcggagt gaatggaact aaagctttat atgttcataa ggacggagga     1740
ttttcacaat ttattggaga taagttaaaa ccgaaaactg agtatgtaat ccaatatact     1800
gttaaaggaa aaccttctat tcatttaaaa gatgaaaata ctggatatat tcattatgaa     1860
gatacaaata ataatttaaa agattatcaa actattacta aacgttttac tacaggaact     1920
gatttaaagg gagtgtattt aattttaaaa agtcaaaatg gagatgaagc ttgggagat     1980 aaatttacaa ttttagaaat taagcctgcg gaggattat taagcccaga attaattaat     2040
ccgaattctt ggattacgac tccagggggct agcatttcag gaaataaact tttcattaac     2100
ttggggacaa atgggacctt tagacaaagt ctttcattaa acagttattc aacttatagt     2160
ataagcttta ctgcatcagg accatttaat gtgacggtaa gaaattctag ggaagtatta     2220
tttgaacgaa gcaaccttat gtcttcaact agtcatattt ctgggacatt caaaactgaa     2280
tccaataata ccggattata tgtagaactt tcccgtcgct ctggtggtgg tggtcatata     2340
tcatttgaaa acgtttctat taaataa                                         2367
```

<210> SEQ ID NO 32
<211> LENGTH: 788

```
<212> TYPE: PRT
<213> ORGANISM: Bacillus thuringiensis
<220> FEATURE:
<221> NAME/KEY: MISC_FEATURE
<222> LOCATION: (1)..(788)
<223> OTHER INFORMATION: Vip3C-12168 toxin

<400> SEQUENCE: 32
```

Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Val Gly Phe Glu Met Ser Asn Asp Ser Ile Thr
        355                 360                 365

Val Leu Lys Val Tyr Glu Ala Lys Leu Lys Gln Asn Tyr Gln Val Asp

```
              370                 375                 380
Lys Asp Ser Leu Ser Glu Val Ile Tyr Gly Asp Thr Asp Lys Leu Phe
385                 390                 395                 400

Cys Pro Asp Gln Ser Glu Gln Ile Tyr Thr Asn Asn Ile Val Phe
                405                 410                 415

Pro Asn Glu Tyr Val Ile Thr Lys Ile Asp Phe Thr Lys Lys Met Lys
                420                 425                 430

Thr Leu Arg Tyr Glu Val Thr Ala Asn Phe Tyr Asp Ser Ser Thr Gly
            435                 440                 445

Glu Ile Asp Leu Asn Lys Lys Lys Val Glu Ser Ser Glu Ala Glu Tyr
            450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
                500                 505                 510

Glu Leu Leu Leu Ala Thr Asp Leu Ser Asn Lys Glu Thr Lys Leu Ile
            515                 520                 525

Val Pro Pro Ser Gly Phe Ile Ser Asn Ile Val Glu Asn Gly Ser Ile
530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Phe Ser Gln Phe Ile Gly Asp Lys Leu Lys Pro Lys
                580                 585                 590

Thr Glu Tyr Val Ile Gln Tyr Thr Val Lys Gly Lys Pro Ser Ile His
            595                 600                 605

Leu Lys Asp Glu Asn Thr Gly Tyr Ile His Tyr Glu Asp Thr Asn Asn
610                 615                 620

Asn Leu Lys Asp Tyr Gln Thr Ile Thr Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Lys Phe Thr Ile Leu Glu Ile Lys Pro Ala Glu Asp
                660                 665                 670

Leu Leu Ser Pro Glu Leu Ile Asn Pro Asn Ser Trp Ile Thr Thr Pro
            675                 680                 685

Gly Ala Ser Ile Ser Gly Asn Lys Leu Phe Ile Asn Leu Gly Thr Asn
            690                 695                 700

Gly Thr Phe Arg Gln Ser Leu Ser Leu Asn Ser Tyr Ser Thr Tyr Ser
705                 710                 715                 720

Ile Ser Phe Thr Ala Ser Gly Pro Phe Asn Val Thr Val Arg Asn Ser
                725                 730                 735

Arg Glu Val Leu Phe Glu Arg Ser Asn Leu Met Ser Ser Thr Ser His
                740                 745                 750

Ile Ser Gly Thr Phe Lys Thr Glu Ser Asn Asn Thr Gly Leu Tyr Val
            755                 760                 765

Glu Leu Ser Arg Arg Ser Gly Gly Gly His Ile Ser Phe Glu Asn
    770                 775                 780

Val Ser Ile Lys
785
```

<210> SEQ ID NO 33
<211> LENGTH: 2367
<212> TYPE: DNA
<213> ORGANISM: Artificial Sequence
<220> FEATURE:
<223> OTHER INFORMATION: Maize optimized Vip3C-12168

<400> SEQUENCE: 33

```
atgaacaaga acaacaccaa gctcaacgcc cgcgccctcc cgtccttcat cgactacttc      60
aacggcatct acggcttcgc caccggcatc aaggacatca tgaacatgat cttcaagacc     120
gacaccggcg gcaacctcac cctcgacgag atcctcaaga accagcagct cctcaacgag     180
atcagcggca agctcgacgg cgtgaacggc tccctcaacg acctcatcgc ccagggcaac     240
ctcaacaccg agctgtccaa ggagatcctc aagatcgcca acgagcagaa ccaggtgctc     300
aacgacgtga acaacaagct cgacgccatc aacaccatgc tccacatcta cctcccgaag     360
atcacctcca tgctctccga cgtgatgaag cagaactacg ccctctccct ccagatcgag     420
tacctctcca gcagctcca ggagatcagc gacaagctcg acatcatcaa cgtgaacgtg     480
ctcatcaact ccaccctcac cgagatcacc ccggcctacc agcgcatcaa gtacgtgaac     540
gagaagttcg aggagctgac cttcgccacc gagaccaccc tcaaggtgaa gaaggactcc     600
tccccggccg acatcctcga cgagctgacc gagctgaccg agctggccaa gtccgtgacc     660
aagaacgacg tggacggctt cgagttctac ctcaacacct tccacgacgt gatggtgggc     720
aacaacctct cggccgctc cgccctcaag accgcctccg agctgatcgc caaggagaac     780
gtgaagacct ccggctccga ggtgggcaac gtgtacaact tcctcatcgt gctcaccgcc     840
ctgcaggcca aggccttcct caccctcacc acctgccgca agctcctcgg cctcgccgac     900
atcgactaca cctccatcat gaacgagcac ctcaacaagg agaaggagga gttccgcgtg     960
aacatcctcc cgaccctctc caacaccttc tccaacccga actacgccaa ggtgaagggc    1020
tccgacgagg acgccaagat gatcgtggag gccaagccgg ccacgccct cgtgggcttc    1080
gagatgtcca cgactccat caccgtgctc aaggtgtacg aggccaagct caagcagaac    1140
taccaggtgg acaaggactc cctctccgag gtgatctacg gcgacaccga caagctcttc    1200
tgccccggacc agtccgagca gatatactac accaacaaca tcgtgttccc gaacgagtac    1260
gtgatcacca gatcgacttc accaagaag atgaagaccc tccgctacga ggtgaccgcc    1320
aacttctacg actcctccac cggcgagatc gacctcaaca agaagaaggt ggagtcctcc    1380
gaggccgagt accgcaccct ctccgccaac gacgacggcg tgtacatgcc gctcggcgtg    1440
atctccgaaa ccttcctcac cccgatcaac ggcttcggcc tccaggccga cgagaactcc    1500
cgcctcatca ccctcacctg caagtcctac ctccgcgagc tgctcctcgc caccgacctc    1560
tccaacaagg agaccaagct catcgtgccg ccgtccggct tcatctccaa catcgtggag    1620
aacggctcca tcgaggagga caacctcgag ccgtggaagg ccaacaacaa gaacgcctac    1680
gtggaccaca ccggcggcgt gaacggcacc aaggccctct acgtgcacaa ggacggcggc    1740
ttctcccagt tcatcggcga caagctcaag ccgaagaccg agtacgtgat ccagtacacc    1800
gtgaagggca agccgtccat ccacctcaag gacgagaaca ccggctacat ccactacgag    1860
gacaccaaca caacctcaa ggactaccag accatcacca gcgcttcac caccggcacc    1920
gacctcaagg gcgtgtacct catcctcaag tcccagaacg gcgacgaggc ctggggcgac    1980
aagttcacca tccttgagat caagccggcc gaggacctcc tctccccgga gctgatcaac    2040
```

```
ccgaactcct ggatcaccac cccgggcgcc tccatctccg gcaacaagct cttcatcaac    2100
ctcggcacca acggcacctt ccgccagtcc ctctccctca actcctactc cacctactcc    2160
atctccttca ccgcctccgg cccgttcaac gtgaccgtgc gcaactcccg cgaggtgctc    2220
ttcgagcgct ccaacctcat gtcctccacc tcccacatct ccggcacctt caagaccgag    2280
tccaacaaca ccggcctcta cgtggagctg tcccgccgct ccggcggcgg cggccacatc    2340
tccttcgaga acgtgtccat caagtag                                        2367
```